United States Patent
Bicalho

(10) Patent No.: US 9,669,060 B2
(45) Date of Patent: Jun. 6, 2017

(54) COMPOSITIONS FOR PREVENTING AND TREATING UTERINE DISEASE

(75) Inventor: Rodrigo Carvalho Bicalho, Dryden, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 13/265,503

(22) PCT Filed: Apr. 22, 2010

(86) PCT No.: PCT/US2010/032048
§ 371 (c)(1),
(2), (4) Date: Nov. 10, 2011

(87) PCT Pub. No.: WO2010/124085
PCT Pub. Date: Oct. 28, 2010

(65) Prior Publication Data
US 2012/0052093 A1 Mar. 1, 2012

Related U.S. Application Data

(60) Provisional application No. 61/171,962, filed on Apr. 23, 2009.

(51) Int. Cl.
| *A61K 35/76* | (2015.01) |
| *A61K 35/74* | (2015.01) |
| *A61K 39/108* | (2006.01) |
| *A61K 35/00* | (2006.01) |

(52) U.S. Cl.
CPC .............. *A61K 35/76* (2013.01); *A61K 35/74* (2013.01); *A61K 39/0258* (2013.01); *A61K 2035/11* (2013.01); *C12N 2795/00032* (2013.01)

(58) Field of Classification Search
None
See application file for complete search history.

(56) References Cited

U.S. PATENT DOCUMENTS

| 4,606,919 A * | 8/1986 | Stojkovic et al. ......... 424/203.1 |
| 7,163,820 B1 | 1/2007 | Nagy |
| 2005/0196408 A1 | 9/2005 | Langermann |
| 2006/0094034 A1 | 5/2006 | Brousseau |
| 2006/0153878 A1 | 7/2006 | Savarino |
| 2007/0054358 A1 * | 3/2007 | Blattner et al. .............. 435/69.1 |
| 2008/0193470 A1 * | 8/2008 | Masignani et al. ........ 424/185.1 |

FOREIGN PATENT DOCUMENTS

| WO | WO 2006047517 | * | 5/2006 |
| WO | WO 2006/113907 | * | 10/2006 |

OTHER PUBLICATIONS

Lopes et al. Journal of Clinical Microbiology, Apr. 2005, p. 1968-1972.*
Alteri et al. (Sep. 24, 2009). Plos Pathog 5(9): e1000586. doi:10.1371/journal.ppat.10000586.*
NCBI Reference Sequence: NP_757248.1 (2002).*
NCBI Reference Sequence: NP_755448.1, 2002.*
Diels et al.Biotechnol. Prg. 2004, 20,1512-1517.*
Dogan et al. Veterinary Microbiology 116 (2006) 270-282.*
AstA (Arginine N-succinyltransferase, organism K12). Uniprot accession No. P0AE37 Dec. 6, 2005.*
GenEmbL accession # AB083880, 2002.*
Uniprot accession # Q8XBA6, 2002.*
Janka et al. Infect Immun. Jun. 2003;71(6):3634-8.*
Pouttu et al. Mol. Microbiol Mar. 1999; 31 (6):1747-57.*
Gene sequence for DNA gyrase subuunit B (gyrB) of *E. coli* Strain IHE3034 obtained May 13, 2015 from www.wbi.ac.uk/ena/data/view/ADE92273.*
Dobrindt et al. Journal of Bacteriology, Mar. 2003, vol. 185, No. 6 p. 1831-1840.*
GenBank accession # ABG72591.1, 2014.*
Nagy et al. Infection and Immunity 70.8 (2002):4406-4413.*
Johnson et al. J Infect Dis. (2000) 181 (1):261-272.*
10X PCR buffer leaflet from Sigma Aldrich PCR buffer. Retrieved May 31, 2016: https://www.sigmaaldrich.com/content/dam/sigma-aldrich/docs/Sigma/Datasheet/5/p2192dat.pdf.*
GenBank Accession No. JN176394 *E. coli* strain H19 DNA gyrase subunit B (gyrB) gene, partial cds.*

* cited by examiner

*Primary Examiner* — Oluwatosin Ogunbiyi
(74) *Attorney, Agent, or Firm* — Casimir Jones S.C.

(57) ABSTRACT

The present invention relates to methods and compositions for preventing and treating uterine disease, and in particular to vaccines and bacteriophage compositions for treating or preventing puerperal metritis, clinical endometritis and/or subclinical endometritis.

9 Claims, 17 Drawing Sheets

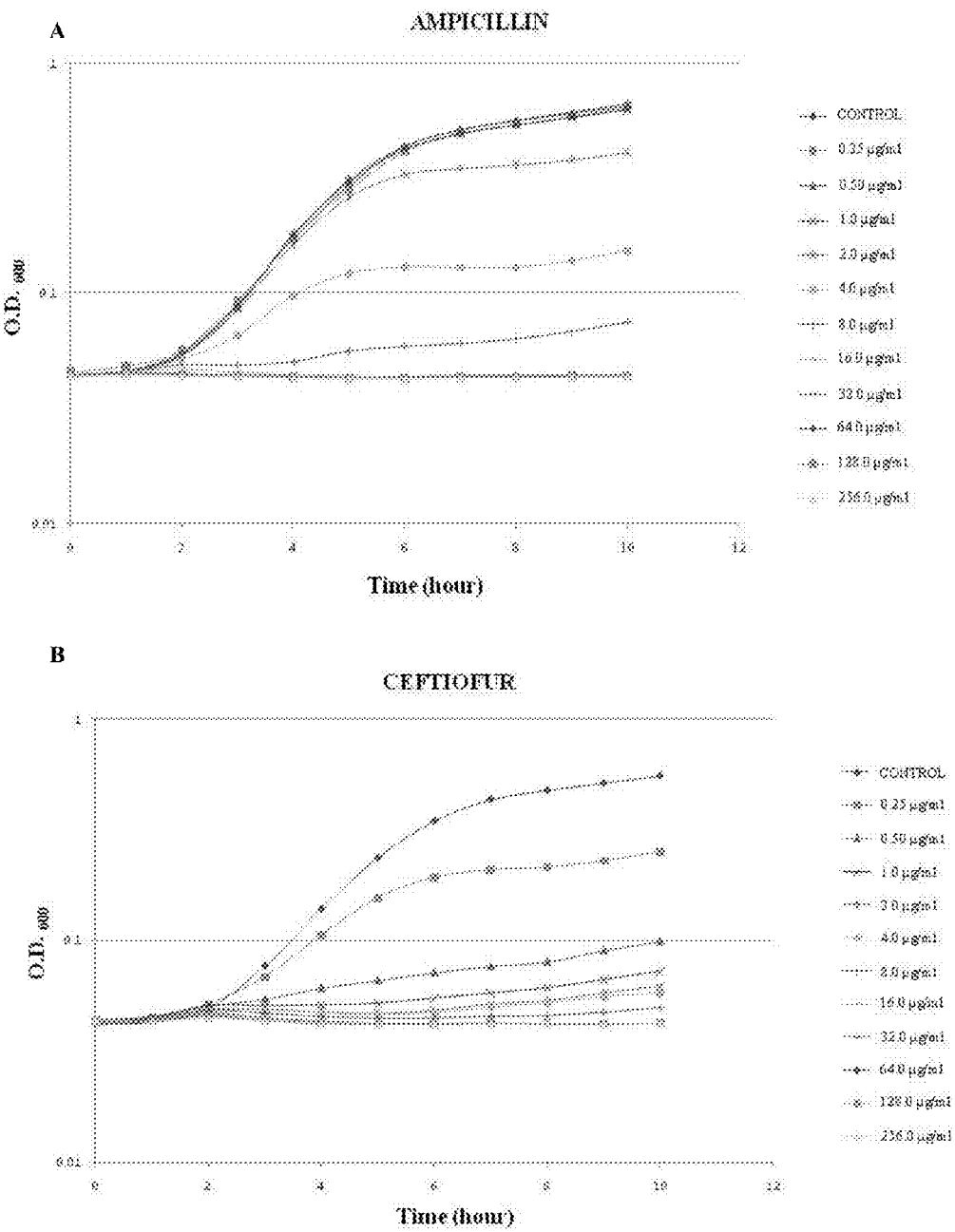

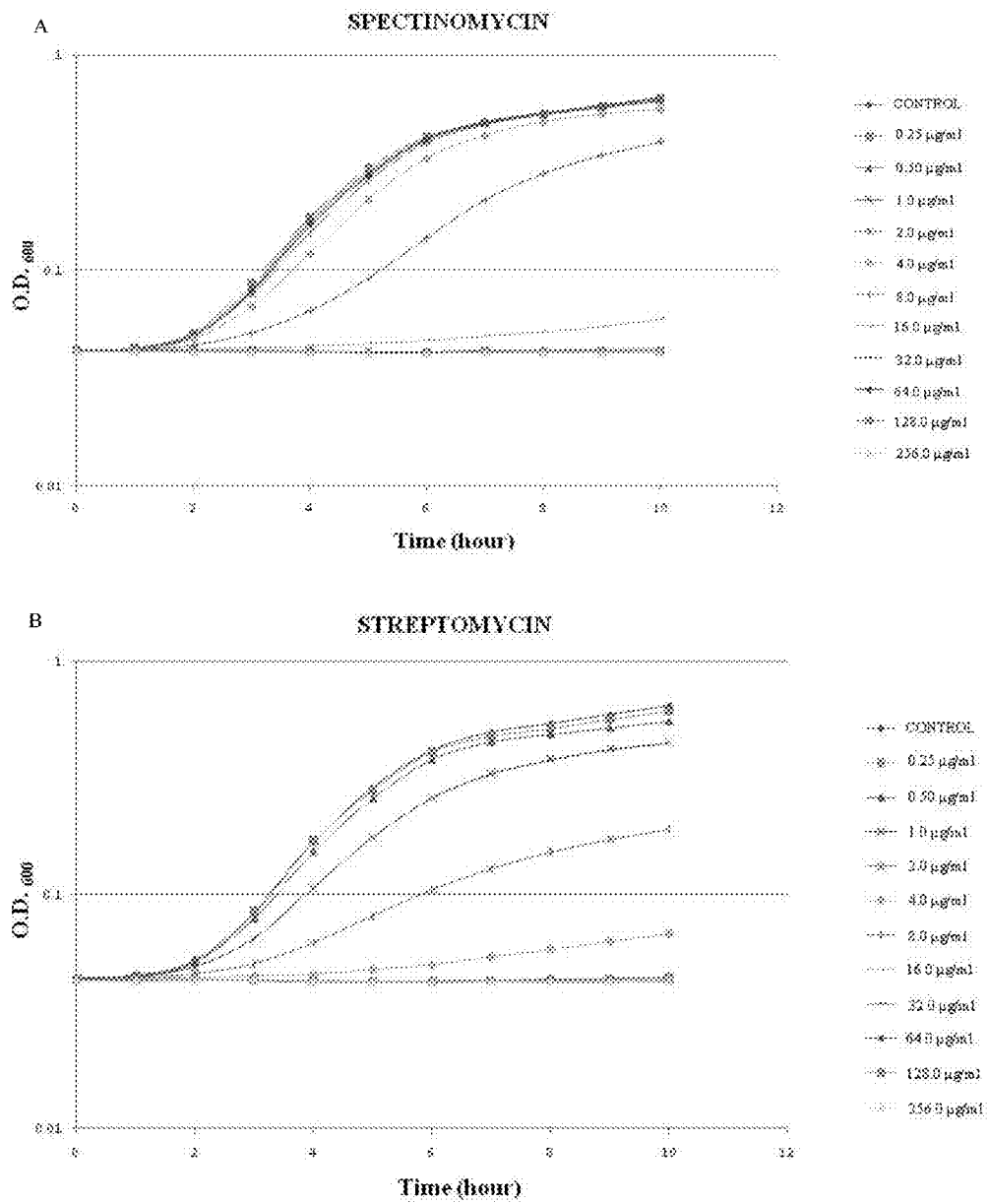

(Seq. I.D. NO.: 3)

ACTCCTATAAGTGTCCGGCGGTCTGCACGGCGTTGGTGTTTCGGTAGTAA
ACGCCCTGTCGCAAAAACTGGAGCTGGTTATCCAGCGCGAGGGTAAAATT
CACCGTCAGATCTACGAACACGGTGTACCGCAGGCCCCGCTGGCGGTTAC
CGGCGAGACTGAAAAAACCGGCACCATGGTGCGTTTCTGGCCCAGCCTCG
AAACCTTCACCAATGTGACCGAGTTCGAATATGAAATTCTGGCGAAACGT
CTGCGTGAGTTGTCGTTCCTCAACTCCGGCGTTTCCATTCGTCTGCGCGA
CAAGCGCGACGGCAAAGAAGACCACTTCCACTATGAAGGCGGCATCAAGG
CGTTCGTTGAATATCTGAACAAGAACAAAACGCCGATCCACCCGAATATC
TTCTACTTCTCCACTGAAAAGACGGTATTGGCGTCGAAGTGGCGTTGCA
GTGGAACGATGGCTTCCAGGAAAACATCTACTGCTTTACCAACAACATTC
CGCAGCGTGACGGCGGTACTCACCTGGCAGGCTTCCGTGCGGCGATGACC
CGTACCCTGAACGCCTACATGGACAAAGAAGGCTACAGCAAAAAAGCCAA
AGTTAGCGCCACCGGTGACGATGCGCGTGAAGGCCTGATTGCGGTCGTTT
CCGTGAAAGTGCCGGACCCGAAATTCTCCTCCCAGACCAAAGACAAACTG
GTTTCTTCTGAGGTGAAATCAGCGGTTGAACAGCAGATGAACGAACTGCT
GGCAGAATACCTGCTGGAAAACCCAACCGACGCGAAAATCGTGGTTGGCA
AAATCATCGATGCTGCCCGTGCCCGTGAAGCTGCGCGTCGTGCGCGTGAA
ATGACCCGCCGTAAAGGTGCGCTCGACTTAGCGGGCCTGCCGGGCAAACT
GGCANACTGCCAGGAACGCGATCCGGCGCTTTCCGAACTGTACCTGGTGG
AAAGGGACTCCGCAGGCGGCTCTGCGAANCANGGGCGTAACCGCAANAAC
NAGGCGATTCTGCNCTGAAGGNNAAA

Figure 14

(Seq. I.D. No.: 4)

ACTCCTATAAGTGTCCGGCGGTCTGCACGGCGTTGGTGTTTCGGTAGTAA
ACGCCCTGCTCGCAAAAACTGGAGCTGGTTATCCAGCGCGAGGGTAAAAT
TCACCGTCAGATCTACGAACACGGTGTACCGCAGGCCCCGCTGGCGGTTA
CCGGCGAGACTGAAAAAACCGGCACTATGGTGCGTTTCTGGCCAAGCCTT
GAAACCTTCACCAATGTGACCGAGTTCGAATATGACATTCTGGCGAAACG
TCTGCGTGAGTTGTCGTTCCTCAACTCCGGCGTTTCCATTCGTCTGCGCG
ACAAGCGCGACGGCAAAGAAGACCACTTCCACTATGAAGGCGGCATCAAG
GCGTTCGTTGAATATCTGAACAAGAACAAAACGCCGATCCACCCGAATAT
CTTCTACTTCTCCACCGAAAAAGACGGTATTGGCGTCGAAGTGGCGTTGC
AGTGGAACGATGGCTTCCAGGAAAACATCTACTGCTTTACCAACAACATT
CCGCAGCGTGACGGCGGTACTCACCTGGCAGGTTTCCGTGCGGCGATGAC
CCGTACTCTGAACGCCTACATGGACAAAGAAGGCTACAGCAAAAAAGCCA
AAGTCAGCGCCACCGGTGACGATGCGCGTGAAGGCCTGATTGCGGTCGTT
TCCGTGAAAGTGCCGGACCCGAAATTCTCCTCACAGACCAAAGACAAACT
GGTTTCTTCTGAGGTGAAATCGGCGGTTGAACAGCAGATGAACGAACTGC
TGGCGGAATACCTGCTGGAAAACCCAACCGACGCGAAAATCGTGGTCGGC
AAAATTATCGATGCTGCCCGTGCCCGTGAAGCTGCGCGTCGCGCGCGTGA
AATGACCCGCCGTAAAGGTGCGCTCGACTTAGCTGGCCTGCCGGGGCAAA
CTGGCANACTGCCAGGAACGCGATCCGGCGCTTTCCGAACTGTACCTTGT
GGAAAGGGACTCCGNGGGGCGGCTCTGCGAANCAAGGGCGTANCCCNANA
ACNAGGCGATTCTGCCCCTNAANGGTAAAN

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
gaagtcatca tgaccgttct gca                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
agcagggtac ggatgtgcga gcc                                              23

<210> SEQ ID NO 3
<211> LENGTH: 1026
<212> TYPE: DNA
<213> ORGANISM: Escherichia coli
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (979)..(979)
<223> OTHER INFORMATION: n is a, c, g, or t
<220> FEATURE:
<221> NAME/KEY: misc_feature
<222> LOCATION: (982)..(982)
<223> OTHER INFORMATION: n is a, c, g, or t
<220> FEATURE:
<221> NAME/KEY: misc_feature
<222> LOCATION: (997)..(997)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
```

<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1022)..(1023)
<223> OTHER INFORMATION: n is a, c, g, or t

<400> SEQUENCE: 3

```
actcctataa gtgtccggcg gtctgcacgg cgttggtgtt tcggtagtaa acgccctgtc      60
gcaaaaactg gagctggtta tccagcgcga gggtaaaatt caccgtcaga tctacgaaca     120
cggtgtaccg caggccccgc tggcggttac cggcgagact gaaaaaaccg gcaccatggt     180
gcgtttctgg cccagcctcg aaaccttcac caatgtgacc gagttcgaat atgaaattct     240
ggcgaaacgt ctgcgtgagt tgtcgttcct caactccggc gtttccattc gtctgcgcga     300
caagcgcgac ggcaaagaag accacttcca ctatgaaggc ggcatcaagg cgttcgttga     360
atatctgaac aagaacaaaa cgccgatcca cccgaatatc ttctacttct ccactgaaaa     420
agacggtatt ggcgtcgaag tggcgttgca gtggaacgat ggcttccagg aaaacatcta     480
ctgctttacc aacaacattc cgcagcgtga cggcggtact cacctggcag gcttccgtgc     540
ggcgatgacc cgtaccctga cgcctacat ggacaaagaa ggctacagca aaaagccaa      600
agttagcgcc accggtgacg atgcgcgtga aggcctgatt gcggtcgttt ccgtgaaagt     660
gccgacccg aaattctcct cccagaccaa agacaaactg gtttcttctg aggtgaaatc     720
agcggttgaa cagcagatga cgaactgct ggcagaatac ctgctggaaa acccaaccga     780
cgcgaaaatc gtggttggca aaatcatcga tgctgcccgt gcccgtgaag ctgcgcgtcg     840
tgcgcgtgaa atgacccgcc gtaaaggtgc gctcgactta gcgggcctgc cgggcaaact     900
ggcanactgc caggaacgcg atccggcgct ttccgaactg tacctggtgg aaagggactc     960
cgcaggcggc tctgcgaanc angggcgtaa ccgcaanaac naggcgattc tgcnctgaag    1020
gnnaaa                                                              1026
```

<210> SEQ ID NO 4
<211> LENGTH: 1030
<212> TYPE: DNA
<213> ORGANISM: Escherichia coli
<220> FEATURE:
<221> NAME/KEY: misc_feature
<222> LOCATION: (907)..(907)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t
<220> FEATURE:
<221> NAME/KEY: misc_feature
<222> LOCATION: (982)..(982)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (997)..(997)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t

```
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t

<400> SEQUENCE: 4
actcctataa gtgtccggcg gtctgcacgg cgttggtgtt tcggtagtaa acgccctgct      60
cgcaaaaact ggagctggtt atccagcgcg agggtaaaat tcaccgtcag atctacgaac     120
acggtgtacc gcaggccccg ctggcggtta ccggcgagac tgaaaaaacc ggcactatgg     180
tgcgtttctg gccaagcctt gaaaccttca ccaatgtgac cgagttcgaa tatgacattc     240
tggcgaaacg tctgcgtgag ttgtcgttcc tcaactccgg cgtttccatt cgtctgcgcg     300
acaagcgcga cggcaaagaa gaccacttcc actatgaagg cggcatcaag gcgttcgttg     360
aatatctgaa caagaacaaa acgccgatcc acccgaatat cttctacttc tccaccgaaa     420
aagacggtat tggcgtcgaa gtggcgttgc agtggaacga tggcttccag gaaaacatct     480
actgctttac caacaacatt ccgcagcgtg acggcggtac tcacctggca ggtttccgtg     540
cggcgatgac ccgtactctg aacgcctaca tggacaaaga aggctacagc aaaaaagcca     600
aagtcagcgc caccggtgac gatgcgcgtg aaggcctgat tgcggtcgtt tccgtgaaag     660
tgccggaccc gaaattctcc tcacagacca aagacaaact ggtttcttct gaggtgaaat     720
cggcggttga acagcagatg aacgaactgc tggcggaata cctgctggaa aacccaaccg     780
acgcgaaaat cgtggtcggc aaaattatcg atgctgcccg tgcccgtgaa gctgcgcgtc     840
gcgcgcgtga aatgacccgc cgtaaaggtg cgctcgactt agctggcctg ccggggcaaa     900
ctggcanact gccaggaacg cgatccggcg ctttccgaac tgtaccttgt ggaaagggac     960
tccgnggggc ggctctgcga ancaagggcg tanccnana  acnaggcgat tctgccctn     1020 aanggtaaan                                                           1030
```

COMPOSITIONS FOR PREVENTING AND TREATING UTERINE DISEASE

CROSS-REFERENCE TO RELATED APPLICATIONS

This application is a national stage entry of International Patent (PCT) Patent Application Serial No. PCT/US2010/032048, filed Apr. 22, 2010, which claims the benefit and priority to U.S. Provisional Patent Application Ser. No. 61/171,962, filed Apr. 23, 2009, the contents of each of which are hereby incorporated by reference for all purposes.

FIELD OF THE INVENTION

The present invention relates to methods and compositions for preventing and treating uterine disease, and in particular to vaccines and bacteriophage compositions for treating or preventing puerperal metritis, clinical endometritis and/or subclinical endometritis.

BACKGROUND OF THE INVENTION

Postpartum metritis is one of the most important disorders in cattle (Melendez et al., 2004). Approximately one third of postparturient cows develop metritis and 10 to 15% have clinical endometritis (Borsberry and Dobson, 1989). The consequences of metritis range from a subclinical infection, to illness with pyrexia, reduced milk yield, and occasionally death.

However, subclinical cases of metritis often progress to endometritis, which is an important cause of infertility and economic loss to the dairy industry (Gilbert et al., 2005). High prevalence rate of endometritis (53%) was found among US dairy herds using cytological methods for the diagnosis of uterine diseases (Gilbert et al., 2005).

Following calving, the uterus of over 90% of all cows becomes contaminated with bacteria (Sheldon et al., 2002), some of which are harmful and lead to establishment of infection and uterine disease (Bondurant, 1999). A diversity of bacteria can be isolated from the early postpartum uterine infection (Sheldon et al., 2004). *Escherichia coli* and *Arcanobacterium pyogenes* are the most common bacteria isolated from uterine infection, but other microorganisms such as *Fusobacterium necrophorum, Prevotella melaminogenicus Pseudomonas* spp., *Streptococcus* spp., *Staphylococcus* spp. and *Bacteroides* spp. are known to be responsible for puerperal metritis (Sheldon et al., 2004) {{48 Sheldon, I.M. 2004}}.

Ideally, therapy for uterine infection should eliminate pathogens from the uterus, and should result in a short as possible withdraw periods for milk and meat (Azawi, 2008). Although systemic or intrauterine antibiotic therapy is commonly used as the treatment of metritis (Azawi, 2008), it is recognized that antibiotic therapy cannot sterilize the uterus nor prevent recontamination that occurs during the early postpartum weeks (Sheldon and Dobson, 2004; Azawi, 2008). Furthermore, widespread usage of antimicrobials in food animal production has contributed to the emergence of antimicrobial resistance among pathogens that complicate the treatment of infectious diseases (Tollefson et al., 1999).

Additionally, the increasing level of resistance to frontline antimicrobial agents relevant to the treatment of human diseases is a significant public health concern (Tollefson and Miller, 2000) and has led to important changes in the perceptions and priorities of federal agencies with regard to antimicrobial usage as growth promoter and prophylactic agents (Angulo et al., 2004). US Food and Drug Administration (FDA), the United States Department of Agriculture (USDA) and the Center for Disease Control and Prevention (CDC) strongly promote the development of new classes of antimicrobials and other products able to eliminate or reduce risk of bacterial resistance (CDC Action Plan: On the world wide web at cdc.gov/drugresistance/actionplan/html/product.htm). The use of pathogenic-specific antimicrobials is expected to reduce the incidence of resistance development (Walsh, 2003).

Accordingly, what is needed in the art are alternative methods for preventing and treating uterine disease.

SUMMARY OF THE INVENTION

The present invention relates to methods and compositions for preventing and treating uterine disease, and in particular to vaccines and bacteriophage compositions for treating or preventing puerperal metritis, clinical endometritis and/or subclinical endometritis.

In some embodiments, the present invention provides an isolated strain of pathogenic *Escherichia coli* isolated from the uterus of an animal and expressing virulence factor fimH and at least one of astA, cdt, kpsII, ibeA, and hly. In some embodiments, the isolated strain of pathogenic *Escherichia coli* comprises a gyrB gene sequence at least 97% identical to one of SEQ ID NOs:3 and 4. In some embodiments, the isolated strain of pathogenic *Escherichia coli* has the characteristics of reference strains listed in FIG. 12. In some embodiments, the isolated strain of pathogenic *Escherichia coli* has the characteristics of reference strains IUPEC (cdt, ibeA, fimH, kpsII, fyfA, traT, rpa, aerJ) and IUPEC (asta, fimH, fyfA, sfa). In some embodiments, the isolated strain of pathogenic *Escherichia coli* has the characteristics of reference strains ATCC PTA-10831 and ATCC PTA-10832, deposited with the ATCC on Apr. 16, 2010. In some embodiments, the isolated strain of pathogenic *Escherichia coli* is either ATCC PTA-10831 and ATCC PTA-10832, deposited with the ATCC on Apr. 16, 2010.

In some embodiments, the present invention provides compositions comprising cells, cell lysates or cell derivatives of one or more of the foregoing isolated strains of pathogenic *Escherichia coli* according to a first pharmaceutically acceptable carrier. In some embodiments, the first pharmaceutically acceptable carrier is an adjuvant. In some embodiments, the composition further comprises a second pharmaceutically acceptable carrier. In some embodiments, the cells are inactivated. In some embodiments, the cells are attenuated. In some embodiments, the strain(s) of pathogenic *Escherichia coli* is genetically distinct as determined by an analysis of DNA or RNA from the strain. In some embodiments, the analysis is by PCR fingerprinting, analysis of ribosomal RNA, or analysis of DNA polymorphisms. In some embodiments, the composition comprises an amount of the cells, cell lysates or cell derivatives sufficient to elicit an immune response to the isolated strain of pathogenic *Escherichia coli*. In some embodiments, the composition comprises an amount of the cells, cell lysates or cell derivatives in an amount effective to induce sufficient titers of immunoglobulin molecules to reduce or prevent the incidence of uterine disease in said subject. In some embodiments, the cells, cell lysates or cell derivatives sufficient to elicit an immune response to the isolated strain of pathogenic *Escherichia coli* comprise from approximately $10^4$ cell equivalents to about $10^8$ cell equivalents. In some embodiments, the compositions comprise at least two isolated strains of pathogenic *Escherichia coli* that express fimH and at least one of astA, cdt, kpsII, ibeA, and hly and comprise a gyrB gene sequence at least 97% identical to one of SEQ ID NOs:3 and 4.

In some embodiments, the present invention provides methods of protecting or treating subject(s) comprising administering to the subject(s) one of the foregoing compositions. In some embodiments, the subject(s) are at risk of developing uterine disease or suffer from uterine disease. In some embodiments, the uterine disease is selected from the group consisting of puerperal metritis, clinical endometritis and subclinical endometritis. In some embodiments, the clinical incidence of at least one of puerperal metritis, clinical endometritis and subclinical endometritis in the subject(s) is reduced such that the number or percentage of subject(s) that show clinical puerperal metritis, clinical endometritis and/or subclinical endometritis is less after such administering than before such administering. In some embodiments, the subject is a bovine.

In some embodiments, the present invention relates to use of any of the foregoing compositions to treat a subject. In some embodiments, the subject(s) are at risk of developing uterine disease or suffer from uterine disease. In some embodiments, the subject is a bovine.

In further embodiments, the present invention provides bacteriophage preparations comprising at least one isolated bacteriophage preparation having lytic activity against one or more IUPEC strains, wherein the isolated bacteriophage is virulent and safe to administer to an animal. In some embodiments, the bacteriophage preparation further comprises a pharmaceutically acceptable carrier. In some embodiments, the preparation comprises at least 2, 3, or 4 isolated bacteriophage strains that are genetically distinct as demonstrated by restriction digests and have lytic activity against one or more IUPEC strains. In some embodiments, the at least one isolated bacteriophage preparation is selected from preparations 1230-10, 6375-10, 2540-4, and 6547-2 and combinations thereof. In some embodiments, the at least one isolated bacteriophage preparation is selected from preparations having the characteristics of preparations 1230-10, 6375-10, 2540-4, and 6547-2 and combinations thereof. In some embodiments, the preparation is a food product, a nutritional composition, a food supplement or a pharmaceutical composition. In some embodiments, the preparation is a uterine bolus. In some embodiments, the preparation is a uterine infusate. In some embodiments, the bacteriophage preparation is in an amount of at least $10^2$ plaque forming units per milliliter or gram.

In some embodiments, the present invention provides methods for treating uterine disease comprising administering to a subject an effective amount of a bacteriophage preparation to prevent or treat the infection, the bacteriophage preparation comprising at least one isolated bacteriophage having lytic activity against one or more IUPEC strains and a pharmaceutically acceptable carrier. In some embodiments, the uterine infection is selected from the group consisting of puerperal metritis, clinical endometritis and subclinical endometritis. In some embodiments, the subject is a bovine. In some embodiments, the effective amount is at least $10^4$ plaque forming units per milliliter or gram. In some embodiments, the preparation is one of the foregoing preparations. In some embodiments, the at least one isolated bacteriophage is selected from strains 1230-10, 6375-10, 2540-4, and 6547-2 and combinations thereof. In some embodiments, the preparation is a cocktail of at least two isolated bacteriophages. In some embodiments, the preparation is a cocktail of at least four isolated bacteriophages. In some embodiments, the at least four isolated bacteriophages comprise strains 1230-10, 6375-10, 2540-4, and 6547-2. In some embodiments, each of the strains is provided in an amount of at least $10^2$ plaque forming units per milliliter or gram.

In some embodiments, the present invention relates to use of any of the foregoing compositions to treat a subject. In some embodiments, the subject(s) are at risk of developing uterine disease or suffer from uterine disease. In some embodiments, the subject is a bovine.

In some embodiments, the present invention provides methods of treating or preventing uterine disease in a subject comprising: administering to the subject a vaccine composition comprising an antigenic fragment of a type 1 adhesin and an adjuvant, the composition provided in an amount effective to induce sufficient titers of immunoglobulin molecules to reduce or prevent the incidence of uterine disease in the subject. In some embodiments, the type 1 adhesin is fimH. In some embodiments, the composition comprises fimH and fimC. In some embodiments, the fimH and fimC are provided in approximately an equimolar ratio. In some embodiments, the subject is a bovine. In some embodiments, the present invention relates to use of any of the foregoing compositions to treat a subject. In some embodiments, the subject(s) are at risk of developing uterine disease or suffer from uterine disease.

In some embodiments, the present invention provides methods of treating or preventing uterine disease in a subject comprising: administering to the subject a composition comprising high-mannose oligosaccharide, the oligosaccharide having more than 6 mannose residues, in an amount effective to reduce or prevent the incidence of uterine disease in the subject. In some embodiments, the composition further comprises a pharmaceutically acceptable carrier. In some embodiments, the composition is supplied as uterine bolus or infusate. In some embodiments, the subject is a bovine. In some embodiments, the present invention relates to use of any of the foregoing compositions to treat a subject. In some embodiments, the subject(s) are at risk of developing uterine disease or suffer from uterine disease.

DESCRIPTION OF THE FIGURES

FIG. 13: SEQ ID NO:3.

FIG. 14: SEQ ID NO:4

DEFINITIONS

Figure 1:
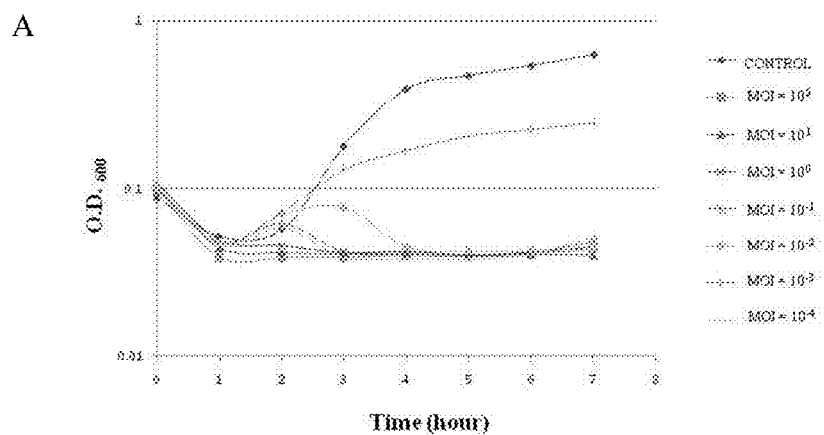
FIG. 1A-K. Graphs showing inimum inhibitory multiplicity of infection (miMOI) for various phage preparations.
Figure 1:
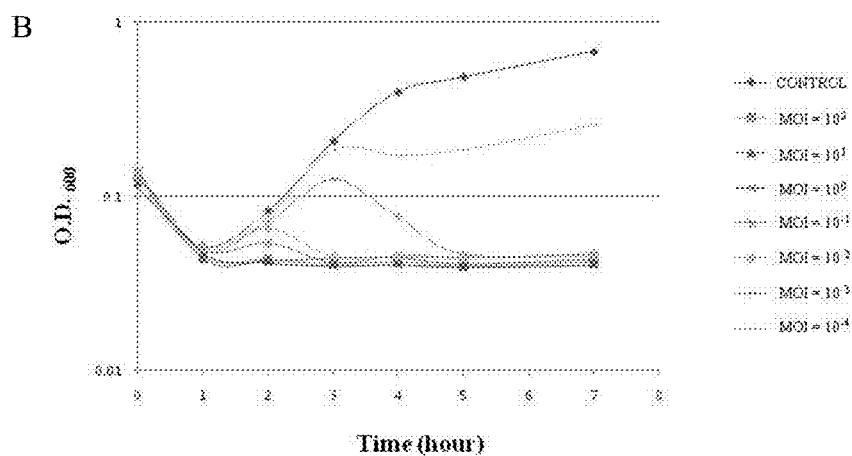
Figure 1:
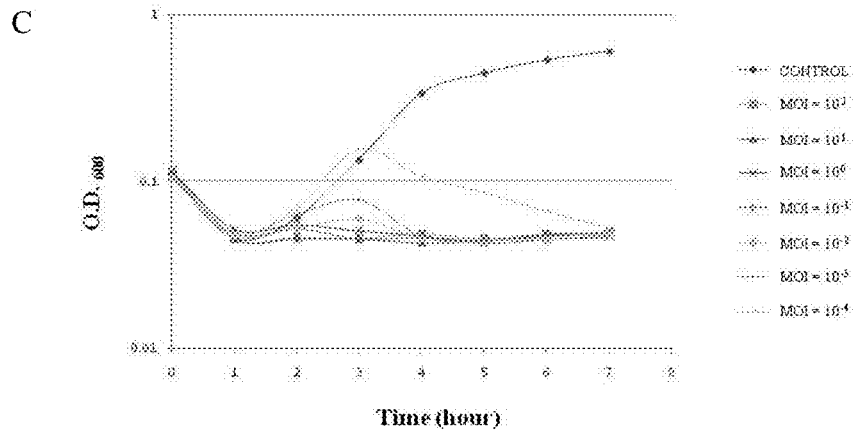
Figure 1:
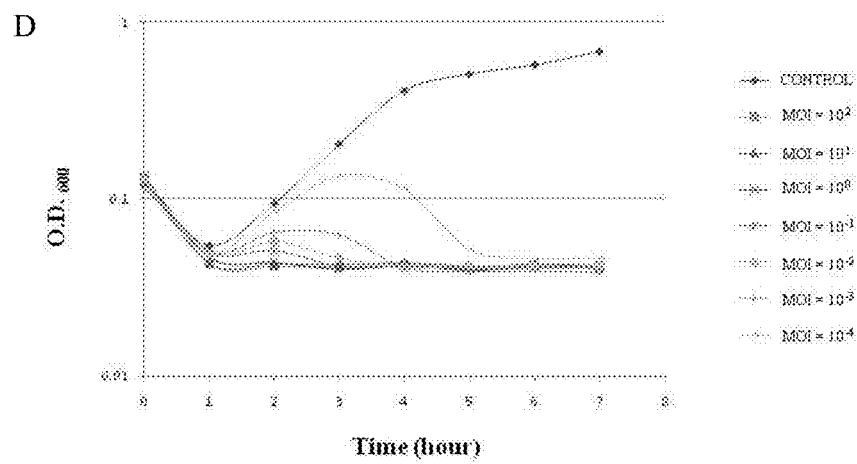
Figure 1:
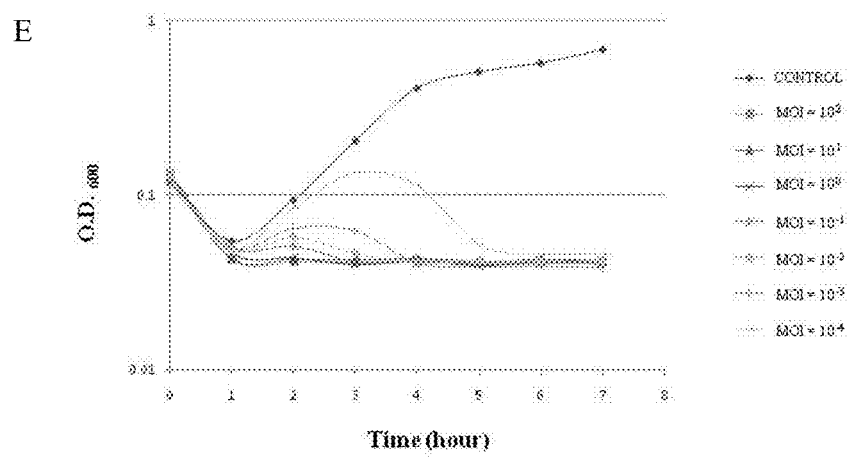
Figure 1:
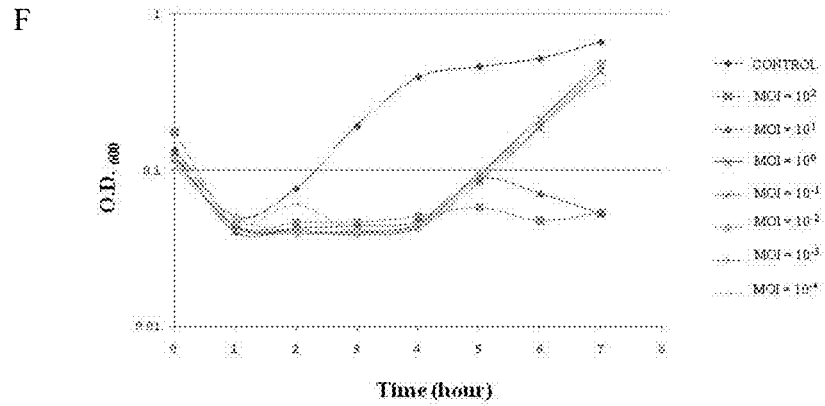
Figure 1:
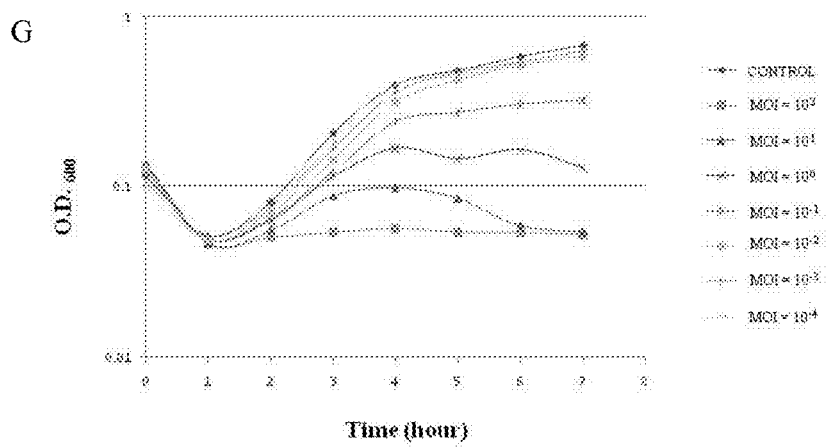
Figure 1:
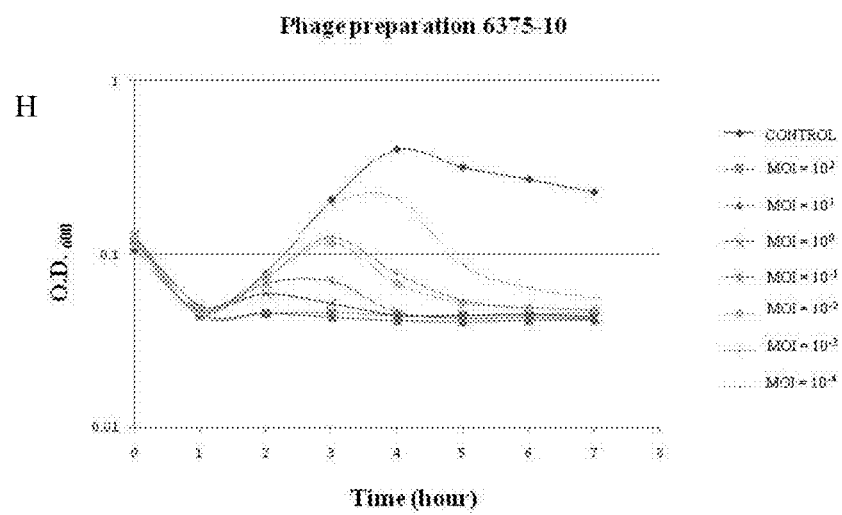
Figure 1:
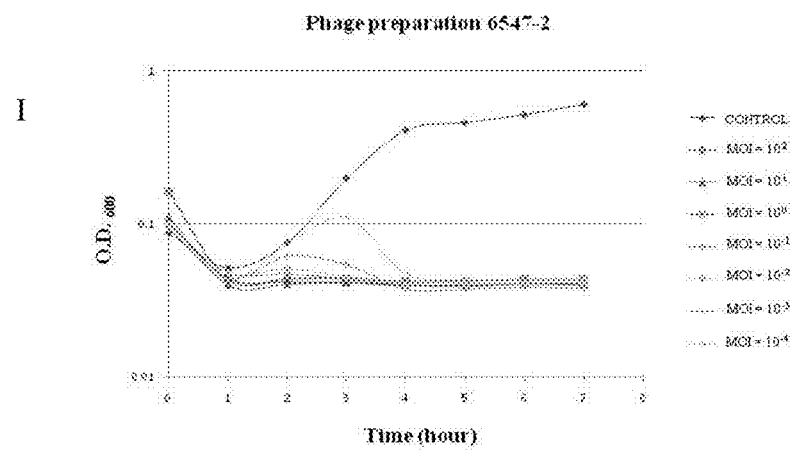
Figure 1:
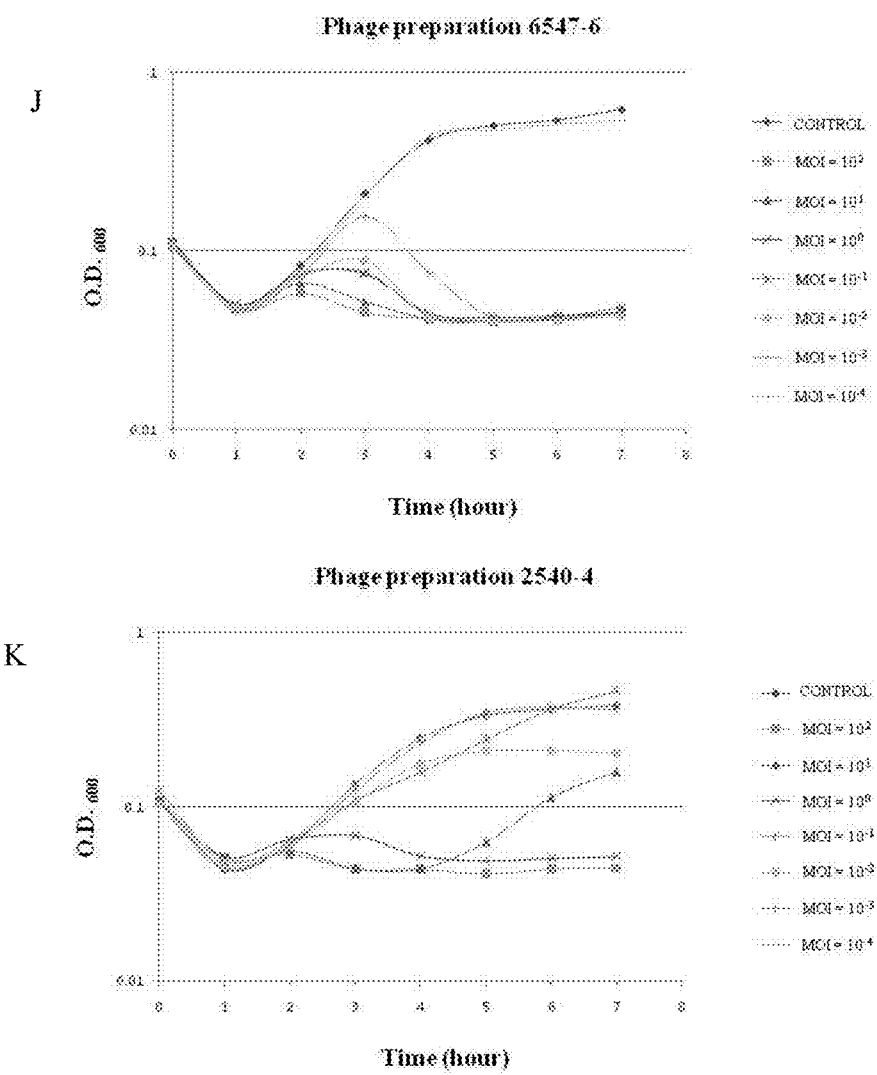

As used throughout the specification and in the claims, "a," "an" or "the" can mean one or more, depending upon the context in which it is used.

The term "Intrauterine Pathogenic *Escherichia coli* (IUPEC)" refers to strains of *E. coli* that are isolated from the uterus of an animal, such as a cow, and express virulence factor fimH as well as one or more of the virulence factors astA, cdt, kpsII, ibeA, and hly.

The term "pathotype" refers to a pathogen distinguished from others of the species by its pathogenicity on a specific host(s). For example, the present invention discloses pathotypes of *E. coli* (i.e, IUPEC) that are pathogenic in the uterus of an animal. In some embodiments, these pathotypes can be distinguished by one or more characteristics, such as ribosomal RNA sequence variation, DNA polymorphisms, or presence or absence of virulence factor genes (see e.g., Sambrook et al., Molecular Cloning: A Laboratory Manual, 2nd Ed., Cold Spring Harbor Laboratory, Cold Spring Harbor, N.Y., 1989; DNA cloning: A Practical Approach, Volumes I and II, Glover, D. M. ed., IRL Press Limited, Oxford, 1985; Harlow and Lane, Antibodies, A Laboratory Manual, Cold Spring Harbor Publications, N.Y. (1988)).

The term "virulence factor" refers to molecules expressed by pathogens (e.g., IUPEC) that enable a microorganism to establish itself on or within a host of a particular species and enhance its potential to cause disease. For example, virulence factors can allow the pathogen to achieve the following: colonization of a niche in the host (such as adhesion to cells); evasion of the host's immune response; entry into and exit out of cells (if the pathogen is an intracellular one); and obtain nutrition from the host. A "virulence factor gene" is a gene that encodes a virulence factor.

The term "inactivated," also referred to as "killed," means that the microorganisms (e.g., IUPEC) are treated by any of several means known to the art so that they no longer grow or reproduce, but that the microorganisms are still capable of eliciting an immune response in the target animal. Examples of inactivating agents are: formalin, azide, freeze-thaw, sonication, heat treatment, sudden pressure drop, detergent (especially non-ionic detergents), lysozyme, phenyl, proteolytic enzymes, propiolactone, Thimerosal (see U.S. Pat. No. 5,338,543 Fitzgerald, et al.), and binary ethyleneimine (see U.S. Pat. No. 5,565,205 Petersen, et al.).

The term "attenuated," also referred to as "modified live," is intended to refer to a living IUPEC pathotype which has been attenuated (modified) by any of a number of methods known in the art including, but not limited to, multiple serial passage, temperature sensitive attenuation, mutation, or the like such that the resultant strain is relatively non-pathogenic to a bovine species. The modified live strain should be capable of limited replication in the vaccinated animal and of inducing a protective immune response which is protective against disease caused by virulent or wild-type IUPEC.

The term "pharmaceutically acceptable" means a material that is not biologically or otherwise undesirable, i.e., the material may be administered to an animal along with immunogenic material (e.g., inactivated or attenuated IUPEC pathotypes) or bacteriophages without causing any undesirable biological effects or interacting in a deleterious manner with any of the other components of the vaccine in which it is contained. Examples of such pharmaceutically acceptable excipients include water and physiological saline (for further examples, see Arnon, R. (Ed.) Synthetic Vaccines 1:83-92, CRC Press, Inc., Boca Raton, Fla., 1987).

The term "adjuvant" means a potentiator or enhancer of the immune response.

The term "suitable" is meant to include any substance which can be used in combination with the vaccine immunogen (i.e. inactivated or attenuated IUPEC strains or fractions thereof) to augment the immune response, without producing adverse reactions in the vaccinated animal.

The term "immunogenic amount" means an amount of an immunogen, i.e. the inactivated or attenuated IUPEC strain(s) or a portion thereof, which is sufficient to induce an immune response in a vaccinated bovine species and which protects the animal against disease caused by wild-type or virulent IUPEC upon exposure thereto or which has a commercially beneficial effect that lessens the effect of IUPEC on milk production or animal health.

The term "cell equivalent" means an amount of inactivated cells or other immunogenic material (such as a cell lysate or fraction of a cell lysate) that is produced from a particular amount of cells.

DETAILED DESCRIPTION OF THE INVENTION

The present invention relates to methods and compositions for preventing and treating uterine disease, and in particular to vaccines and bacteriophage compositions for treating or preventing puerperal metritis, clinical endometritis and/or subclinical endometritis. In some embodiments, the present invention provides isolated IUPEC strains and vaccines prepared from these strains. In other embodiments, the present invention provides bacteriophage compositions. The vaccines and bacteriophage compositions find use in treating and preventing uterine disease.

1. IUPEC Strains

In some embodiments, the present invention provides isolated IUPEC strains. The isolated strains are preferably prepared from uterine samples taken from a subject. In some preferred embodiments, the subject animal is a bovine. In some embodiments, the strains are isolated from uterine swabs taken from a subject that is exhibiting symptoms of uterine infection. Symptoms of metritis include, but are not limited to, presence of fetid watery red-brown uterine discharge, associated with systemic signs of illness, and rectal temperature greater than 39.5° C. In some embodiments, clinical endometritis is diagnosed by the presence of purulent or mucopurulent discharge, by retrieving vaginal mucus using the Metricheck device (Metricheck, SimcroTech, Hamilton, New Zealand). In some embodiments, the uterine swab is obtained as follows. The subject (e.g., a cow) is restrained and the perineum area is cleansed and disinfected with a 70% ethyl alcohol solution. A sterile swab covered by a sterile pipette (e.g., inside a plastic sheath) is introduced to the cranial vagina. The pipette is manipulated through the cervix into the uterus. There the sheath is ruptured, and the swab exposed to uterine secretion. The swab is pulled inside the pipette and kept in a transportation media at 4° C. until further processing in the laboratory. In some embodiments, the uterine swabs are cultured aerobically on MacConkey agar (Difco) at 37° C. E. coli colonies are distinguished by a purple-red color. E. coli colonies from the MacConkey agar cultures are picked and subsequently streaked on CHROMagar-E. coli for isolation and further identification of E. coli species.

In some embodiments, isolated IUPEC strains are identified by genetic analysis. Suitable genetic analysis techniques include, but are not limited to: Polymerase Chain Reaction (PCR) analysis of ribosomal RNA; analysis of randomly amplified polymorphic DNA ((RAPD)-PCR); triplex PCR for genes chuA and yjaA and an anonymous DNA fragment; multiplex cdtB PCR; multiplex PCR for genes related to diarrheagenic E. coli; and DNA gyrase (gryB) amplification and sequencing. In some embodiments, a combination of two or more of these techniques are utilized to identify the desired IUPEC strains.

In some embodiments, the isolated IUPEC strains are positive for the virulence factor fimH and one or more of virulence factors astA, cdt, kpsII, ibeA, and hly. In some embodiments, the isolated strains are genetically distinct as demonstrated by DNA fingerprinting, preferably by RAPD-PCR analysis. Other fingerprinting methods known in the art may also be used to demonstrate genetic distinctness of the strains. Accordingly, in some embodiments, the isolated IUPEC strains are genetically distinct from other E. coli strains as determined by DNA fingerprinting. In some embodiments, the isolated IUPEC strains belong to one of the phlyogenetic groups A, B1, B2 or D as determined by triplex PCR for chuA and yjaA and an anonymous DNA fragment. In some embodiments, the isolated IUPEC strains are genetically distinct based on the gyrB gene sequence, preferably by using sequencing primers UP1S (5'-GAAGTCATCATGACCGTTCTGCA-3' (SEQ ID NO:1)) and UP2Sr (5'-AGCAGGGTACGGATGTGCGAGCC-3' (SEQ ID NO:2)). In some embodiments, genetic distinctness of the isolated IUPEC strains is based on a combination of these factors. In some embodiments, the IUPEC strains of the present invention have a gyrB sequence that is at least 97%, 98%, 99%, or 99.5% identical to one of SEQ ID NOs: 3 or 4. SEQ ID NOs: 3 and 4 are PCR amplification products of the primers corresponding to SEQ ID NOs: 1 and 2. SEQ ID NOs 3 and 4 are derived from the strains designated IUPEC (cdt, ibeA, fimH, kpsII, fyfA, traT, rpa, aerJ) and IUPEC (asta, fimH, fyfA, sfa) in FIG. 12. In some embodiments, the IUPEC strains of the present invention have a gyrB sequence that is at least 97%, 98%, 99%, or 99.5% identical to one of SEQ ID NOs: 3 or 4 and are positive for the virulence factor fimH and one or more of virulence factors astA, cdt, kpsII, ibeA, and hly.

The present invention is not limited to any particular isolated IUPEC strain. Exemplary IUPEC strains of the present invention are described in FIG. 12. These strains are designated as IUPEC with one or more specific virulence factors. In some embodiments, the IUPEC strains of the present invention have the characteristics of one or more of strains ATCC PTA-10831 and ATCC PTA-10832 deposited with the ATCC on Apr. 16, 2010. In some embodiments, these characteristics include, but are not limited to: positive for the virulence factor fimH and one or more of virulence factors astA, cdt, kpsII, ibeA, and hly; production of an immune response in a subject into which a vaccine comprising the isolated strain(s) has been introduced sufficient to prevent uterine disease in the subject; and a gyrB sequence that is at least 97%, 98%, 99%, or 99.5% identical to one of SEQ ID NOs: 3 and 4.

2. Vaccines

The invention disclosed herein is based in part on the discovery that uterine disease in the field is initiated by infection with various IUPEC strains. The vaccines of the present invention preferably comprise immunogenic material from one or more IUPEC strains. In some embodiments, the vaccines comprise an antigen derived from an IUPEC strain. In some embodiments, the vaccine comprises antigens derived from two or more IUPEC strains. In a further specific embodiment, the vaccine comprises inactivated or attenuated IUPEC strains such as those identified in FIG. 12. In a further specific embodiment, the vaccine comprises at least two inactivated or attenuated IUPEC strains. In a further specific embodiment, the vaccine comprises at least one inactivated or attenuated IUPEC strain with antigen derived from another pathogen.

It is anticipated that additional IUPEC strains may emerge and may be isolated with continued animal production. Additional IUPEC strains can be added to the vaccine as needed. Cultures of IUPEC can be isolated and typed as described herein. Vaccines can be formulated based on the prevalence of IUPEC strains present in the environment. Autogenous vaccines, i.e. those vaccines for use on the farm where the microorganisms are isolated, can be custom-designed to contain all IUPEC strains found on the farm. Vaccines developed for use by a mass market, i.e. those vaccines produced for general use on many different farms containing pre-selected IUPEC strains, can also be developed, marketed and used.

In some embodiments, this invention provides a vaccine comprising cells, cell lysates or cell derivatives of a single, inactivated or attenuated IUPEC strain, a pharmaceutically acceptable excipient and/or suitable adjuvant. In some embodiments, the vaccine contains mixtures of cells, cell lysates or cell derivatives of inactivated or attenuated IUPEC strains and may further contain antigens from other pathogens. The cells, cell lysates or cell derivatives may be produced by serial in vitro culture or be produced from IUPEC strains that are freshly isolated from infected animals or from cryopreserved cultures freshly prepared from infected animals.

Various physical and chemical methods of bacterial inactivation are known in the art. Examples of physical inactivation are UV-radiation, X-ray radiation, gamma-radiation and heating. Examples of inactivating chemicals are beta-propiolactone, glutaraldehyde, beta-ethyleneimine and formaldehyde.

In some embodiments, the attenuated vaccines of this invention are produced from cultures of IUPEC strains which have been treated so as to retain a limited ability to replicate within the vaccinated animal, but which does not retain the ability to infect other animals and cause uterine-related disease. The preparation and use of attenuated vaccines is well-known to practitioners of ordinary skill in the art.

The inactivated or attenuated IUPEC strain(s) may be further processed to fractionate and/or standardize the antigenic mass. For example, specific IUPEC strains might be isolated from samples and combined to form specific combinations of IUPEC strains in specific ratios. Similarly, components from a specific inactivated or attenuated IUPEC strain might be fractionated and a subset of those fractions combined with similarly fractionated components of another IUPEC strain to standardize the antigenic component of the vaccine preparation and to optimize its efficacy. In one embodiment, the antigenic components derived from a single IUPEC strain are enriched by removing non-immunogenic components from the cells of the strain. In another embodiment, the vaccine preparations are standardized to provide a required minimum cell content per formulated dose. In a preferred embodiment, the vaccine comprising inactivated IUPEC strains is formulated to deliver at least $10^3$, $10^4$, $10^5$, $10^6$, $10^7$, or $10^8$ cell equivalents of each IUPEC strain per dose. A complete vaccination of a bovine species comprises the administration of recommended doses. In a preferred embodiment, two such doses will be administered. In a further preferred embodiment, three such doses will be administered. It is understood by those skilled in the art that the critical value in describing a vaccination dose is the total amount of immunogen needed to elicit a protective response by the host animal to infectious disease caused by virulent or wild-type IUPEC. The number and volume of doses used can be varied and are determined by the practitioner based on costs and the need to avoid deleterious side effects in the animal caused by the administration. For example, the volume of one administration typically does not exceed 2-5 milliliters. The number of doses of inactivated vaccine needed in adult animals is typically one initial dose followed by 1-2 additional doses and annual revaccination. The number of doses of attenuated vaccine in adult animals is one initial dose followed by a booster. Subsequently, annual boosters are administered.

The vaccines of the present invention may further comprise antigenic material of other viruses and/or microorganisms known to be bovine pathogens, including, but not limited to, attenuated (modified-live) or inactivated viruses or microorganisms. Such combination vaccines provide protection against a plurality of diseases to which the bovine species are exposed, including but not limited to immunogenic compositions for *Staphylococcus aureus, Pasteurella hemolytica, Pasteurella multocida, Hemophilus somnus*, Bovine Respiratory Syncytial Virus, Bovine Diarrhea Virus, *E. coli* and Infectious Bovine Rhinotrachial Disease.

In other embodiments, the vaccine of this invention further comprises a suitable adjuvant. Effective amounts of a specific adjuvant may be readily determined so as to optimize the potentiation effect of the adjuvant on the immune response of an animal vaccinated. In some embodiments, suitable adjuvants can be chosen from the following group: mineral, vegetable or fish oil with water emulsions, aluminum hydroxide solutions, incomplete Freund's adjuvant, *E. coli* J5, dextran sulfate, iron oxide, sodium alginate, Bacto-Adjuvant, certain synthetic polymers such as Carbopol (BF Goodrich Company, Cleveland, Ohio), polyamino acids and co-polymers of amino acids, saponin, carrageenan, REGRESSIN (Vetrepharm, Athens, Ga.), AVRIDINE (N,N-dioctadecyl-N',N'-bis(2-hydroxyethyl)-propanediamine), long chain polydispersed β(1,4) linked mannan polymers interspersed with O-acetylated groups (e.g. ACEMANNAN), deproteinized highly purified cell wall extracts derived from non-pathogenic strain of *Mycobacterium* species (e.g. EQUIMUNE, Vetrepharm Research Inc., Athens Ga.), Mannite monooleate, paraffin oil, and muramyl dipeptide.

In some embodiments, the vaccine is formulated for delivery to a mucosal surface, such as the vagina. Suitable mucosal delivery systems include, but are not limited to: liposomes, immunostimulating complexes (ISCOMs) and cochleates; different types of biodegradable particles based on starch or copolymers of lactic and glycolic acid; and different mucosa-binding proteins, including both classical plant lectins and bacterial proteins such as the binding subunit portions of cholera toxin or *E. coli* heat-labile enterotoxin, to which antigens have been linked either chemically or as gene fusion proteins.

In another aspect, this invention discloses a method for immunizing bovine animals against uterine disease caused by IUPEC comprising administering to a bovine animal immunogenic amounts of inactivated or attentuated IUPEC strains to elicit a protective immune response by the animal. Preferably, the method comprises administering one or more inactivated or attenuated IUPEC strains to elicit a protective immune response by the animal. Immunization may be performed orally, intravaginally, intranasally, intratracheally, intramuscularly, intramammarily, subcutaneously, intravenously, or intradermally. The vaccine containing the inactivated or attenuated IUPEC strains can be administered by injection, by inhalation, by ingestion, or by infusion. Repeated doses of the vaccine preparations, i.e. "boosters", are preferable at periodic time intervals to enhance the immune response initially or after a long period of time since the last dose. The time interval between vaccinations varies depending on the age and condition of the animal. For lactating and adult animals, the first vaccination is preferably given at the end of the lactation cycle (i.e. "dry-off"), followed by a "booster" dose 2-4 weeks later, and preferably followed by a second booster dose 2-4 weeks thereafter. Newborn calves are preferably vaccinated at birth, followed by booster doses every 3-5 weeks until the calves are 4-6 months old and annually thereafter.

Subjects are vaccinated by introducing an immunogenic amount of one or more IUPEC strains into a subject. In some embodiments, bovine animals are immunized by administering at least approximately $10^8$ IUPEC cell equivalents of each inactivated biotype in the vaccine. In some embodiments, animals are immunized by administering at least approximately $10^3$, $10^4$, $10^5$, $10^6$, $10^7$, or $10^8$ cell equivalents, which have been inactivated, in at least two injections.

In another aspect, this invention discloses a method for producing an IUPEC vaccine comprising contacting at least one IUPEC strain with an inactivating material and incorporating the inactivated IUPEC cells into a pharmaceutically acceptable excipient with a suitable adjuvant to produce an IUPEC vaccine. In some embodiments, one or more selected IUPEC strains are grown separately as pure cultures, free of contamination by viruses, bacteria or any other microbial agent, including other IUPEC strains, to the desired cell equivalents, inactivated as described herein, and then combined in equal amounts with a pharmaceutically acceptable excipient to produce a vaccine. Alternatively, the IUPEC strains can be grown together as a mixed culture to the desired cell equivalents, inactivated and then, optionally, combined with a pharmaceutically acceptable excipient and a suitable adjuvant to produce an IUPEC vaccine. In some embodiments, the inactivated or attenuated IUPEC cells are mixed with a suitable adjuvant.

3. Bacteriophage Compositions

The present invention provides bacteriophage preparations for the treatment and prevention of disease in subjects. In some embodiments, the disease is a uterine disease such as puerperal metritis, clinical endometritis and subclinical endometritis. In some embodiments, the bacteriophage preparations have lytic activity against one or strains of *E. coli*. In some preferred embodiments, the bacteriophage preparations have lytic activity against one or more IUPEC strains.

The present invention is not limited to particular bacteriophage preparations. In some embodiments, the bacteriophage preparations are prepared from field-sources of bacteriophages. For example, bacteriophage preparations of the present invention can be isolated from manure lagoons on dairy or beef farms. In some embodiments, samples are taken from manure lagoons and centrifuged for 25 minutes at 3,000×g at 4° C. The supernatant is collected and filter-sterilized using a 0.22-µm-pore-size filter. The presence of lytic activity can be confirmed by contacting *E. coli* cultures, for example cultures of IUPEC strains, with the supernatant. Bacteriophage preparations that have lytic activity are further propagated in SM buffer (100 mM NaCl, 8 mM MgSO$_4$, 1 M Tris-HCl, pH 7.5) and prepared according to Sambrook and Russell (2001) for each bacteriophage solution (Sambrook and Russell, 2001). In some embodiments, the bacteriophage preparations are single-plaque isolated and propagated on a suitable host strain. 0.2% inoculum of an overnight culture of the propagating host strain was added in 250 ml of LB broth (Difco™) and incubated at 37° C. for 5 hours with shaking Approximately 1×10$^9$ PFU of each isolated bacteriophage is added to the culture and, after incubation at 37° C. for 20 minutes without shaking, the samples were incubated for a further 18-20 hours at 37° C. with vigorous shaking Lysis of the cultures is generally highly visible as evidenced by bacterial debris. In some embodiments, concentrated phage preparations are prepared by NaCl/Poly Ethylene Glycol (PEG) 8000 precipitation of LB lysates in accordance with protocols described by Sambrook and Russell (2001). Solid NaCl (final concentration 1.0 M) is added to each sample and after stirring, the samples were maintained on ice for 1 hour. The samples are centrifuged at 11,000×g at 4° C. for 10 minutes to remove debris and the supernatants (LB lysates) were transferred to sterile flasks. Solid PEG 8000 (final concentration 10% w/v) is added to the lysates and the samples are kept on ice for at least 1 hour to allow the bacteriophage particles to precipitate. Precipitated bacteriophages particles were recovered by centrifugation at 11,000×g at 4° C. for 10 minutes and resuspended in SM buffer. These large-scale high-titer lysates concentrated stocks are preferably stored at 4° C. In some embodiments, high-titer stocks for desired bacteriophage preparations are prepared in SM buffer (100 mM NaCl, 8 mM MgSO$_4$, 1 M Tris-HCl, pH 7.5) by the plate lysate method according to Sambrook and Russell, 2001. To remove debris, the lysate obtained from the top agar were pooled and centrifuged at 10,000×g at 4° C. for 10 minutes and the supernatant was sterilized by filtering through a 0.22-µm-pore-size filter. These high titer stocks were used to compound the cocktail and determine the minimum inhibitory Multiplicity of Infection (MOI) of bacteriophage particles.

The foregoing processes can be utilized to provide bacteriophage preparations in accordance with the present invention. In some embodiments, the bacteriophage preparations have lytic activity against one or more strains of *E. coli*, and in some preferred embodiments to one or more IUPEC strains. In some embodiments, the bacteriophage preparations of the present invention comprise about 10 to about 10$^{10}$ plaque forming units (PFU) per milliliter. In some embodiments, the bacteriophage preparations of the present invention comprise one or more genetically distinct phage preparations. In some embodiments, the phage preparations comprise one or more of preparations 1230-10, 6375-10, 2540-4, and 6547-2. In some embodiments, the phage preparations of the present inventions have the characteristics of these deposited (Are you referring to ATCC deposits here? We will not be deposting these phages, as we discussed) phage preparations.

Pharmaceutical compositions according to the present invention can be prepared by admixing a quantity of a bacteriophage preparation with a pharmaceutically acceptable carrier. The preferred delivery vehicles for the bacteriophages are in aqueous suspension, in a tablet or capsule form, as a powder or coating, or incorporated on or in material that can be eaten. However, as will be appreciated by one knowledgeable in the art, any suitable preparation which allows delivery of the bacteriophage into the gastrointestinal tract of the animal is within the scope of the invention. For examples of suitable carriers, diluents, excipients and the like, see Remington: The Science and Practice of Pharmacy, 2000, Gennaro, Ariz. ed., Eaton, Pa.: Mack Publishing Co. A typical composition for such purpose comprises a pharmaceutically acceptable carrier. For instance, the composition may contain about 0.1 to 10$^{10}$ PFU of the bacteriophage preparation per milliliter or gram, or any range of concentration derivable therein.

Alternatively, the bacteriophage pharmaceutical preparations of the present invention can be in the form of liposomes, lipophilic microcapsules, dendrimers or the like for oral administration to treat systemic infections. Those skilled in the art are capable of preparing the bacteriophage compositions of the present invention in the form of a lipophilic microcapsule, a dendrimer or a liposome using conventional techniques known in the art. The skilled artisan also is capable of providing a bacteriophage composition that can be administered intranasally, rectally, transdermally, topically, or other known routes of administration of medicaments. In particular embodiments, the bacteriophage composition is formulated for topical application to a subject.

The bacteriophage preparations of the present invention can be used to treat mammals having an infectious disease, such as a bacterial infection. For example, the mammal may be a horse, a cow, a pig, or a human. In particular embodiments, the mammal is a human with an infectious disease. The infectious disease may be any infectious disease amenable to treatment with a bacteriophage composition as set forth herein. For example, the disease may be uterine disease.

The bacteriophage preparations of the present invention preferably are administered in an amount and for a period of time effective to treat the bacterial infection. The expression "treating bacterial infections," as it is used throughout this description, denotes either (i) killing or obliterating sufficient bacterial microorganisms to render the microorganisms ineffective in infecting the host, or (ii) reducing a sufficient quantity of bacterial microorganisms so as to render the microorganisms more susceptible to either the immune system or treatment using conventional antibiotics. Determining an effective amount of host-specific, non-toxic purified bacteriophage composition to be administered in accordance with the present invention entails standard evaluations. An assessment in this regard would generate data concerning bioavailability, absorption, metabolism, serum and tissue levels and excretion, as well as microorganism levels, markers, and cultures. The appropriate dosage and duration of treatment can be ascertained by those skilled in the art using known techniques.

According to one embodiment, bacteriophage preparations according to the present invention can be used to reduce but not entirely obliterate the population of harmful microorganisms, thereby rendering the infectious focus more susceptible to chemotherapeutic antibiotics and thus reducing, in combination therapy duration, side effects, and risks of the latter. Thus, the bacteriophage pharmaceutical preparations of the present invention can be used in combination with known antibiotics such as aminoglycosides, cephalosporins, macrolides, erythromycin, monobactams, penicillins, quinolones, sulfonamides, tetracycline, and various other anti-infective agents. Those skilled in the art can refer to the Physician's Desk Reference, 50.sup.th Ed. (1996), or similar reference manuals for a more complete listing of known antibiotics which could be used in combination with the bacteriophage compositions.

In some embodiments, the bacteriophage preparations of the present invention are dried. The dried preparation can be applied or administered to an organism in a dried form, or it can be reformulated in a carrier prior to administration. Such dried preparations simplify storage and shipping.

Certain embodiments of the present invention provide for the administration or application of one or more secondary forms of therapies for the treatment or prevention of an infectious disease. The secondary form of therapy may be administration of one or more secondary pharmacological agents that can be applied in the treatment or prevention of an infectious disease. If the secondary therapy is a pharmacological agent, it may be administered prior to, concurrently, or following administration of the bacteriophage-containing composition.

Examples of secondary therapy include antibiotics, such as penicillins (including aminopenicillins and/or penicillinas in conjunction with penicillinase inhibitor and anti-fungal agents), cephalosporins (and the closely related cephamycins and carbapenems), fluoroquinolones, tetracyclines, macrolides, aminoglycosides. Specific examples include, but are not limited to, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithromycin, trimethoprim sulfate and bacitracin.

The interval between the bacteriophage therapy and the secondary therapy may be any interval as determined by those of ordinary skill in the art. For example, the interval may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations. In some embodiments, the timing of administration of a secondary therapeutic agent is determined based on the response of the subject to the bacteriophage therapy.

4. Diagnostics

Selected IUPEC strains may be used as the basis for diagnostic tools to detect the presence of IUPEC. In one aspect of this invention, samples from cattle would be tested for the presence of antibodies specific for IUPEC by contacting the samples with IUPEC cells or antigens derived from IUPEC. Examples of technologies that could be adapted to such a method include, but are not limited to, RIA, ELISA and immunoblot. Examples of specific embodiments would include antigens derived from one or more IUPEC strains. In another embodiment, antibodies-raised against IUPEC strains or antigens-derived from selected IUPEC strains would be used to test for the presence of IUPEC.

5. Other Treatment and Prevention Methods

As described above and in the following examples, the present invention discloses that IUPEC strains that are characterized in being positive for the virulence factor fimH and at least one of virulence factors astA, cdt, kpsII, ibeA, and hly are involved in the development of uterine disease. Based on this novel finding, vaccines and other compositions that have been previously described for other uses find use for the treatment and prevention of uterine disease.

In some embodiments, the present invention provides methods of treating uterine disease by administration of a vaccine comprising one or more immunogenic FimH polypeptides. Vaccines useful in the present invention are described, for example, in U.S. Pat. No. 6,737,063 and U.S. Pat. Publ. 2005/0196408, the entire contents of each of which are herein incorporated by reference. In some embodiments, the vaccines comprise a combination of FimC and FimH, preferably in an equimolar ratio. For example, a preferred FimCH vaccine comprises an approximately 52 kDa complex composed of two proteins, FimC (22.8 kDa) and FimH (29.1 kDa) in a 1:1 equimolar ratio. In some embodiments, the FimCH complex is expressed from a pUC-based vector with two separate lac-inducible promoters driving expression of the FimC and FimH genes respectively. In some embodiments, the FimC and FimH genes used in the vector are derived from a well-characterized uropathogenic *E. coli* isolate J96. In some embodiments, the FimCH complex is produced in the periplasm of *E. coli* strain BL21 and is purified from periplasmic extracts by standard chromatographic methods. The FimCH protein can be formulated in a number of different buffers compatible with its solubility profile including 20 mM HEPES (pH 7.0), PBS (pH 7.0), and 20 mM sodium citrate at pH 6.0 in 0.2 M NaCl. In some embodiments, sodium citrate formulation enhances stability of the FimCH complex and is also compatible with commonly used diluents as well as adjuvants, including the MF-59, MF-59C or MF-59C.1 adjuvant (Chiron, Emeryville, Calif.). Immunization may be performed orally, intravaginally, intranasally, intratracheally, intramuscularly, intramammarily, subcutaneously, intravenously, or intradermally. In some embodiments, the vaccine is formulated for delivery to a mucosal surface, such as the vagina. Suitable mucosal delivery systems include, but are not limited to: liposomes, immunostimulating complexes (ISCOMs) and cochleates; different types of biodegradable particles based on starch or copolymers of lactic and glycolic acid; and different mucosa-binding proteins, including both classical plant lectins and bacterial proteins such as the binding subunit portions of cholera toxin or E. coli heat-labile enterotoxin, to which antigens have been linked either chemically or as gene fusion proteins.

In other embodiments, the present invention provides methods for treating or preventing uterine disease through the use of agents that block the attachment of IUPEC strains to uterine tissues. Suitable compositions are described, for example, in U.S. Pat. No. 5,939,279, the entire contents of which are incorporated herein by reference. Accordingly, in some embodiments, the present invention provides methods of preventing or treating uterine disease in a subject comprising administering to the subject a composition comprising high-mannose oligosaccharide. In some embodiments, the oligosaccharide has more than 6 mannose residues. In some embodiments, the oligosaccharide is $Man_9(GlcNAc)_2$. In some embodiments, the high-mannose oligosaccharide is provided with a pharmaceutically acceptable carrier. In some embodiments, the composition is formulated as a uterine bolus or infusate.

EXPERIMENTAL

Example 1

Isolation and Lytic Activity Quantification of Bacteriophages

The objective of this study was to isolate bacteriophages from environmental samples of two large commercial dairy farms using wild strains of Escherichia coli as hosts. A total of 57 Escherichia coli were isolated from the uterus of postpartum Holstein dairy cows and phylogenetically grouped by triplex PCR. Additionally, 11 bacteriophage preparations were isolated from manure systems of commercial dairy farms and characterized for in vitro antimicrobial activity. Each bacterial host was inoculated with their respective bacteriophage preparation at several different multiplicities of infections (MOI) to determine minimum inhibitory MOI. The effect of a single dose (MOI=$10^2$) of bacteriophage on the growth curve or all 57 E. coli isolates was assessed using a microplate technique. Furthermore, genetic diversity within and between the different bacteriophage preparations was assessed by bacteriophage purification followed by DNA extraction, restriction, and agarose gel electrophoresis. Phylogenetic grouping based on triplex PCR showed that all isolates of E. coli belonged to phylogroup B1. Bacterial growth was completely inhibited at considerably low MOIs and the effect of a single dose (MOI=$10^2$) of bacteriophage preparations on the growth curve of all 57 E. coli isolates showed that all 11 bacteriophage preparations significantly decreased the growth rate of the isolates. Bacteriophage preparation 1230-10 had the strongest antimicrobial activity and completely inhibited the growth of 71.7% (n=57) of all isolates. The combined action of bacteriophage preparations 1230-10, 6375-10, 2540-4, and 6547-2 had the broadest spectrum of action and completely inhibited the growth (final $OD_{600}\leq0.1$) of 80% of the E. coli isolates and considerably inhibited the growth (final $OD_{600}\leq0.2$) of 90% of the E. coli isolates. Restriction profile analysis demonstrated that all four phage preparations contained bacteriophages that were genetically distinct from each other based on the banding pattern of the fragments. The combination of several different bacteriophages can improve the spectrum of action and the results of this study suggested that bacteriophages 1230-10, 6375-10, 2540-4, and 6547-2 should be used in combination as a cocktail.

Material and Methods

Farm, Management, and Sample Collection

Uterine lavage was performed on 5 postpartum dairy cows that were housed in a commercial dairy farm located near Ithaca N.Y. Samples were collected from $1^{st}$ until the $15^{th}$ Oct. 2008. This farm was selected because of its long history of a working relationship with the Ambulatory and Production Medicine Clinic at Cornell University. The farm milked 2,800 Holstein cows three times daily in a double 52 stalls parallel milking parlor. The cows were housed in free-stall barns with concrete stalls covered with mattresses and bedded with waste paper-pulp. All cows were offered a total mixed ration (TMR) consisting of approximately 55% forage (corn silage, haylage, and wheat straw) and 45% concentrate (corn meal, soybean meal, canola, cotton seed, and citrus pulp) on a dry matter basis of the diet. The diet was formulated to meet or exceed the NRC nutrients requirements for lactating Holstein cows weighing 650 kg and producing 45 kg of 3.5% fat corrected milk (FCM).

Uterine lavage was performed on a convenience sample of 5 postpartum dairy cows, the average days in milk (DIM) at sampling was 5±2 DIM. To isolate E. coli from uterus a uterine secretion sample was collected as follows: cows were restrained and the perineum area was cleansed and disinfected with a 70% ethyl alcohol solution, a plastic infusion pipette (inside a plastic sheath) was introduced to the cranial vagina. There the sheath was ruptured, and the clean pipette tip was manipulated through the cervix into the uterus. A total of 40 ml of sterile saline solution was injected into the uterus, agitated gently, and a sample of the fluid aspirated. The volume of recovered fluid ranged from 5 to 15 ml. Samples were kept in ice until they were processed in the laboratory.

Bacterial Isolation

Uterine secretion was taken to the laboratory and diluted in 0.9% sodium chloride saline. The sample was cultured aerobically on MacConkey agar (Difco™) at 37° C. and E. coli colonies were distinguished by a purple-red color. Typical E. coli colonies were streaked on CHROMagar™ E. coli for confirmation and further isolation. Colonial morphology and characteristic appearance in smears stained by Gram's Method was used to exam purity. Additionally, identification of isolated strains was carried out by 16S ribosomal RNA (rRNA)-encoding gene amplification (Simpson K W et al., 2006). Phylogenetic grouping was performed by triplex PCR which uses a combination of two genes (chuA and yjaA) and an anonymous DNA fragment (Clermont et al., 2000). All isolates were stocked at −80° C. in Luria-Bertani (LB) broth containing 20% glycerol until further testing.

E. coli Bacteriophage Isolation, Preparation and Titration

To isolate bacteriophages a sewage sample of 500 ml from the manure lagoons of two large commercial dairy farms was taken. In the laboratory two samples were homogenize. A sub-sample of 50 ml was taken and centrifuged for 25 minutes at 3,000×g at 4° C. The supernatant was collected and filtered-sterilized using a 0.22-µm-pore-size filter.

Ten *E. coli* isolates were randomly selected from the total pool of 57 *E. coli* isolates to serve as target hosts for the bacteriophages. Additionally, one reference strain from the American Type of Culture Collection (ATCC) numbered 25404 was used as a host. Each of the 11 *E. coli* hosts were separately cultured in LB broth (Difco™) until an optical density (O.D.$_{600}$) of 0.3 (~1×10$^8$ CFU/ml) was reached. At this point, 8.8 ml of the sterile filtrated sewage was inoculated with 1 ml of 10×LB broth (Difco™) and 200 µL (~1×10$^8$ CFU/ml) of each one of the 11 *E. coli* hosts. The mixtures were then incubated at 37° C. for 18 hours with shaking to allow the amplification of the bacteriophages. After incubation the mixture was centrifuged at 10,000×g at 4° C. for 10 minutes and the supernatant was sterilized by filtering through a 0.22-µm-pore-size filter.

To test bacteriophage activity in the filtered supernatant a spot assay that entailed of placing 5 µL of the supernatant on LB agar (Difco™) previously seeded with *E. coli* was performed for each one of the 11 *E. coli* hosts. The inoculated plates were incubated for 18 hours at 37° C. and then checked for the presence of lytic zone.

After confirmation of phage activity, a high titer stock in SM buffer (100 mM NaCl, 8 mM MgSO$_4$, 1 M Tris-HCl, pH 7.5) was prepared according to Sambrook and Russel (2001) for each bacteriophage solution (Sambrook and Russell, 2001). These high titer stocks were used to determine the minimum inhibitory Multiplicity of Infection (MOI) of bacteriophage particles. Furthermore, the high titer stocks of bacteriophages were titrated using the standard soft agar overlay technique (Clokie and Kropinski, 2009).

Determination of the Minimum Inhibitory MOI

To assess the effect of inoculation of several ratios of bacteriophages and bacteria on the growth curve of each host *E. coli* isolate and determine the minimum inhibitory MOI, the following procedure was performed: *E. coli* isolates were grown in LB broth (Difco™) at 37° C. for 6-8 hours with shaking until an O.D.$_{600}$=0.3 (~1×10$^8$ CFU/ml) was reached. The cultures were then dilute in LB broth (Difco™) to 10$^5$ CFU/ml and an aliquot of 0.2 ml was then added to microplate wells that were previously prepared to contain from 10$^0$ to 10$^6$ PFU/well of the bacteriophage solutions. All tests were done in triplicate and two controls were used; a sterile control containing only LB broth (Difco™) and a positive control that contained the *E. coli* isolate inoculated in LB broth (Difco™) without any bacteriophages. The O.D.$_{600}$ was assessed in an hourly basis for a total of 10 hours. The minimum inhibitory MOI was arbitrarily estimated as the minimum ratio of bacteriophage and bacteria that completely inhibited growth of the cells at the second hour of the beginning of the stationary phase of the positive control.

Assessment of the Effect of a Single Dose (MOI=10$^2$) of Bacteriophage on the Growth Curve In this aspect of the study it was evaluated the susceptibility of all 57 *E. coli* isolates to the 11 different bacteriophage solutions. The *E. coli* isolates were grown in LB (Difco™) broth at 37° C. for 6-8 hours with shaking until an O.D.$_{600}$=0.3 (~1×10$^8$ CFU/ml) was reached. The cultures were then dilute in LB broth to 10$^5$ CFU/ml and an aliquot of 0.2 ml was then added to microplate wells that were previously prepared to contain a standard dose of 10$^6$ PFU of bacteriophage, which results in a ratio of 100 PFU of bacteriophage for 1 CFU of the *E. coli* isolate (MOI=10$^2$). All tests were done in triplicate and two controls were used; a sterile control containing only LB broth and a positive control that contained the *E. coli* isolate in LB broth without any bacteriophages. The OD$_{600}$ of the cultures was assessed on an hourly basis for a total of 12 hours and an additional reading was done 24 hours after inoculation.

Bacteriophage Propagation, Isolation and Concentration

To assess access the genetic diversity within and between the different bacteriophage preparations, bacteriophages were single-plaque isolated and propagated on their respective host strains, this technique was then repeated to warrant single bacteriophage isolation. Bacteriophages were propagated as follows: 0.2% inoculum of an overnight culture of the propagating host strain was added in 250 ml of LB broth (Difco™) and incubated at 37° C. for 5 hours with shaking Approximately 1×10$^9$ PFU of each isolated bacteriophage was added to the culture and, after incubation at 37° C. for 20 minutes without shaking, the samples were incubated for a further 18-20 hours at 37° C. with vigorous shaking Sometimes, lyses of the cultures were highly visible by bacterial debris.

Concentrated phage preparations were obtained by NaCl/Poly Ethylene Glycol (PEG) 8000 precipitation of LB lysates in accordance to protocols described by Sambrook and Russel (2001). Solid NaCl (final concentration 1.0 M) was added to each sample and, after stirred, the samples were maintained on ice for 1 hour. The samples were centrifuged at 11,000×g at 4° C. for 10 minutes to remove debris and the supernatants (LB lysates) were transferred to sterile flasks. Solid PEG 8000 (final concentration 10% w/v) was added to the lysates and the samples were kept on ice for at least 1 hour to allow the bacteriophage particles to precipitate. Precipitated bacteriophages particles were recovered by centrifugation at 11,000×g at 4° C. for 10 minutes and ressupended in SM buffer. These large-scale high-titer lysates concentrated stocks were stored at 4° C.

Bacteriophage DNA Isolation and Restriction

The extraction of bacteriophage DNA from large-scale high-titer lysate concentrated stocks was performed in small scale (Lockett, 1990). Contaminating bacterial nucleic acids was removed from concentrated phage solution by adding RNaseA (Sigma-Aldrich, St. Louis, Mo.) and DNaseI (Sigma-Aldrich, St. Louis, Mo.) to final concentrations of 20 µg ml$^{-1}$ and 5 µg ml$^{-1}$, respectively; followed by incubation for 30 minutes at 37° C. After nuclease digestion, 0.25 ml of Tris-SDS (0.3 M Tris-HCl, 100 mM EDTA, 1.25% SDS, pH 9.0) was added and the mixture was incubated at 65° C. for 30 minutes. In order to precipitate down the disrupted protein coat of the bacteriophages, 0.25 ml of ice-cold 3M potassium acetate, pH 4.8, was added and the mixture was placed on ice for 5 minutes. Insoluble material was removed by centrifugation at 15,000×g, in 2 minutes at room temperature and most of the supernatant removed taking care not to include any remaining insoluble flocculent material. DNA was precipitated out by adding 0.7 volumes of isopropanol to the supernatant and, after a second 2 minutes at room temperature, recovered by centrifugation at 15,000×g for 1 minute. DNA pellet obtained was dissolved in 0.3 ml of TE (10 mM Tris-HCl, 1 mM EDTA, pH 8.0) and 0.15 ml of 7.5 M ammonium acetate was added to this solution and DNA was reprecipitated with 2 volumes of cold ethanol. Another centrifugation at 15,000×g was carried out to spin down the DNA which was then washed with 0.5 ml of 70% ethanol. The DNA pellet was dried at room temperature to remove traces of ethanol and then dissolved in TE. Purified bacteriophage DNA was subsequently digested with EcoRI (Promega, Madison, Wis.) and electrophoresed on 0.8% agarose according with Sambrook and Russel (2001).

Statistical Analysis

A general linear mixed model was used to analyze the effect of a single dose of bacteriophage solutions on the growth curve of all 57 E. coli isolates. The outcome variable was the $OD_{600}$ of the LB broth culture, which was modeled as a Gaussian (normally distributed data) variable. The assumption that the residuals were normally distributed was satisfied by visually evaluating the distribution plot of the studentized residuals. The independent variables offered to the model were: treatment (11 different phage preparations and control) and time (from 1 until 12). The interaction of treatment and time was also included in the model. Our data were longitudinally collected and therefore had a series of repeated measures (total of 12) of optical density throughout the study period. This implies that data points were correlated within each E. coli isolate. To account appropriately for within correlation of the optical density, we modeled the error term by imposing a first-order autoregressive covariance structure. Variables and interaction were considered significant when their P-values<0.05.

Results

Phylogenetic grouping based on triplex PCR showed that all isolates of E. coli belonged to phylogroup B1, which generally includes both commensal non-pathogenic strains and some pathogenic strains (Rushen and de Passille, 2006). They typically lack the specialized virulence determinants found in pathogenic strains that cause intestinal or extra intestinal diseases (Neveux et al., 2006). Although, E. coli belonging to phylogroup B1 are not usually considered to be pathogenic strains, these strains acquire virulence factors by horizontal transfer, enabling them to become virulent and to invade immunocompetent host (Tucker et al., 2006; Fulwider et al., 2008) from host's reservoir.

Minimum Inhibitory Multiplicity of Infection

To determine the miMOI each host strain of E. coli was inoculated with 7 different doses of the respective bacteriophage preparation. The highest MOI tested was $10^2$ which is equivalent to 100 PFU of bacteriophage per 1 CFU of the host E. coli. The lowest MOI tested was $10^{-4}$ which is equivalent to 1 PFU of bacteriophage per 10,000 CFU of the respective host E. coli. In general bacterial growth was completely inhibited with extremely low MOI (FIG. 1) with the exception of phage preparations 4988-2 and 2540-4 which had miMOI of $10^1$ and $10^0$ respectively. Furthermore, dose-response effect was observed for all phage preparations; bacterial growth decreased as the MOI increased.

Figure 2:
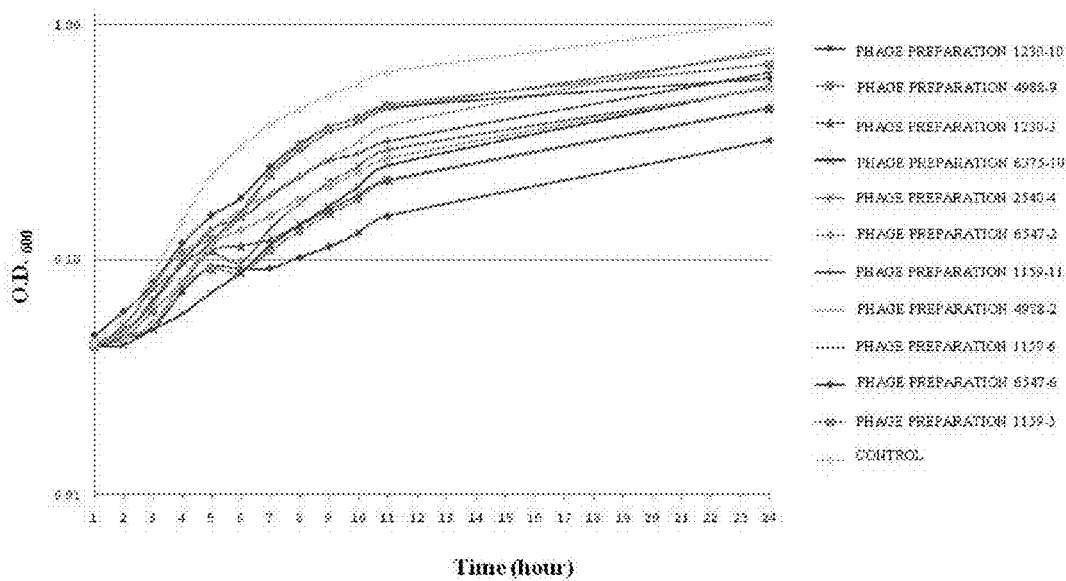
FIG. 2: Mean growth curve (OD600) for all 57 *E. coli* isolates, isolated from the uterus of postpartum cows, when inoculated with the 6 different bacteriophage solutions and in the absence of bacteriophage (control). All evaluated bacteriophage solutions were isolated from the manure ponds of two large commercial dairy farms.

Effect of a Single Dose (MOI=$10^2$) of Bacteriophage on the Growth Curve of all 57 E. Coli Isolates When assessing the effect of a single dose (MOI=$10^2$) inoculation of bacteriophage preparations on the growth curve of all 57 E. coli isolates it was observed that all 11 bacteriophage preparations significantly decreased the growth rate of the isolates when compared to the controls (FIG. 2). However, it was also observed that some bacteriophage preparations were more effective than others. The average $O.D._{600}$ was lowest for the bacteriophage preparation 1230-10 (0.11, 95% C.I. 0.06-0.16) and highest for the control (0.37, 95% C.I. 0.32-0.42) (Table1). Furthermore, the number of isolates that were completely inhibited (final $O.D._{600}<0.10$) by single dose bacteriophage inoculation differed between the different bacteriophage preparations. Bacteriophage preparation 1230-10 had the strongest antimicrobial activity and completely inhibited the growth of 71.7% (n=57) of all isolates. The combined action of bacteriophage preparations 1230-10, 6375-10, 2540-4, and 6547-2 had the broadest spectrum of action and would completely inhibit the growth (final $OD_{600} \leq 0.1$) of 80% of the E. coli isolates and considerably inhibited the growth (final $OD_{600} \leq 0.2$) of 90% of the E. coli isolates.

Bacteriophage DNA Isolation and Restriction

Figure 3:
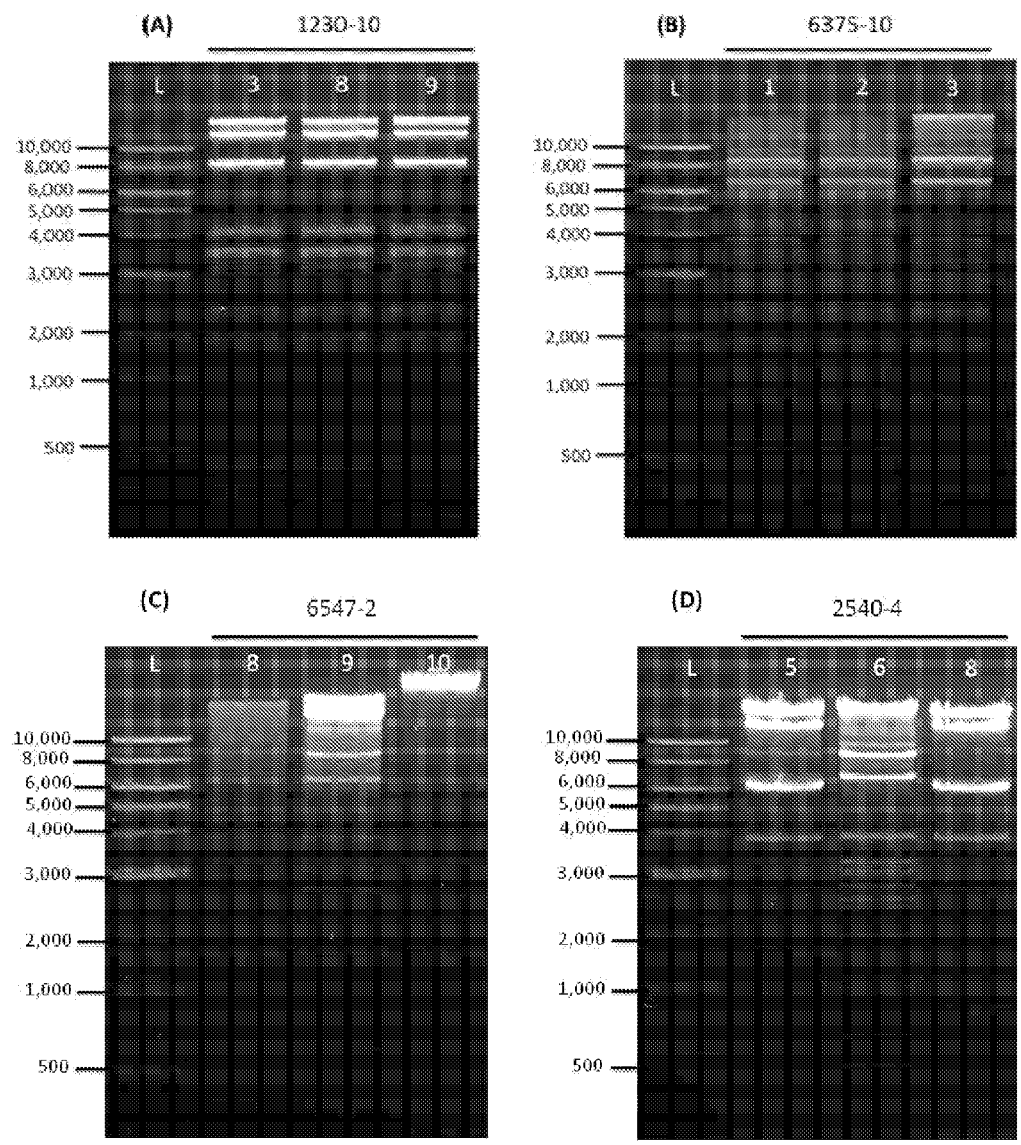
FIG. 3A-D. Restriction analysis of bacteriophage DNA from phage preparations 1230-10 [3, 8 and 9 (A)], 6375-10 [1, 2 and 3 (B)], 6547-2 [8, 9 and 10 (C)], and 2540-4 [5, 6 and 8 (D)]. DNA was digested with EcoRI (Promega, Madison, Wis.), and electrophoresed on 0.8% agarose gel. Lane identification: (L) 1 kb DNA ladder.

To assess the genetic diversity within and between the bacteriophage preparations, DNA from the phage preparations 1230-10, 6375-10, 2540-4, and 6547-2 was isolated, purified, digested with EcoRI (Promega, Madison, Wis.), and electrophoresed on 0.8% agarose gel. The restriction analysis demonstrated that all four phage preparations contained bacteriophages that were genetically distinct from each other based on the banding pattern of the fragments (FIG. 3). Additionally, it was observed that phage preparations 6547-2 and 2540-4 contained heterogeneous group of bacteriophages.

Discussion

Escherichia coli are a common cause of disease not only in food animals but also in humans. Several strains of E. coli are known to be virulent and to cause diseases such as gastroenteritis, urinary tract infection, peritonitis, mastitis, metritis, septicemia, and pneumonia (Clermont et al., 2000). However, strains of E. coli classified as non-pathogenic can also cause disease given the contamination load and the immunologic status of the animal. Phylogenetic studies have shown that most E. coli strains can be grouped into 4 main phylogenetic groups (A, B1, B2, and D) where most virulent extra-intestinal strains typically belong to groups B2 or D, and most commensal bacteria belong to group A (Herzer et al., 1990). In the present study all E. coli were classified by the triplex PCR as belonging to the phylogenetic group B1, which is represented by potentially pathogenic bacteria (Herzer et al., 1990; Clermont et al., 2000). Although, the presence of virulence factor in the genome of E. coli may partially explain the occurrence of clinical metritis it is important to emphasize that contamination load and immunologic status of the cow are equally important factors. Silva et al. (2008) reported that the simple presence of virulence factors in the genome of Arcanobacterium pyogenes isolated from the uterus of dairy cows was not predictive of clinical metritis (Silva et al., 2008). Schierack et al. (2006) reported that virulence factor gene profiles were similar for E. coli isolated from diarrheic piglets and normal piglets (Schierack et al., 2006).

The uterine lumen is a sterile environment up until parturition and postpartum contamination can be considered ubiquitous since over 85% the cows have bacterial contamination in the first week of lactation (Sheldon, 2004). Several cow related factors are known to increase the risk of clinical metritis by facilitating the access of environmental bacteria into the uterine lumen (e.g. assisted parturition and retained placenta) or by allowing excessive growth of bacterial population in the uterine lumen (e.g. twin parturition and suppressed immune system). Since the contamination of the uterine lumen seems unavoidable and the onset of clinical disease is related to the contamination load, bacteriophages and their use metaphylactically will decrease the bacterial load soon after parturition and consequently prevent the onset of clinical metritis and other postpartum uterine disease. The same could be accomplished with systemic or intrauterine antibiotics, however the problems associated with milk discard and the growing concern with the rise of antibiotic resistance may dampen enthusiasm with such approach.

The metaphylactic use of bacteriophages to treat and prevent bovine bacterial metritis and other postpartum uterine diseases has several advantages. It will decrease the bacterial load of E. coli and therefore decrease the incidence of clinical disease (Sheldon et al., 2006), there is an abundance of polyvalent environmental bacteriophages highly effective against *E. coli* (Brussow, 2005), rapid clearance of bacteriophages from the circulatory system will not be a problem since intrauterine therapy is a viable option, and iatrogenic endotoxemia is unlikely with intrauterine administration of purified phage lysates. Recent randomized clinical trial of bacteriophage therapy in mice and cattle have shown good results. Biswas et al. (2002) successfully rescued mice that were inoculated with lethal doses of vancomycin-resistant *Enterococcus faecium* with a single injection of a phage solution containing $3 \times 10^8$ pfu (plaque forming units) of a certain bacteriophage. Bacteriophage therapy was also reported successful when newly borne colostrum-deprived calves were inoculated with *E. coli* and treated with intramuscular inoculation of bacteriophages (Barrow et al., 1998). While bacteria may develop resistance to phages, it is incomparably simpler to develop new phages than new antibiotics. A typical drug-discovery process has a 3% chance of positive hits while in nature, as bacteria evolve resistance, relevant bacteriophages will evolve in concert. A few weeks are needed to obtain new phages for a newly-emerging strain of resistant bacteria. This is in favorable and sharp contrast to discovering and developing a new chemical antibiotic. Additionally, bacterial resistance to bacteriophage has been largely demonstrated under in vitro situations, in such over simplistic models where only two microbes are represented, the host (bacterial isolate) and the parasite (a bacteriophage).

In the present study, 11 bacteriophage preparations were isolated and characterized using standard techniques. All bacteriophage preparations successfully inhibited in vitro bacterial growth and a strong dose response was observed for all preparations indicating that higher MOI incremented antimicrobial activity. Furthermore, it was observed that the use of different bacterial isolates as bacteriophage host yielded genetically distinct bacteriophages. Brussow (2005) reviewed the literature that pertained to the use of bacteriophages as a therapeutic against *E. coli* diseases and reported that genetically distinct bacteriophages are isolated when different indicator cells from same stool sample are used. Additionally, we observed a genetic heterogeneity within some bacteriophage preparations indicating that different bacteriophages were active against the same bacterial host. Non-digestion of Eco10 6547-2 suggests no sites for the enzymes EcoRI or the phage produce single stranded DNA. Also, this bacteriophage can belong to the T-even like phages, which modify their DNA to protect it against the normal restriction system such that 99.9% of restriction enzymes will not cut it (Revel, 1967; Snyder et al., 1976). Potential inhibitors in the DNA sample are possible but not considered as clear restriction digestions were obtained from all other bacteriophages.

Human sewage has been considered to be one of the most diverse habitats for bacteriophages and sewage samples are commonly used to search for novel bacteriophages (Lusiak-Szelachowska et al., 2006). In the present study we used samples from manure systems of large commercial dairy farms. The manure lagoons of dairy farms hold thousands of tons of cattle waste which are accumulated for up to 7 months at a time allowing an incredible variety of microorganisms to thrive in that environment.

One of the concerns with the use of phage therapy is the potential transfer of undesirable genes (virulence determinants and antibiotic resistance genes) from the bacteriophages to host bacteria and from a host bacterium to another (Chen J and Novick R P, 2009). However, bacterial transduction is typically aided by lysogenic bacteriophages, as opposed to those that are lytic (potential antimicrobials). Nevertheless, genomic characterization of potential therapeutic bacteriophages would review the presence of undesirable genes and if such genes are found it would be prudent to not use those specific bacteriophages as therapy. Currently, there are no bacteriophages based therapeutic approved by the United States Food and Drug Administration (FDA) for the treatment of bacterial diseases of humans and animals. However, recently the FDA amended the food additive regulations to approve the use of a bacteriophage preparation on ready-to-eat meat and poultry (Lang, 2006). The use of naturally occurring bacteriophages in agriculture as a therapy of environmental diseases can be deemed harmless to humans and to the environment, especially if bacteriophages that were locally isolated are used, because the magnitude of bacteriophage and host-bacteria interactions is exponentially higher in the environment than it would be within a treated animal.

TABLE 1

Mean $OD_{600}$ for the entire experiment period (24 hours) by all different bacteriophage solutions and the control. A total of 57 *E. coli* isolates (isolated from the uterus of 10 postpartum cows) were treated with a dose of 100 PFU of bacteriophage per CFU of bacteria (MOI = $10^2$). All evaluated bacteriophage solutions were isolated from the manure ponds of two large commerical dairy farms.

| Treatment | Mean OD-600 | SE | 95% C.I. | Spectrum of action | |
|---|---|---|---|---|---|
| | | | | % $OD_{600} \leq 0.1^1$ | % $OD_{600} \leq 0.2^2$ |
| 1230-10 | 0.11 | 0.02 | 0.06-0.16 | 71.7 | 80.0 |
| 4988-9 | 0.14 | 0.02 | 0.09-0.18 | 61.7 | 71.7 |
| 1230-3 | 0.14 | 0.02 | 0.09-0.20 | 65.0 | 70.0 |
| 6357-10 | 0.15 | 0.02 | 0.10-0.20 | 60.0 | 66.7 |
| 2540-4 | 0.17 | 0.02 | 0.12-0.22 | 51.7 | 55.0 |
| 6547-2 | 0.17 | 0.02 | 0.15-0.25 | 41.7 | 56.7 |
| 1159-11 | 0.20 | 0.02 | 0.18-0.27 | 28.3 | 50.0 |
| 4988-2 | 0.23 | 0.02 | 0.20-0.29 | 25.0 | 50.0 |
| 1159-6 | 0.25 | 0.02 | 0.20-0.29 | 26.7 | 41.7 |
| 6547-6 | 0.25 | 0.02 | 0.20-0.29 | 21.7 | 23.3 |
| 1159-5 | 0.25 | 0.02 | 0.20-0.30 | 20.0 | 30.1 |
| Control | 0.40 | 0.02 | 0.32-0.41 | 0 | 0 |

Shaded fields indicate the combination of bacteriophage preparation that had the broadest spectrum of action.

[1] % $OD_{600} \leq 0.1$ = Percent of isolates that had an Optical Density equal or smaller than 0.1 at the end of the growth curve study.

[2] % $OD_{600} \leq 0.2$ = Percent of isolates that had an Optical Density equal or smaller than 0.2 at the end of the growth curve study.

Example 2

In Vitro Antimicrobial Activity Evaluation of a Bacteriophage Cocktail and Several Antibiotics The use of pathogenic-specific antimicrobials, as proposed by bacteriophage therapy, will reduce the incidence of resistance development. Eighty *Escherichia coli* isolated from the uterus of Holstein dairy cows were phenotypically characterized for antimicrobial resistance to ampicillin, ceftiofur, chloramphenicol, florfenicol, spectinomycin, streptomycin and tetracycline by broth microdilution method. The lytic activity of a bacteriophage cocktail against all isolates was performed by similar method. Additionally, the effect of different concentrations of antimicrobials and multiplicities of infections (MOI) of the bacteriophage cocktail on *E. coli* growth curve was measured. Isolates exhibited resistance to ampicillin (33.7%), ceftiofur (1.2%), chloramphenicol (100%) and florfenicol (100%). All strains were resistant to at least 2 of the antimicrobial agents tested; multidrug resistance (≥3 of 7 antimicrobials tested) was observed in 35% of E. coli isolates. The major multidrug resistance profile was found for ampicillin-chloramphenicol-florfenicol, which was observed in more than 96.4% of the multidrug resistant isolates. The bacteriophage cocktail preparation showed strong antimicrobial activity against multidrug-resistant E. coli. MOI as low as $10^{-4}$ affected the growth of the E. coli isolates. The ratio of 10 bacteriophage particles per bacterial cell (MOI=$10^1$) was efficient in inhibiting at least 50% of all isolates. All isolates resistant to florfenicol were resistant to chloramphenicol and as florfenicol was recently introduced into veterinary clinics, this finding suggests that the selection pressure of chloramphenicol, as well as other antimicrobials, may still play a relevant role in the emergence and dissemination of florfenicol resistance in E. coli. Bacteriophage cocktail has notable capacity to inhibit the in vitro growth of E. coli isolates and is a viable alternative to conventional treatment of postpartum uterine diseases such as metritis by reducing E. coli in uterus of postpartum dairy cows and consequently the incidence of clinical disease.

Material and Methods

Bacterial Strains and Culture Conditions

Eighty E. coli isolates were taken from a collection of likely commensal non-pathogenic and some pathogenic strains obtained from uterine secretion from Holstein dairy cows using the method described by (Bicalho et al., 2009). Briefly, uterine secretion was collected, diluted in saline buffer, and the sample aerobically cultured on MacConkey agar (Difco™) at 37° C. E. coli colonies were distinguished by a purple-red color. Typical E. coli colonies were streaked on CHROMagar™ E. coli for confirmation and further isolation. Colony morphology and characteristic appearance in smears stained by Gram's method was used to exam purity. Additionally, identification of isolated strains was carried out by 16S ribosomal RNA (rRNA)-encoding gene amplification (Simpson et al., 2006). Phylogenetic grouping was performed by triplex PCR which uses a combination of two genes (chuA and yjaA) and an anonymous DNA fragment (Clermont et al., 2000)(Simpson et al., 2006). A stock of all 80 isolates obtained was kept at −80° C. in Luria-Bertani (LB) (Difco™) broth containing 20% glycerol for further testing.

Bacteriophage Propagation

Bacteriophages were routinely propagated on E. coli strains originally used as host during the bacteriophage isolation. High-titer stocks for each bacteriophage preparation that compounds the cocktail were prepared in SM buffer (100 mM NaCl, 8 mM MgSO$_4$, 1 M Tris-HCl, pH 7.5) by the plate lysate method according to (Sambrook and Russell, 2001). To remove debris, the lysate obtained from the top agar were pooled and centrifuged at 10,000×g at 4° C. for 10 minutes and the supernatant was sterilized by filtering through a 0.22-µm-pore-size filter. These high titer stocks were used to compound the cocktail and determine the minimum inhibitory Multiplicity of Infection (MOI) of bacteriophage particles.

Antimicrobial Susceptibility Assay

Prior the MIC determinations, all 80 isolates were revived by subculture on Mueller-Hinton broth (BBL™) and incubated for 8-12 hours at 37° C. The MIC determinations were performed by broth microdilution method as described by the Clinical and Laboratory Standards Institute (CLSI, 2008) recommendations. The tests consisted of manually prepared 96-well microtiter plates containing the following seven antimicrobials (Sigma-Aldrich, St. Louis, Mo.): ampicillin, ceftiofur, chloramphenicol, florfenicol, spectinomycin, streptomycin and tetracycline. The dilutions for each antimicrobial tested ranged from 0.25 µg/ml to 256 µg/ml for all the antibiotics and all tests were performed in duplicates. The cultures were diluted in Mueller-Hinton broth to $10^5$ CFU/ml and an aliquot of 200 µl of the diluted culture was added to microtiter plate wells, containing various concentrations of the antimicrobials, to a total volume of 300 µl per well. The assays were carried out in duplicates and the required controls of adequacy of the broth to support the growth of the microorganism and the sterility of the broth done.

MIC was determined based on CLSI guidelines for the manually prepared panels (CLSI, 2008) after 18 hours of incubation at 37° C. under aerobic conditions and the first dilution with no visible growth was considered the MIC for each strain. In addition to the uterine E. coli isolates tested, the reference strain of E. coli ATCC 25922 was included as quality control for MIC determination, as recommended by the CLSI (CLSI, 2008). The MIC that inhibits at least 50% ($MIC_{50}$) and at least 90% ($MIC_{90}$) of the isolates, as well as the minimum and maximum MIC, were also derived.

Additionally, in parallel with the CLSI standard test, MIC for 57 isolates was determined by measurement of the bacterial growth spectrophotometrically (Moreira et al., 2005). In this case, the MIC was arbitrarily established as the minimum concentration of the antibiotic that completely inhibited growth of the cells for 2-3 hours after the beginning of the stationary phase of the control (E. coli growing in Mueller-Hinton broth) (~10 hours of incubation at 37° C. under aerobic conditions). Growth was periodically assessed spectrophotometrically in a microplate reader (Synergy™ 2, BioTek) at 600 nm. Curves were plotted with average of the duplicates. The results of this kinetic test were statistically analyzed to derive the mean MIC (mMIC) of the isolates for each antimicrobial tested.

Bacterial Challenge Test—Bacteriophage Cocktail Assay

A bacteriophage cocktail compounded of bacteriophages isolated from the manure lagoons of two large commercial dairy farms located near Ithaca N.Y. (Bicalho et al., 2009) was used to test the susceptibility of all 80 E. coli isolates and determine the minimum inhibitory Multiplicity of Infection (MOI) of the bacterial isolates for the bacteriophage cocktail. All 80 isolates were culture on Mueller-Hinton broth (BBL™) and incubated for 8-12 hours at 37° C. The cultures were diluted in Mueller-Hinton broth to $10^5$ CFU/ml and the challenge tests were performed in manually prepared 96-well microtiter plates containing different dilution of the bacteriophage cocktail in order to reach ratios ranging from $10^{-4}$ to $10^2$ PFU/CFU in wells containing $10^4$ CFU of E. coli; all tests were performed in duplicates. The assays were carried out in duplicates and the required controls of adequacy of the broth to support the growth of the microorganism and the sterility of the broth were done.

Minimum inhibitory MOI was determined after 18 hours of incubation at 37° C. under aerobic conditions and the first ratio with no visible growth was considered the minimum inhibitory MOI for each strain. The minimum MOI that inhibits at least 50% ($MOI_{50}$) and at least 90% ($MOI_{90}$) of the isolates, as well as the minimum and maximum MOI were also derived. Additionally, in parallel, minimum MOI for 57 isolates was determined by measurement of the bacterial growth spectrophotometrically, in which it was arbitrarily established as the minimum MOI that completely inhibited growth of the cells for 2-3 hours after the beginning of the stationary phase of the control; E. coli growing in Mueller-Hinton broth for approximately 10 hours of incubation at 37° C. under aerobic conditions. In this case, growth was periodically assessed spectrophotometrically in a microplate reader (Synergy™ 2, BioTek) at 600 nm. Curves were plotted with average of the duplicates. The results of this kinetic test were statistically analyzed to derive the minimum inhibitory mean MOI (minimum inhibitory mMOI) of the isolates for each antimicrobial tested.

Data Management and Statistical Analysis

A general linear mixed model was used to analyze the effect of the different antibiotic concentrations and bacteriophage MOIs on the growth curve of 57 $E.$ $coli$ isolates and determinate the mean values. The outcome variable was the $OD_{600}$ of the Mueller-Hinton (BBL™) broth culture, which was modeled as a Gaussian (normally distributed data) variable. The assumption that the residuals were normally distributed was satisfied by visually evaluating the distribution plot of the studentized residuals. The independent variables offered to the model were: treatment (bacteriophage cocktail and all antimicrobials tested) and time (from 1 until 10). The interaction of treatment and time was also included in the model. Our data were longitudinally collected and therefore had a series of repeated measures (total of 10) of optical density throughout the study period. This implies that data points were correlated within each $E.$ $coli$ isolate. To account appropriately for within correlation of the optical density, we modeled the error term by imposing a first-order autoregressive covariance structure. Variables and interaction were considered significant when their P-values<0.05.

Results

Bacterial Isolation and Characterization

All 80 isolated strains were confirmed to be $E.$ $coli$ both by cultural methods using chromogenic agar—CHROMagar™ $E.$ $coli$, and by rDNA amplification. Phylogenetic grouping based on triplex PCR showed that all isolates of $E.$ $coli$ belonged to phylogroup B1, which generally includes both commensal non-pathogenic, and some pathogenic $E.$ $coli$ strains (Smith et al., 2007). Furthermore, isolates from phylogroup B1 typically lack the specialized virulence determinants found in pathogenic strains that cause intestinal or extra intestinal diseases (Picard et al., 1999). Although, $E.$ $coli$ belonging to phylogroup B1 is not usually considered to be pathogenic strains, these strains can acquire virulence factors by horizontal transfer, enabling them to become virulent and invade immunocompromised host (Picard and Goullet, 1988) from host's reservoir.

Antimicrobial Resistance Patterns in $E.$ $Coli$ Isolated from Uterus Fluid

Interpretation of the MICs based on CLSI criteria (CLSI, 2008) for the isolates of $E.$ $coli$ from this study allowed us to conclude that 33.7% of the isolates are resistant to ampicilin, 1.2% resistant to ceftiofur, and 100% resistant to chloramphenicol and to florfenicol (Table 2). The $MIC_{50}$ and the $MIC_{90}$ for ampicillin were 16 μg/ml and 32 μg/ml, respectively (Table 2). Nearly all isolates (98.7%) were susceptible to ceftiofur although this antimicrobial had showed the broadest range of MICs. The $MIC_{50}$ and the $MIC_{90}$ for ceftiofur were both 1 μg/ml (Table 2). No susceptibility was found to chloramphenicol and florfenicol. The $MIC_{50}$ and the $MIC_{90}$ for chloramphenicol were 64 μg/ml and 128 μg/ml, respectively, and the $MIC_{50}$ and the $MIC_{90}$ for florfenicol were both 16 μg/ml (Table 2). Among the antimicrobial agents tested, spectinomycin ($MIC_{50}$=32 μg/ml; $MIC_{90}$=64 μg/ml), streptomycin ($MIC_{50}$=8 μg/ml; $MIC_{90}$=8 μg/ml) and tetracycline ($MIC_{50}$=1 μg/ml; $MIC_{90}$=2 μg/ml) had excellent activity against the $E.$ $coli$ isolates from this study, whereas none of them were resistant to these antimicrobials. Of the 80 isolates tested, all strains were resistant to at least 2 of the antimicrobial agents tested and multidrug resistance (higher or equal to 3 of 7 antimicrobials tested) was observed in 35% of the $E.$ $coli$ isolates. The major multidrug resistance profile was found for ampicillin-chloramphenicol-florfenicol, which was observed in more than 96.4% of the multidrug resistant isolates.

In Vitro Antimicrobial Activity of Bacteriophage Cocktail Against Antimicrobial Multidrug Resistant $E.$ $Coli$ The bacteriophage cocktail preparation previously defined (Bicalho et al., 2009) showed efficient antimicrobial activity against antimicrobial multidrug resistant $E.$ $coli$ from uterine secretion from Holstein dairy cows (Table 2). MOI as low as $10^{-4}$ affected the growth of 1.25% of the $E.$ $coli$ isolates (Table 2). The $MOI_{50}$ found for the bacteriophage cocktail was $10^1$ PFU/CFU (Table 2), which means that the ratio of 10 bacteriophage particles from the bacteriophage cocktail per bacterial cell was efficient in inhibiting at least 50% of the isolates. The $MOI_{90}$ for the cocktail was >$10^2$ PFU/CFU (Table 2).

Figure 4:
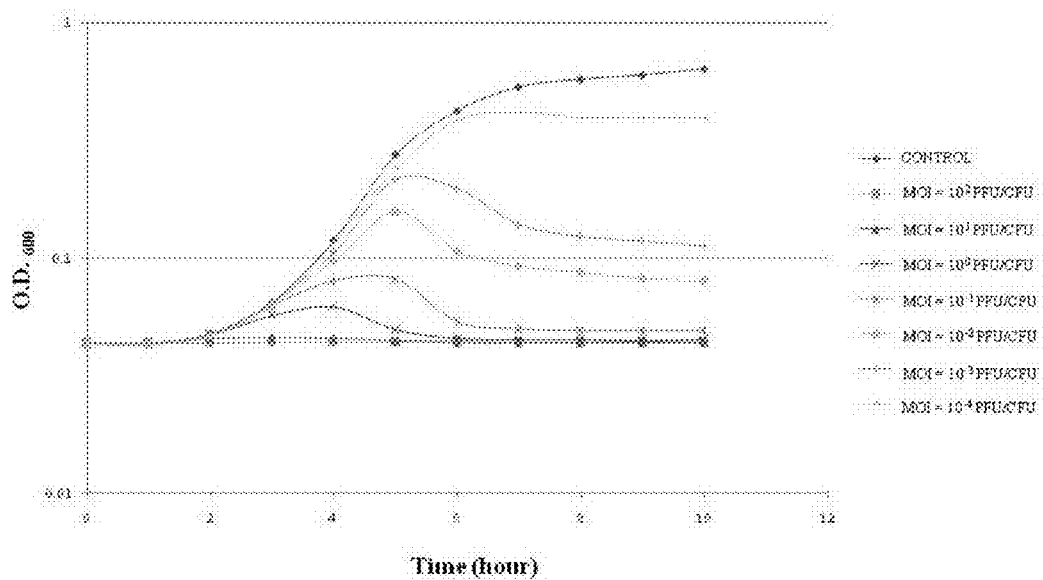
FIG. 4. Effect of bacteriophage cocktail on the growth curve of a single *Escherichia coli* isolate exemplifying the typical kinetics of growth and dose response effect observed across all isolates. The minimum MOI (mMOI), arbitrarily defined as the minimum MOI that completely inhibited growth of the cells for 2-3 hours after the beginning of the stationary phase of the control, is 10-1.

Measurement Antimicrobial and Bacteriophage Cocktail Effect on the Growth Curve of $E.$ $Coli$ We have isolated environmental bacteriophages that caused lysis of $E.$ $coli$ isolates from the uterus of postpartum dairy cows and tested the lytic activity of these bacteriophages in order to compose a broad spectrum bacteriophage cocktail to control $E.$ $coli$ growth (Bicalho et al., 2009). MOI of $10^2$ was standardized to define the composition of the bacteriophage cocktail and showed excellent effect in inhibiting bacterial growth (Bicalho et al., 2009). Growth of all $E.$ $coli$ isolates was tested in different MOIs (FIG. 4). It was possible to observe the dose response related to the different PFU/CFU ratios.

Figure 5:
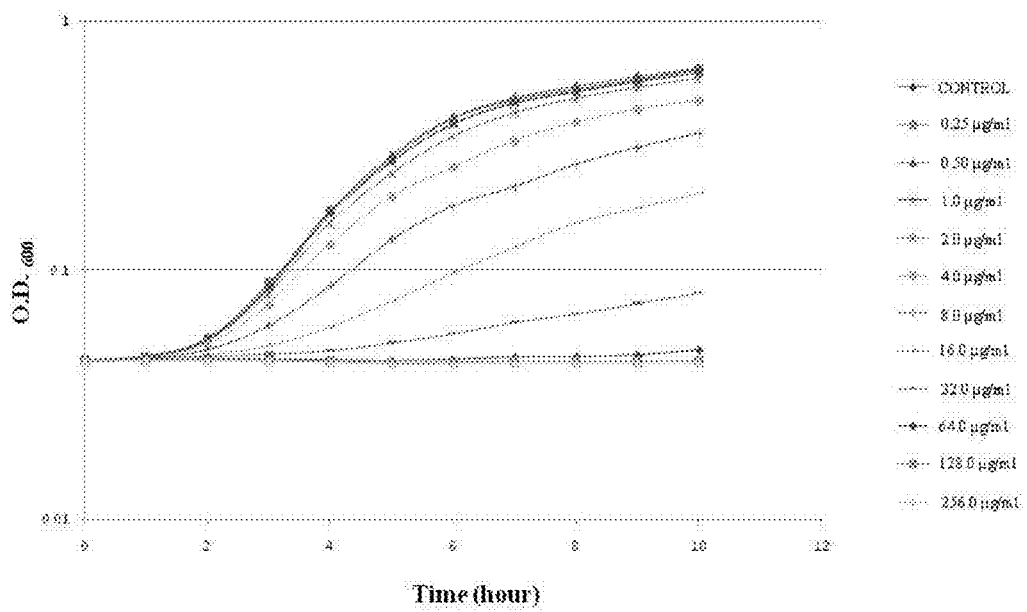
FIG. 5A-D. Effect of antibiotics on growth of *Escherichia coli* isolated from the uterus of postpartum Holstein dairy cows.
Figure 5:
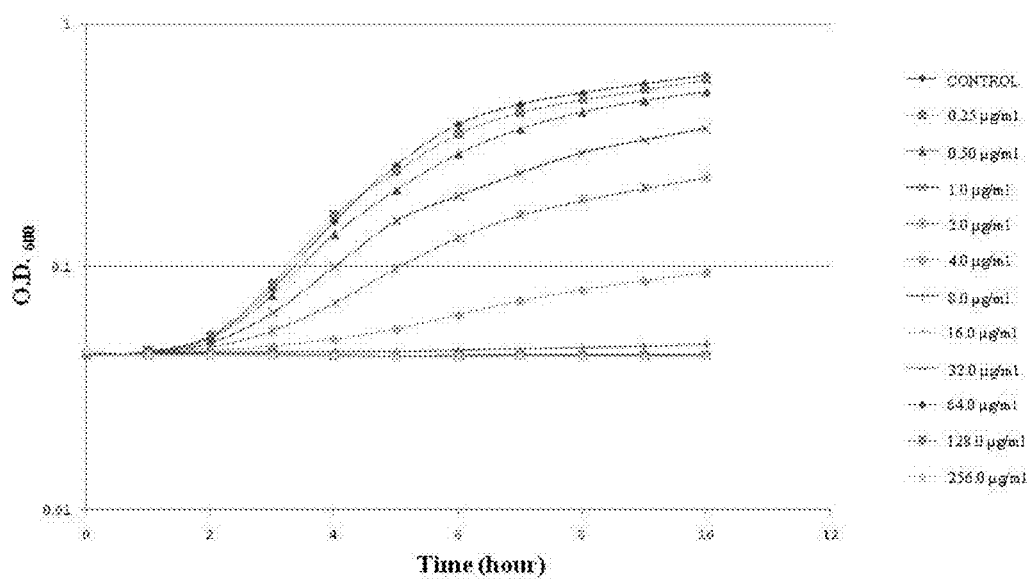
Figure 6:
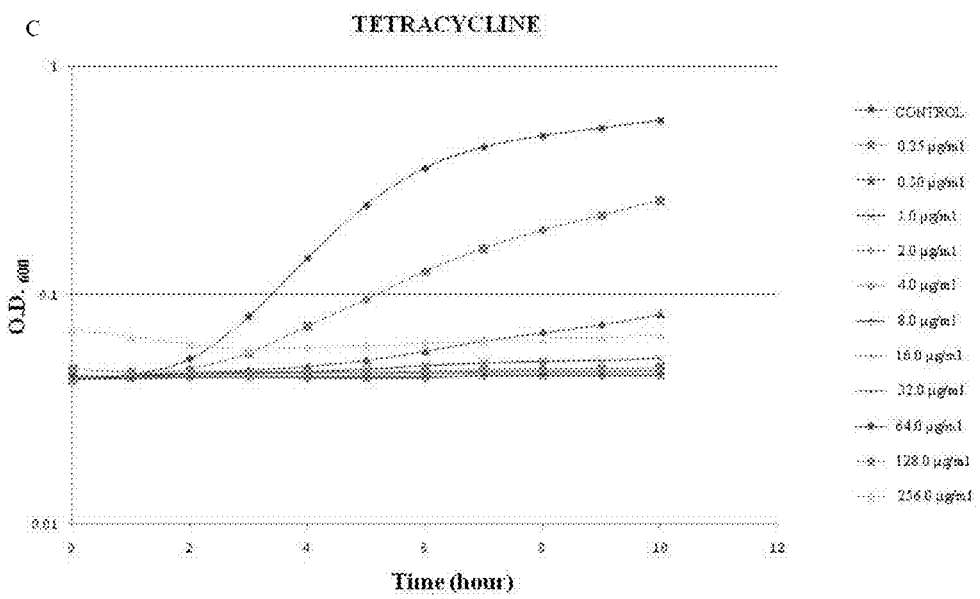
FIG. 6A-C. Effect of antibiotics on growth of *Escherichia coli* isolated from the uterus of postpartum Holstein dairy cows.
Figure 7:
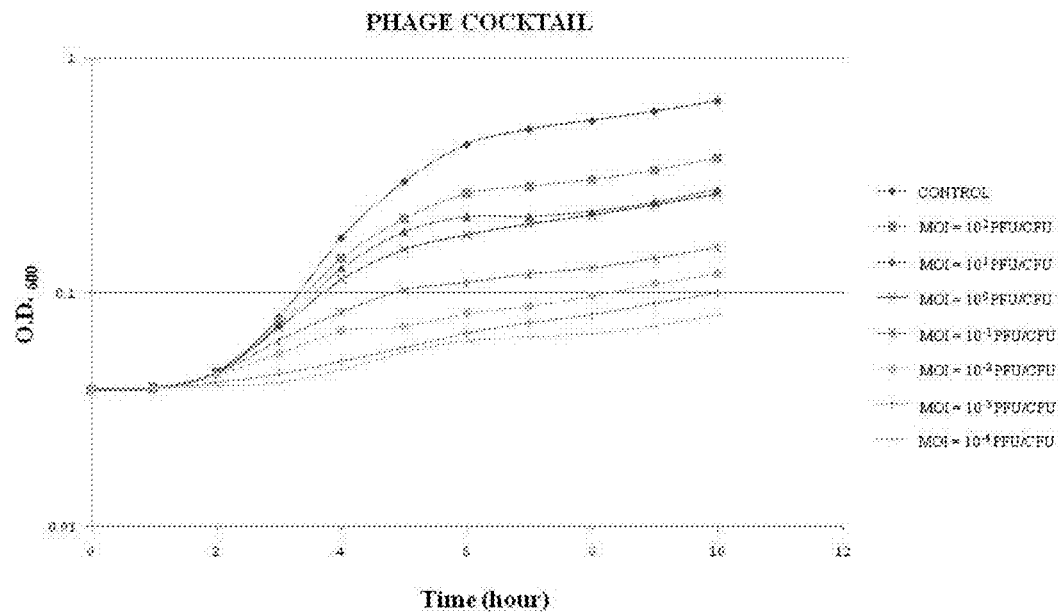
FIG. 7. Mean effect of bacteriophage cocktail on growth curve of all 57 *Escherichia coli* isolates. *Escherichia coli* were isolated from uterine secretion of postpartum Holstein dairy cows.

The mean MICs (mMICs) for each antimicrobial and the minimum inhibitory mMOI for the bacteriophage cocktail were arbitrarily established as the minimum concentration mean of the antibiotic and the minimum mean MOI, respectively, that completely inhibited growth of the cells for 2-3 hours after the beginning of the stationary phase of the control (FIG. 5, FIG. 6 and Table 3).

The mMICs for ampicillin (16 μg/ml), florfenicol (16 μg/ml), spectinomycin (32 μg/ml) and streptomycin (8 μg/ml) had the same value of the $MIC_{50}$ calculated using the CLSI standard method (CLSI, 2008) (FIG. 5, Table 2 and Table 3). The mean MICs for chloramphenicol (128 μg/ml) and tetracycline (2 μg/ml) were the same for the $MIC_{90}$ values (Table 2 and Table 3). Ceftiofur had a significant greater mMIC (16 μg/ml) than the maximum MIC value observed according to the CLSI standard test (FIG. 5, Table 2 and Table 3).

The minimum inhibitory mMOI for the bacteriophage cocktail was ≥$10^2$ (FIG. 6 and Table 3). The mean value was greater than the values derived for minimum inhibitory MOIs, which was defined by the same criteria defined by CLSI (CLSI, 2008) for MIC determination. The bacteriophage cocktail and all antimicrobials tested significantly decreased the mean $OD_{600}$ when compared to the controls (Table 3). Amongst the antibiotics tested ceftiofur and tetracycline were the most effective in inhibiting bacterial growth; the mean $OD_{600}$ was 0.05 (95% CI=0.04-0.06) for both. The bacteriophage cocktail significantly inhibited bacterial growth in all MOIs tested when compared to the control (95% CI=0.27-0.35) (Table 3). Mean $OD_{600}$ for MOIs ranging from $10^{-1}$ to $10^2$ were inferior to 0.01. It should be emphasized that the criteria used to defined mMIC and minimum mMOI, based on spectrophotometrical measurements, is stricter than the interpretation that adheres to the CLSI guidelines (CLSI, 2008), which is based on visual detection of bacterial growth.

Discussion

During the past decade, the threat of antimicrobial resistance has become increasingly real and its global dimensions have been increasingly recognized (Tollefson and Miller, 2000). The use of antimicrobial as growth promoter or prophylactic agents in animal agriculture may be a partial cause of the rise of antimicrobial resistance. The high level of resistance to multiple antimicrobials can lead to serious public health problems (Tollefson et al., 1999; Tollefson and Miller, 2000). *Escherichia coli* is one of the most common bacteria isolated from uterine infection and is known to be responsible for puerperal metritis (Sheldon and Dobson, 2004). Antimicrobial resistance of *E. coli* from uterine fluid of postpartum dairy cows has been poorly described in the literature. Only few studies have reported the antimicrobial activity of various agents against microorganisms that were isolated from uterus of dairy cows (Sheldon and Dobson, 2004).

Ampicillin, a β-lactam that belongs to the broad spectrum group of the penicillins, is widely used in human and veterinary medicine. Resistance to β-lactam antimicrobial agents in *E. coli* is primarily mediated by β-lactamases, which hydrolyze the β-lactam ring inactivating the antibiotic (Livermore, 1995). Many different β-lactamases have been described in ampicillin-resistant *E. coli* (Livermore, 1995). As showed in Table 2, almost 34% of the *E. coli* isolates showed resistance to ampicillin. Various levels of ceftiofur resistance have been reported in studies of *E. coli* from calves. Sawant et al. (2007) reported the occurrence of 48% of ampicillin-resistant *E. coli* from feces of healthy lactating dairy calves.

Ceftiofur, which is an extended-spectrum cephalosporin that belongs to the class of β-lactam, is commonly used as a treatment of metritis and other bacterial diseases, such as pneumonia and foot rot. The most common mechanism of cephalosporin resistance is also through production of β-lactamases, although extended-spectrum cephalosporins, like ceftiofur, have increased ring stability against some β-lactamases (Livermore, 1995). Of all *E. coli* isolates, 1.25% showed resistance to ceftiofur (Table 2). A possible mechanism for this resistance is presence of cephamycinases, coded by the $bla_{CMY2}$ gene, which share extensively homology to chromosomal ampC β-lactamases (Winokur et al., 2001). Various levels of ceftiofur resistance have been reported in studies of *E. coli* from calves. White et al. reported the occurrence of 69% of ceftiofur-resistant *E. coli* from diarrheic calves, while smaller prevalence rates of 11% (Bradford et al., 1999) and 13% (Sawant et al., 2007) have been also reported.

All isolates were resistant to chloramphenicol and 1.25% was resistant to the higher concentration tested (≥254 μg/ml) (Table 2). Chloramphenicol is a broad-spectrum antibiotic extensively used in veterinary medicine until 1980s when concerns over its toxicity emerged (Settepani, 1984). Resistance to chloramphenicol is well characterized in Gram-negative bacteria and is commonly mediated through enzymatic inactivation of the drug, commonly mediated by chloramphenicol acetyltransferases (CAT) (Schwarz et al., 2004) or nonenzymatically through active efflux of chloramphenicol by simple or multidrug efflux systems (Moreira et al., 2005). Resistance to chloramphenicol as observed in this study was particularly interesting because the use of this drug in food animals was banned by United States Food and Drug Administration (FDA) in the 1980s (Gilmore, 1986). Although, chloramphenicol is not used in metritis treatment, resistance likely persisted due to co-selection, which occurs with transmission of linked antimicrobial resistance genes on plasmids, transposons, and/or integrons (Bennett, 2008).

Florfenicol, a fluorinated structural analog of chloramphenicol, was approved for veterinary use in food animals by the US FDA in 1996 for treatment of bovine respiratory pathogens. Three florfenicol resistance genes, cfr, fexA and floR, which also mediate resistance to chloramphenicol, have been described (Schwarz et al., 2004). Florfenicol resistance mediated by the floR genes, which is a homolog of the chloramphenicol resistance efflux gene, cmlA (Arcangioli et al., 2000), and codes a chloramphenicol/florfenicol exporter, has been identified in various Gram-negative bacteria, including *E. coli*. As observed to chloramphenicol resistants, all *E. coli* isolates tested in this study showed resistance to florfenicol (Table 2).

It is known that the structural modification to form florfenicol rendered resistance to inactivation by CAT enzymes and, consequently, chloramphenicol-resistant strains, in which resistance is based exclusively on CAT activity, are susceptible to florfenicol (Schwarz et al., 2004). Furthermore, multidrug efflux system, which is widely distributed among bacteria, can pump out a wide range of compounds that may have few structural similarities. Therefore, resistance due to floR gene, which mediates combined resistance to florfenicol and chloramphenicol by efflux of the drug, should explain the strong associations between chloramphenicol and florfenicol resistance profile found here. However, further molecular study of these isolates is required to confirm this hypothesis. A similar incidence of cross-resistance has been reported in a study that showed that 85% of *E. coli* isolates from diarrheic dairy calves were resistant to both florfenicol and chloramphenicol (White et al., 2000).

*Escherichia coli* is one of the most important known dairy cattle metritis pathogen (Sheldon and Dobson, 2004). In our study, *E. coli* isolated from uterine secretion from Holstein dairy cows showed multidrug resistance (35%) and the major profile observed (96.4%) was ampicillin-chloramphenicol-florfenicol. Mobile genetic elements, such as plasmids, transposons and integrons are known to underlie much of the maintenance and spreading of antimicrobial-resistance determinants (Bennett, 2008). Furthermore, some studies have showed that *E. coli* and *Salmonella* isolates from animals and humans had the same antimicrobial resistance determinants (Fey et al., 2000; Maidhof et al., 2002). The use of antibiotics in food animals could be associated with the selection of antibiotic resistance mechanisms in pathogenic and nonpathogenic isolates of *E. coli*. Hence, prudent use of antibiotics in veterinary medicine is highly recommended.

The mean $OD_{600}$ derived from growth curve of the 57 *E. coli* isolates for both the 7 antimicrobials tested and the bacteriophage cocktail were significantly different of that observed for the controls (Table 3). Considering the rigorous interpretative criteria (based on spectrophotometrical detection of bacterial growth) used to analyze the data, measure and compare growth curve of all isolates in presence of different antimicrobial agents, the method proposed seems applicable although caution in the generalization of our results has been taken to avoid incorrect predictions.

The growing concern about the rise of multidrug-resistant bacteria in humans and animals has revamped the interest in bacteriophage therapy research. Bacteriophages have been successfully used in animal trials against a broad range of pathogenic *E. coli* (Brussow, 2005). The metaphylactic use of bacteriophages to treat and prevent bovine bacterial metritis and other postpartum uterine diseases has several advantages. It will decrease the bacterial load of *E. coli* and therefore decrease the incidence of clinical disease, there is an abundance of polyvalent environmental bacteriophages highly effective against *E. coli*, rapid clearance of bacteriophages from the circulatory system will not be a problem since intrauterine therapy is a viable option, and iatrogenic endotoxemia is unlikely with intrauterine administration of purified phage lysates. The bacteriophage cocktail preparation showed remarkable antimicrobial activity against antimicrobial-multiresistant *E. coli* isolated from the uterus of Holstein dairy cows (Table 3). Higher MOIs (PFU/CFU ratios higher than $10^2$) should be tested in future studies in vitro to establish ratios that completely inhibit bacterial growth during longer periods. Genetic diversity of this phage preparation was assessed (Bicalho et al., 2009) and further characterization and purification should be performed prior animal trials.

This work presents a short overview of antimicrobial resistance in *E. coli* isolated from uterus of postpartum dairy cows. In addition, it was also demonstrated that a bacteriophage cocktail was effective at inhibiting *E. coli* growth in vitro and is a viable alternative to antibiotics for the treatment and metaphylaxis of bovine metritis and other postpartum uterine diseases.

The findings of phenotypic characterization of antimicrobial resistance suggest that *E. coli* from uterus can be an important reservoir for antimicrobial resistance determinants. Therefore, the non-pathogenic *E. coli* isolates could be an important source of resistance genes to other bacteria that share the same environment.

As ampicillin, ceftiofur and florfenicol may potentially induce cross-resistance between animal and human bacterial pathogens, their prudent use in veterinary medicine is highly recommended. All isolates resistant to florfenicol are resistant to chloramphenicol and as florfenicol was recently introduced into veterinary clinics, this finding suggests that the selection pressure of chloramphenicol, as well as other antimicrobials, may still have performing relevant role in the emergence and dissemination of florfenicol resistance in *E. coli*.

Bacteriophage cocktail has notable capacity to inhibit the in vitro growth of *E. coli* isolates and it is a viable alternative to conventional treatment of metritis by reducing *E. coli* in uterus of postpartum dairy cows and consequently the incidence of clinical disease.

TABLE 2

Summary of minimum inhibitory concentrations (MICs) to antimicrobials and minimum inhibitory multiplicity of infection (MOI) to bacteriophage cocktail for *Escherichia coli* recovered from uterine secretion from Holstein dairy cows (n = 80 isolates)

| | MICs (μg/ml) | | | | | | | | | | | | | | |
|---|---|---|---|---|---|---|---|---|---|---|---|---|---|---|---|
| | Distribution of isolates (%) | | | | | | | | | | | | | | % |
| Antimicrobial | ≤0.25 | 0.5 | 1 | 2 | 4 | 8 | 16 | 32 | 64 | 128 | ≥254 | Min | 50% | 90% | Max | Resistant |
| Ampicillin | | | | | | 26.2 | 40 | 31.2 | 1.2 | | 1.2 | 8 | 16 | 32 | 256 | 33.7 |
| Ceftiofur | 7.5 | 40 | 45 | 5 | 1.2 | 1.2 | | | | | | ≤0.25 | 1 | 1 | 8 | 1.2 |
| Chloramphenicol | | | | | | | | 1.2 | 66.2 | 31.2 | 1.2 | 32 | 64 | 128 | 256 | 100 |
| Florfenicol | | | | | | 47.5 | 45 | 7.5 | | | | 8 | 16 | 16 | 32 | 100 |
| Spectinomycin | | | | | | | 18.7 | 67.5 | 13.7 | | | 16 | 32 | 64 | 64 | 0 |
| Streptomycin[a] | | | 3.7 | 31.2 | 61.2 | 3.7 | | | | | | 2 | 8 | 8 | 16 | 0 |
| Tetracycline | 10 | 71.2 | 18.7 | | | | | | | | | 0.5 | 1 | 2 | 2 | 0 |

| | Minimum inhibitory MOI (PFU/CFU) | | | | | | | | | | | |
|---|---|---|---|---|---|---|---|---|---|---|---|---|
| | Distribution of isolates (%) | | | | | | | | | | | |
| Bacteriophage | $10^{-4}$ | $10^{-3}$ | $10^{-2}$ | $10^{-1}$ | $10^0$ | $10^1$ | $10^2$ | $>10^2$ | Minimum | 50% | 90% | Maximum |
| cocktail | 1.2 | 13.7 | 3.7 | 11.2 | 6.2 | 11.2 | 5.0 | 37.5 | $10^{-4}$ | $10^1$ | $>10^2$ | $>10^2$ |

Shaded fields indicate the resistance range for each antimicrobial. Vertical double bars mark the breakpoint between sensitive and resistant.
[a]The MIC for Streptomycin, which does not have a CLSI guideline, was taken from the National Anitmicrobial Resistance Monitoring System (NARMS) 2005.

TABLE 3

Mean $OD_{600}$ for *Escherichia coli* (n = 80 isolates) growth curve during 10 hours at 37° C. under aerobic conditions in Mueller-Hinton (BBL ™) broth treated with seven antimicrobials and bacteriophage cocktail (MOI ranging from $10^{-4}$ to $10^2$ PFU/CFU). Mean MIC and minimum inhibitory mean MOI were arbitrarily derived.

| Treatment | Mean MICs[a] | Mean $OD_{600}$ | Standard Error | 95% C.I. |
|---|---|---|---|---|
| | Antimicrobial | | | |
| Ampicillin | 16 | 0.14 | 0.002 | 0.13-0.15 |
| Ceftiofur | 16 | 0.05 | 0.002 | 0.04-0.06 |
| Chloramphenicol | 128 | 0.18 | 0.002 | 0.16-0.19 |

TABLE 3-continued

Mean OD$_{600}$ for *Escherichia coli* (n = 80 isolates) growth curve during 10 hours at 37° C. under aerobic conditions in Mueller-Hinton (BBL ™) broth treated with seven antimicrobials and bacteriophage cocktail (MOI ranging from 10$^{-4}$ to 10$^2$ PFU/CFU). Mean MIC and minimum inhibitory mean MOI were arbitrarily derived.

| | | | | |
|---|---|---|---|---|
| Florfenicol | 16 | 0.10 | 0.002 | 0.09-0.11 |
| Spectinomycin | 32 | 0.17 | 0.002 | 0.16-0.18 |
| Streptomycin | 8 | 0.11 | 0.002 | 0.10-0.12 |
| Tetracycline | 2 | 0.05 | 0.002 | 0.04-0.06 |
| CONTROL | — | 0.29 | 0.002 | 0.29-0.30 |

| Treatment | % OD$_{600}$ | Mean OD$_{600}$ | Standard Error | 95% C.I. |
|---|---|---|---|---|
| Bacteriophage cocktail | ≤0.1[2] | ≤0.2[3] | | |
| MOI = 10$^{-4}$ | 17.5 | 40.4 | 0.19 | 0.02 | 0.16-0.23 |
| MOI = 10$^{-3}$ | 31.6 | 61.4 | 0.15 | 0.02 | 0.11-0.19 |
| MOI = 10$^{-2}$ | 54.4 | 59.6 | 0.14 | 0.02 | 0.10-0.18 |
| MOI = 10$^{-1}$ | 66.7 | 75.4 | 0.09 | 0.02 | 0.06-0.13 |
| MOI = 10$^{0}$ | 68.4 | 84.2 | 0.07 | 0.02 | 0.04-0.11 |
| MOI = 10$^{1}$ | 78.9 | 84.2 | 0.06 | 0.02 | 0.03-0.09 |
| MOI = 10$^{2}$ | 78.9 | 84.2 | 0.05 | 0.02 | 0.02-0.09 |
| CONTROL | 0.0 | 0.0 | 0.31 | 0.02 | 0.27-0.35 |

Figure 9:
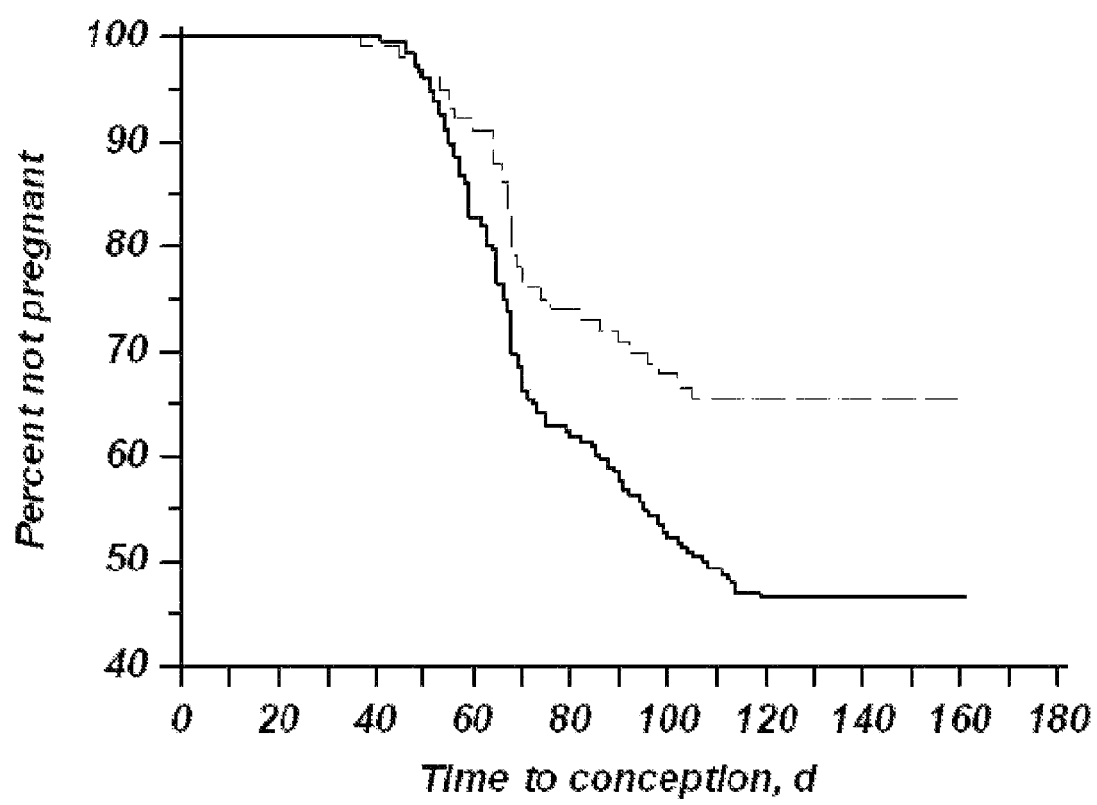
FIG. 9: Kaplan-Meier survival analysis illustrating the effect of fimH on the calving-to-conception interval. The interrupted line represents the group of cows contaminated with fimH carrying *Escherichia coli* (n=109) and the solid line are the cows with negative cultures (n=249) and with non fimH carrying *E. coli* (n=16).

[1]The mean values for MICs were estimated from the graphics on FIG. 9.
[2]% OD$_{600}$ ≤ 0.1 = Percent of isolates that had an Optical Density equal or smaller than 0.1 at the end of the growth curve study.
[3]% OD$_{600}$ ≤ 0.2 = Percent of isolates that had an Optical Density equal or smaller than 0.2 at the end of the growth curve stu Example 3

Molecular and Epidemiological Characterization of Bovine Intrauterine Pathogenic *Escherichia coli* (IUPEC)

This example describes the isolation and characterization of IUPEC strains.

Material and Methods

Farm, Management and Sample Collection

Data were collected from 4 dairy farms located near Ithaca, N.Y., from Aug. 17, 2009, to Jan. 29, 2010. Farm A milked 2,800 cows, farm B milked 3,000 cows, farm C milked 1,600 cows and farm D milked 1,000 cows. These farms were selected because of their long history of a working relationship with the Ambulatory and Production Medicine Clinic at Cornell University. The herds consisted of Holstein cows housed in free-stall barns with waste paper pulp bedding. Cows were milked 3 times daily in milking parlors. All lactating cows were offered a total mixed ration (TMR) consisting of approximately 55% forage (corn silage, haylage, and wheat straw) and 45% concentrate (corn meal, soybean meal, canola, cotton seed, and citrus pulp) on a dry matter basis of the diet. The diet was formulated to meet or exceed the NRC nutrients requirements for lactating Holstein cows weighing 650 kg and producing 45 kg of 3.5% fat corrected milk (FCM).

Uterine swabs were performed by the research team (five veterinarians and one veterinarian student) in a total of 378 cows (200 cows in farm A, 74 in farm B, 63 in farm C, and 41 in farm D). The average DIM at sampling was 2 to 7 DIM. To isolate *E. coli* from uterus a uterine swab was collected as follows: cows were restrained and the perineum area was cleansed and disinfected with a 70% ethyl alcohol solution, a sterile swab covered by a sterile pipette (inside a plastic sheath) was introduced to the cranial vagina. The pipette was manipulated trough the cervix into the uterus. There the sheath was ruptured, and the swab was exposed to uterine secretion. The swab was pulled inside the pipette and it was kept in a transportation media at 4° C. until it was processed in the laboratory.

Case Definition

Presence of fetid watery red-brown uterine discharge, associated with systemic signs of illness, and rectal temperature greater than 39.5° C. was defined as metritis. The diagnostic of metritis was evaluated by the farms employees in the first 14 DIM. Clinical endometritis was defined as a presence of purulent or mucopurulent discharge, by retrieving vaginal mucus using the Metricheck device (Metricheck, SimcroTech, Hamilton, New Zealand) as described in a previous study {{663 McDougall, S. 2007}}. The diagnostic of clinical endometritis was evaluated by the research crew, at 28+/−3 DIM. Because of farm and management logistics, the diagnostic of clinical endometritis enrolled 117 cows in the study.

Bacterial Isolation and DNA Extraction

The uterine swabs were taken to the laboratory and cultured aerobically on MacConkey agar (Difco) at 37° C. and *E. coli* colonies were distinguished by a purple-red color. Five typical *E. coli* colonies from the MacConkey agar cultures were picked and subsequently streaked on CHROMagar-*E. coli* for isolation and further identification of *E. coli* species. Selected colonies were stored in Luria-Bertani (LB) broth containing 20% glycerol at −80° C. DNA was extracted using InstaGene Matrix™ (Biorad) as previously described {{669 Higgins, J. 2007}}.

Polymerase Chain Reaction and Gel Electrophoresis

All reaction were performed with 25 µL using 24 µL of 1× Green GoTaq® Master Mix (made from 2× Green GoTaq® Master Mix consisting of Green GoTaq® Reaction Buffer, 400 µM dATP, 400 µM dGTP, 400 µM dCTP, 400 µM dTTP and 3 mM MgCl2; Promega Corp., Madison, Wis.) and primers, and 14, of DNA extract. All primers and their respective concentrations are described in Table 4. All the thermal cycling protocols were performed in a 2720 Thermal Cycler (Applied Biosystems, CA). Negative controls consisting of the PCR mixture without addition of DNA were included in all PCR runs. Amplification products were separated by electrophoresis through a 1.2% (w/v) agarose gel, stained with 0.5 µg/ml ethidium bromide, and visualized with KODAK Gel Logic 100 Imaging System (GL 100). Positive results were considered to be amplicons that had the expected molecular size.

PCR 16S were performed for *E. coli* identification; cycling parameters were 94° C. for 10 min followed by 30 cycles of 94° C. for 1 min, 55° C. for 1 min, and 72° C. for 1 min, and a final extension at 72° C. for 10 min {{670 Malinen, E. 2003}}. All cultures that did not presented the 340-bp fragment in the gel electrophoresis were excluded from the study. The genetic diversity of *E. coli* isolates was evaluated by randomly amplified polymorphic DNA (RAPD)-PCR with informative primer 1283 (Table 4). Cycling parameters were 94° C. for 5 min followed by 4 cycles of 94° C. for 5 min, 36° C. for 5 min, and 72° C. for 5 min, followed by 30 cycles of 94° C. for 1 min, 36° C. for 1 min, and 72° C. for 1 min, and a final step at 72° C. for 10 min {{676 Wang, G. 1993}}. The images were visually analyzed; isolates from the same cow were compared and *E. coli* colonies that presented distinct genome profiles were selected for the subsequent analyses. After RAPD-PCR, 362 *E. coli* isolates were selected for further analyses.

Phylogenetic grouping was performed by triplex PCR, which uses a combination of two genes (chuA and yjaA) and an anonymous DNA fragment {{667 Clermont, O. 2009}}. The triplex PCR was performed using 3 pairs of primes; the amplification protocol was 94° C. for 5 min, followed by 35 cycles at 94° C. for 15 s, 60° C. for 30 s and 72° C. for 45 s, and a final extension at 72° C. for 7 min {{669 Higgins, J. 2007}}. *E. coli* strains were classified as A, B1, B2 and D using the arrangement pattern of the three bands {{667 Clermont, O. 2009}}.

A multiplex cdt PCR was performed to detect which *E. coli* isolates presented sequences common to the cdtB genes using 4 primers (Table 4). The thermal cycling conditions were 94° C. for 5 min, 30 cycles of 94° C. for 1 min, 55° C. for 1 min and 72° C. for 1 min, and a final step of 72° C. for 10 min {{675 Toth, I. 2003}}. *E. coli* isolates that presented a PCR product size of 466 base pairs were considered positive for presence of cdtB genes.

A Multiplex 16plex PCR was conducted to assess *E. coli* isolates that presented genes related to diarrheagenic *E. coli;* 16 pairs of primers were used in this PCR (Table 4). Cycling parameters were 98° C. for 30 s, 30 cycles at 98° C. for 10 s, 63° C. for 20° C., and 72° C. for 30 s, with a final step at 72° C. for 10 min {{666 Antikainen, J. 2009}}. Furthermore, a Multiplex 15plex PCR was performed to identify VFs associated with UPEC; 15 pairs of primers were used {{672 Moreno, E. 2005}}. To facilitate the interpretation of the gel image, the primers were separated into two pools. Pool A was made with 8 pairs of primers (Allele III f, Allele III r, Afa f, Afa r, sfa 1, sfa 2, hlyA f, hlyA r, cnf1, cnf2, FyuA f, FyuA r, TraT f, TraT r, Ibe10 f, and Ibe10 r), and Pool B was made of 7 pairs of primers (PapA f, PapA r, Allele I f, Allele I r, Allele II f, Allele II r, FimH f, FimH r, AerJ f, AerJ r, kps II f, kps II r, RPAi f, and RPAi r). The PCR reactions of Pools A and B were done separately; thermal cycling protocol was 95° C. for 12 min, followed by 25 cycles at 94° C. for 30 s, 63° C. for 30 s, and 68° C. for 3 min, followed by a final part at 72° C. for 10 min {{672 Moreno, E. 2005}}.

DNA Gyrase (gryB) Amplification, Sequencing, and Phylogenetic Analysis

For this molecular analysis only genetically distinct bacteria (based on RAPD-PCR gels) presenting at least one of the following combination of VF genes were used; fimH and hlyA, fimH and ibeA, fimH and kpsMII, fimH and cdt, and fimH and astA. Chromosomal DNA was extracted as previously described and amplified by PCR in a termocycler 2720 Thermal Cycler (Applied Biosystems, CA). PCR reaction, conditions, and primers were used as previously described by {{665 Fukushima, M. 2002}}. The purified PCR products were sequenced using DNA Illumina Paired-End sequencing in the Cornell University Life Sciences Core Laboratory Center (CLC), Ithaca, N.Y. PCR fragments were determined by using the sequencing primers UP1S (5'-GAAGTCATCATGACCGTTCTGCA-3', SEQ ID NO:1) and UP2Sr (5'-AGCAGGGTACGGATGTGC-GAGCC-3', SEQ ID NO:2) {{665 Fukushima, M. 2002}}. For phylogenetic analysis, gyrB sequences from 41 IUPEC genetically distinct bacteria were aligned with 1 *Escherichia Fergusonii* strain, 5 *Salmonella* enteric subsp. enteric strains, 1 *Shigella flexneri*, 1 *Shigella dysenteriae*, 2 *Shiguella boydii*, and 33 *Escherichia coli* strains. DNA gyrase sequences (gyrB) were aligned using the Clustal-W algorithm using the software Geneious 4.8.4 (Biomatters Ltd, Auckland, New Zealand) and adjusting for 1,050 bases. All bacterial strains used in this phylogenetic analysis, with the exception of the IUPECs, have had their whole chromosomal genome sequenced and were publically available in the National Center for Biotechnology Information (NCBI) website at the time the analysis was performed. Detail information regarding *E. coli* pathotype and strain identification was included in the phylogenetic tree. Evolutionary relationship was inferred using the Neighbor-Joining method and the evolutionary distances were computed using the Tamura-Nei method {{677 Tamura, K. 1993}}. Bootstrap values were calculated from 1000 replicate analyses.

Statistical Analysis

Hierarchical cluster analysis was performed using the RAPD-PCR agarose gel pattern data form one randomly selected *E. coli* isolate per culture positive cow. Hierarchical cluster analysis was done using the Ward method of the statistical software JMP (SAS Institute Inc., North Carolina USA). For the subsequent analysis the research unit was the cow. To facilitate data analysis and interpretations a new 3 level variable was created for each of the 32 investigated VFs. Cows were classified as 0 when they were culture negative, as 1 when the cow was culture positive but the VF was absent in all *E. coli* isolates, and as 2 when the culture was positive and the VF factor was present in at least one *E. coli*.

Partition analysis was performed in JMP and for this analysis the dependent variable in the model was the dichotomous variable metritis (0 or 1) and the independent variables were; birth (singleton or twin), calving (assisted or unassisted), parity (primiparous or multiparous). Additionally the phylogenetic grouping (A, B1, B2, D) an all tested virulence factors were offered to the model as independent variables. Several logistical regression models were performed in Stata (Stata Corp LP, Texas USA) to assess the effect of the VFs on the probability of metritis and endometritis. The dependent variable in these models were metritis (yes or no) and endometritis (yes or no) and the independent variable were; the identified VFs, parity group (1-3), and farm. Adjusted probabilities and respective 95% confidence intervals were estimated from the logistic regression equations using the predicted probability option in Stata. An stratified analysis was performed the assess the interaction of the VFs astA, cdt, kpsMII, ibeA, and hlyA and fimH on the probability of metritis using the categorical modeling option of JMP.

Results

Bacterial Isolation, Characterization, and RAPD-PCR Cluster Analysis

Figure 8:
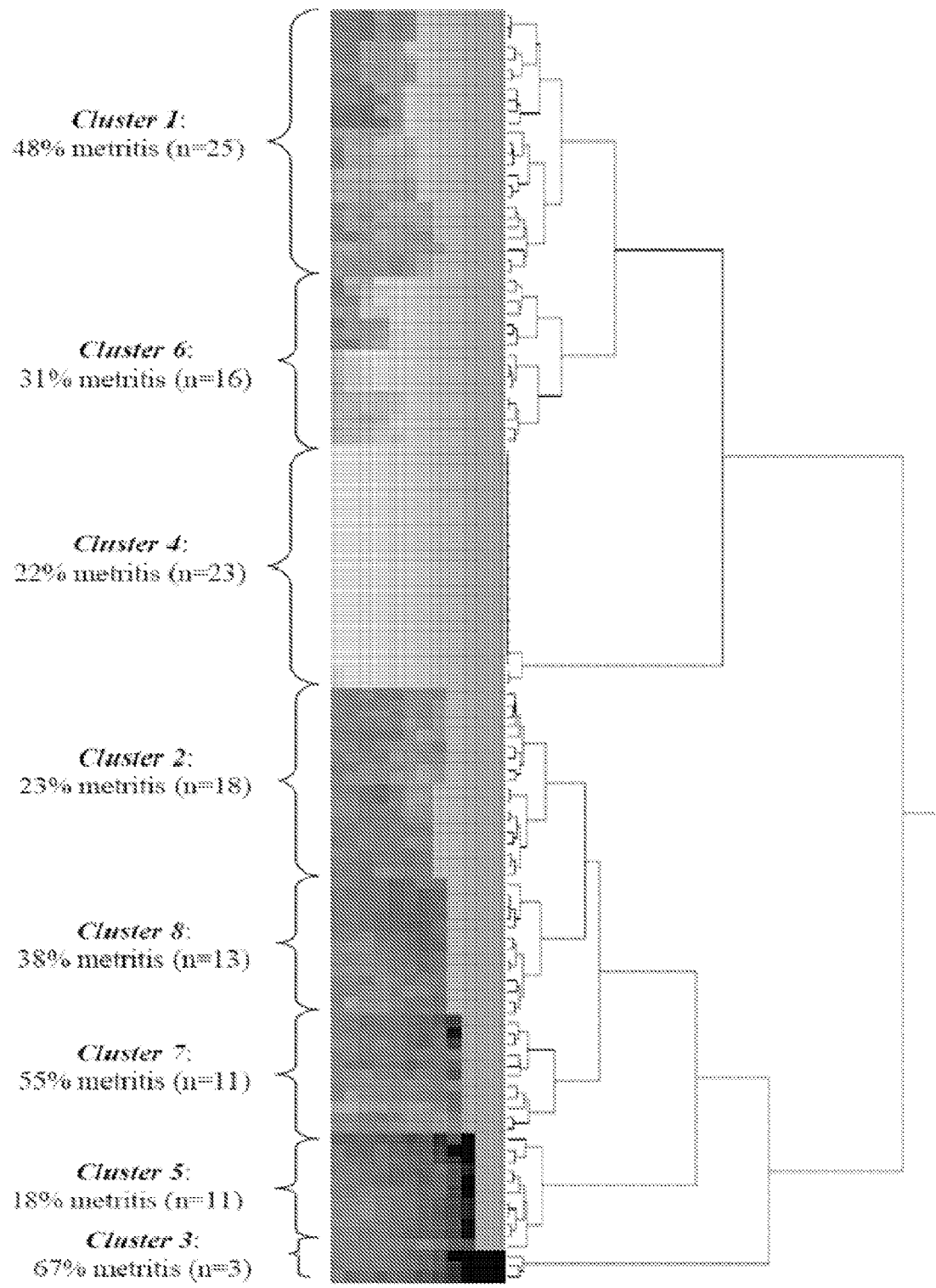
FIG. 8: Randomly amplified polymorphic DNA (RAPD)-PCR dendogram. One *E. coli* isolate per cow was randomly selected to be used in this analysis; a total of 120 bacterial isolates from 120 different cows were used in this analysis. Cluster numbers and respective metritis incidences are also presented.

All isolates (total of 625) were confirmed to be *E. coli* by cultural methods using chromogenic agar (CHROMagar). However, 14 isolates were negative for rDNA amplification, and were excluded from the study. Phylogenetic grouping based on triplex PCR showed that 24 isolates belonged to phylogenetic group A, 237 to group B1, 16 to group B2, and 74 to group D. The incidence of metritis was 48, 25, 43, and 46% for the phylogenetic groups A, B1, B2, and D, respectively (data not shown). The incidence of endometritis was 66, 60, 66, and 53 for the phylogenetic groups A, B1, B2, and D, respectively (data not shown). DNA fingerprinting using RAPD-PCR was performed for all 611 (5 isolates per contaminated cows) isolates and reviewed that on average there were 2.8 genetically distinct *E. coli* per contaminated cow. A cluster analysis was performed using the DNA fingerprinting information from the RAPD-PCR agarose gels. The analysis was performed with the number of clusters set to 8. The RAPD-PCR banding pattern appear to have an association with the pathogenicity of the *E. coli* isolates, because there was significant variation of the probability of metritis amongst the 8 different clusters; metritis incidence varied from 67% on cluster 1 to 18% on cluster 5 (FIG. 8).

Risk Factors Analysis for Intrauterine *E. Coli* Contamination.

A total of 374 cows were used in this study of which 33.4% were positive for *E. coli* culture. Cows that had twin parturition were at 4.4 times increased odds of intrauterine *E. coli* contamination compared to cows that gave birth to live female calves (P-value<0.01, Table 9). Stillborn parturitions and births of live male calves also increased the odds of intrauterine contamination by *E. coli* (3.7 and 1.6, respectively) when compared with births of live female calves (P-value<0.01, Table 9). Furthermore, body condition score at uterine swab sampling was associated with the odds of intrauterine contamination by *E. coli*. The odds of intrauterine *E. coli* contamination were 2.8 and 2.3 times higher for cows with BCS=3 and BCS<3 compared to cows with BCS>3 (P-value<0.01).

Association of *E. Coli* Virulence Factors with the Risk of Postpartum Metritis.

Of the 32 virulence factors evaluated only 11 were identified in the studied collection of *E. coli*; cdt, astA, hlyA, fyfA, traT, Pap G allele 1 and 2, ibeA, papaH, kpsMII, and fimH. Of the identified VFs only 6 were significantly associated with metritis; fimH, astA, cdt, kpsMII, ibeA, and hlyA (Table 8).

Figure 10:
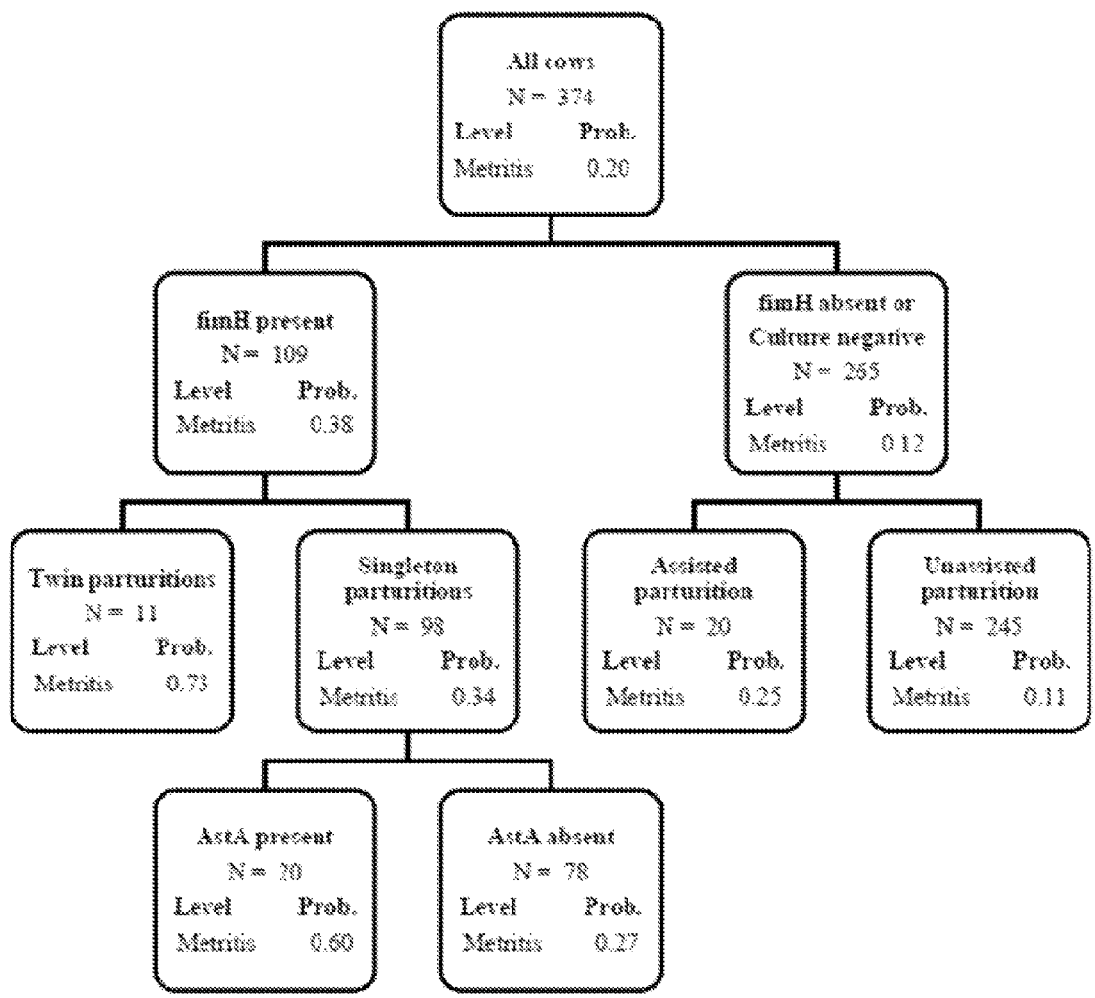
FIG. 10: Partition analysis tree illustrating the hierarchical order of the risk factors for metritis. The dependent variable in the model was the dichotomous variable metritis and the independent variables were; birth (singleton or twin), calving (assisted or unassisted), parity (primiparous or multiparous). Additionally the phylogenetic grouping (A, B1, B2, D) and all tested virulence factors were offered to the model as independent variables. The tree indicates that the virulence factor fimH was the most important predictor of metritis and the variables birth, calving, and the virulence factor astA were second, third and fourth most relevant predictors, respectively.

A partition analysis was perform to estimate the ranking of all the virulence factors and risk factors analyzed and the virulence factor fimH was the strongest predictor of metritis (FIG. 10). This can be explained by the high prevalence of the fimH gene in intrauterine *E. coli* (87% n=125) and also because of the higher probability of metritis in the presence of fimH genes; cows with at least one fimH carrying *E. coli* isolate were at a 6.0 increased odds of metritis when compared to culture negative cows. Moreover, cows that were positive cultured for *E. coli* carrying the cdt, astA and hlyA genes were 6.7, 12, 10.5 times more likely to have metritis, respectively, than cows that did not present uterine contamination (Table 8).

Figure 11:
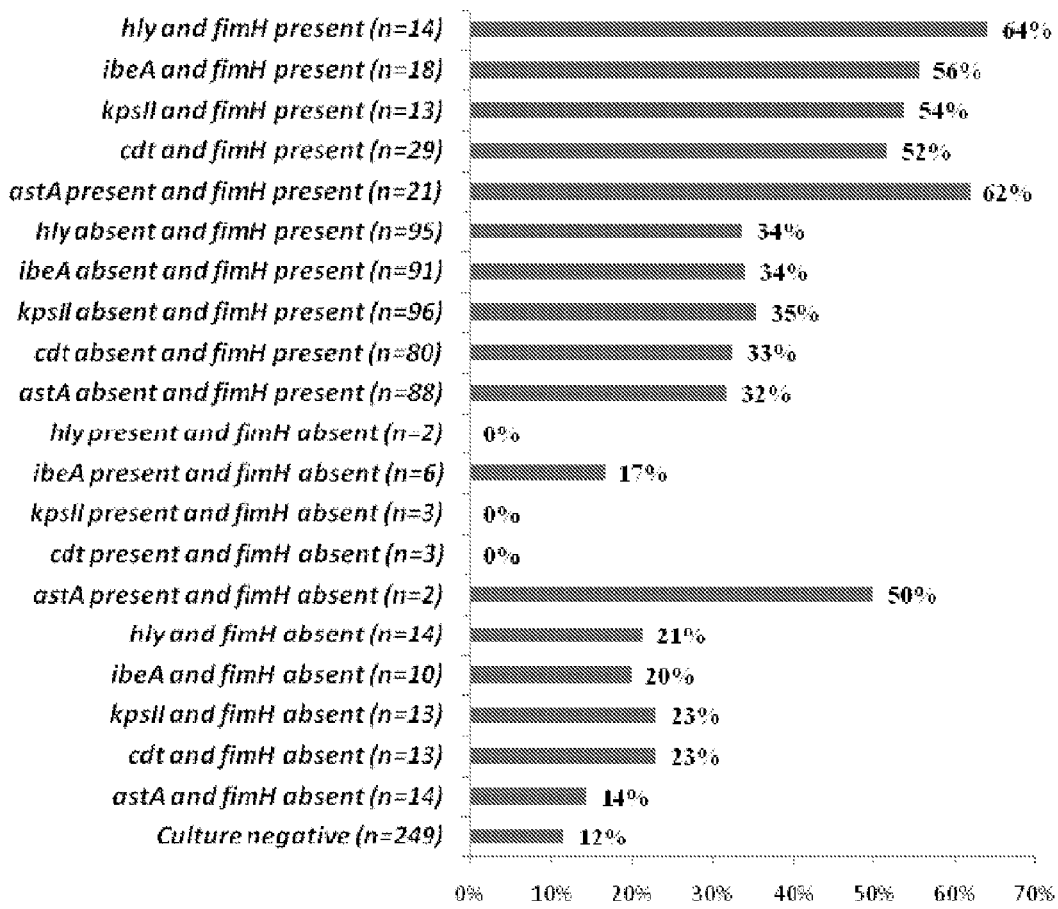
FIG. 11: Graphical illustration of the interaction of astA, cdt, kpsII ibeA, and hly with fimH on the incidence of metritis. Only culture positive cows were used for this analysis.

To further understand the interaction of astA, cdt, kpsMII, ibeA, and hlyA with fimH on the probability of metritis a stratified descriptive analysis was performed (FIG. 11). When the VF fimH was absent the incidence of metritis was low (<24%) even in the presence of other VFs, with the exception of VF astA. However, the incidence of metritis for cows contaminated with fimH carrying *E. coli* was equally high in the absence of all other VFs. Additionally, there appears to be a synergetic relationship between the VFs astA, cdt, kpsMII, ibeA, and hlyA and fimH because the incidence of metritis was highest (>52%) when fimH occurred concurrently with one of those five VFs (FIG. 11).

Association of *E. Coli* Virulence Factors with the Risk of Clinical Endometritis.

Further analysis was performed for the VFs fimH, astA, cdt, kpsMII, ibeA, and hlyA evaluating their effect on the incidence of clinical endometritis. Cows cultured for *E. coli* carrying fimH, cdt and astA genes were 2.6, 3.7 and 4.6 times increased odds of having clinical endometritis, respectively, compared to cows that did not present uterine contamination (Table 9).

Association of *E. Coli* Virulence Factors with Reproductive Parameters.

Culture positive cows with fimH carrying *E. coli* were 1.8 times less likely to become pregnant than cows with no uterine contamination (Table 10). Additionally, by 120 days in milk (DIM), 35% of the cows that had uterine contamination with *E. coli* carrying fimH gene were pregnant, while 55% of the cows without uterine contamination or with uterus contaminated by *E. coli* not carrying fimH gene were pregnant (FIG. 8). Furthermore, cows with uterine contamination by *E. coli* carrying cdt and kpsMII genes were 2.3 and 9.2 less likely to become pregnant, respectively, than cows that did not have uterine contamination (Table 10).

DNA Gyrase (gryB) Phylogenetic Analysis

Figure 12:
FIG. 12: Phylogenetic tree illustrating the evolutionary distance between 41 genetically distinct strains of intrauterine pathogenic *E. coli* (IUPEC), 33 strains of *E. coli* with known pathotypes, 4 *Shigella*, and 5 strains of *Salmonella*.

For this analysis, the DNA gyrase sequence from 41 IUPEC genetically distinct bacteria were aligned with 1 *Escherichia Fergusonii* strain, 5 *Salmonella enteric* subsp. *enteric* strains, 1 *Shigella flexneri*, 1 *Shigella dysenteriae*, 2 *Shiguella boydii*, and 33 *Escherichia coli* strains. FIG. 12 shows the phylogenetic tree for these species based on the gyrB gene sequence. All *Salmonella* grouped in the same clade apart from the large clade of the *E. coli*. All *E. coli* form the O157:H7 serogroup grouped together and their gyrB sequences were close to identical; 4 IUPECs also grouped with the O157:H7 *E. coli*. All ExPEC reference *E. coli* grouped in the same clade and 9 IUPECs were grouped with ExPECs. The majority of the IUPECs (23) were grouped in a clade adjacent to the ExPECs.

Discussion

The present study demonstrated that IUPEC plays an important role in the pathogenesis of puerperal uterine infection. Dairy cows infected with IUPEC in the early postpartum (3-7 d postpartum) were at higher risk of developing puerperal metritis and clinical endometritis at around 10 and 35 d postpartum respectively. As a consequence of IUPEC uterine infection the reproductive performance of affected cows was severely decreased.

The uterine lumen is a sterile environment up until parturition and postpartum contamination is common; over 85% of cows have bacterial contamination in the first week of lactation (Sheldon et al., 2004a). Several cow related factors are known to increase the risk of metritis by facilitating the access of environmental bacterial into the uterine lumen (e.g. assisted parturition and retained placenta) (Benzaquen et al., 2007) or by allowing excessive growth of bacterial population in the uterine lumen (e.g. twin parturition and suppressed immune system) (Sheldon et al., 2006).

In the present study, it was observed that the status of the newborn calf (twin, stillborn, and gender) significantly affected the probability of intrauterine *E. coli* contamination; cows that had twin parturition were 4.4 times more likely to be infected with IUPEC. Previous epidemiological research from our group has demonstrated that twining, calf weight, and stillborn parturition significantly decreased reproductive efficiency and cow survivability (Bicalho et al. 2007a, Bicalho et al. 2007b, Linden et al., 2009). The present study provided important insight about how calving related factors are associated with poor reproductive efficiency associating newborn calf status with probability of IUPEC infection.

The significance *E. coli* in the pathogenesis of puerperal uterine infection is poorly understood and few studies have attempted to elucidate the etiological role of *E. coli*. Recently, a collection of cattle uterine *E. coli* strains were screened for the presence of 15 VF genes and none were associated with uterine disease (Silva et al., 2009). Silva et al. (2009), concluded that uterine *E. coli* are opportunistic environmental bacteria since none of the evaluated VF appeared to affect the probability of uterine infection. In contrast, the present study evaluated a total of 32 VFs of which 6 were significantly associated with the incidence of metritis and endometritis. The identification of the VF genes fimH, astA, cdt, kpsMII, ibeA, and hlyA and the increased risk of uterine disease and reproductive failure and these significant VFs were not evaluated by Silva et al. (2009). Sheldon et al. (2010) evaluated the effect of 17 VF genes and none were found to be associated with uterine disease. Of the six significant VFs (fimH, astA, cdt, kpsMII, ibeA, and hlyA) found in the present study, ibeA was the only VF that was also assessed by Sheldon et al. (2010) and none of the isolates in that study were ibeA positive. However, in the present study a total of 374 cows and a total of 625 bacterial isolates were analyzed which is a much higher sample size compared with previous studies (Sheldon et al., 2010; Silva et al., 2009).

In humans, *E. coli* is a major cause of urinary tract infection (UTI); estimated to be the primary cause of over 80% of community acquired urinary tract infection (Struelens et al., 2004). The pathogenesis of human UTI is likely to start by the contamination of the urethra and bladder by fecal *E. coli* including UPECs and commensal flora. Hours after contamination the bladder environment will select for bacteria expressing type 1 fimbriae, tissue colonization and damage follows (Kaper et al., 2004). It is likely that the early stage of the pathogenesis of postpartum uterine infection in dairy cattle is similar to human UTI. In the present study, the VF gene fimH was highly prevalent in *E. coli* infected cows and was the most important predictor of metritis and endometritis. Type 1 pili containing fimH adhesion is present in virtually all uropathogenic *E. coli* and fimH immunization in a murine model prevented in vivo colonization of the bladder mucosa by 99% (Langermann et al., 1997). In contrast, it is well known that other opportunistic bacteria are associated with metritis and endometritis, such as *Pseudomonas* spp., *Streptococcus* spp., *Staphylococcus* spp., *Pasteurella multocida*, *Clostridium* spp., *Fusobacterium* spp. and *Bacteroides* spp. (Azawi et al., 2008). Nevertheless, recent research indicates that the infected uterus in the first week post partum is predominated by *E. coli* which alters the intra-uterine environment supporting future infection by other opportunistic anaerobic bacteria starting in the second week postpartum (Dohmen et al., 2000, Zerbe et al., 2001).

The group of ExPEC is diverse and includes several pathotypes including UPEC, NMEC, APEC, and necrotoxigenic *E. coli* (NTEC). All ExPEC will encounter similar challenges during the process of establishing extraintestinal infections and as a consequence they are likely to share similar VF genes (Johnson et al., 2008). The IUPEC bacteria described in this study presented numerous relationships with human ExPECs and avian pathogenic *E. coli* (APEC). The VF gene ibeA (invasion of brain endothelium) plays an important role in neonatal gram-negative meningitis, which is mainly caused by vertical transmission of *E. coli* (Huang et al., 2001). It has been suggested that the VF gene ibeA contributes to the invasiveness of *E. coli* to the brain microvascular endothelial cells (BMEC) via a ligand-receptor interaction (Huang et al., 2001). It is possible that such ligand-receptor interaction can be facilitated by ibeA expression in mammalian tissues other than BMEC and such as the endometrium. It has also been reported that the VF ibeA plays an important role on the pathogenesis of extra intestinal infection of birds by APEC. Germon et al., (2005) demonstrated that the virulence of an ibeA-free mutant APEC was decreased compared to APEC expressing ibeA. The prevalence of ibeA in the present study was 19.2% which is not very different than the prevalence found in APEC (26%) (Germon et al., 2005), neonatal meningitis *E. coli* (NMEC) (33-40%) and vaginal isolates (32%) (Johnson et al., 2001, Obata-Yasouka et al., 2002).

The VF gene kpsMII encodes the capsules K1 or K5 and has been associated with cellulitis in chickens (de Brito et al., 2003), and urinary tract infection in women (Moreno et al., 2009, Moreno et al., 205). The VF gene kpsMII was found in 12.8% of the *E. coli* positive cows which is comparable to 16% found in chickens with cellulitis (de Brito et al., 2003), and 21% found in urinary tract infection in humans (Johnson et al., 2001). Another significant VF gene encountered on the present study was the protein hly which is a heat-labile extracellular protein synthesized by a large proportion of ExPEC isolates (Smith et al., 2008). The hly toxin is responsible for poring the membrane and lysing a number of different mammalian cells (Lally et al., 1999). A total of 12.8% of the *E. coli* positive cows in this study were carriers of hlyA gene.

The partition analysis performed in this study indicated that the VF gene astA was an important predictor of metritis second only to the VF gene fimH. A total of 18.5% of the *E. coli* positive cows were infected with astA positive IUPEC. Cows with astA carrying IUPEC were 12 times more likely to develop postpartum metritis and 4.6 times more likely to develop endometritis compared to *E. coli* negative cows. The VF gene astA is an important characteristic of enteroaggregative *E. coli* (EAEC) which is a common cause of diarrhea in humans, especially children diarrhea in developing world, but recently EAEC has also been associated with foodborn infections in industrialized countries (Nataro et al., 1998). The VF gene astA encodes for a 38-aminoacid protein named enteroaggregative *E. coli* heat-stable enterotoxin 1 (EAST1) (Veilleux et al., 2006). The specific role of EAST1 in the pathogenesis of EAEC related diarrhea is still not completely understood (Veilleux et al., 2006). Although, the VF gene astA is typically detected in EAEC it has also been detected in other *E. coli* pathotypes such as EHEC, EPEC, and ETEC as well as other bacterial species such as *Salmonella* (Paiva de Sousa et al., 2001). Abe et al., (2008), demonstrated that UPEC carried VF genes from diarrheagenic *E. coli*, especially those associated with EAEC. It is unknown whether strains of ExPEC have acquired EAEC genes or whether some EAECs are involved in extra intestinal infections such as UTI (Abe et al., 2008). Nevertheless, our study suggests that EAST1 may play an important role in the pathogenesis of postpartum uterine infections.

A multiplex PCR for the detection of cytolethal distending toxin (CDT) capable of detecting CDT-I, CDT-II, CDT-III, and CDT-III was also performed. A total of 25.6% of the E. coli positive cows were cdt positive and when the cdt gene was detected in conjunction with the fimF gene 52% of the cows developed postpartum metritis compared to only 12% for the culture negative cows. Cytolethal distending toxin represents a unique family of toxin causing characteristic enlargement of specific mammalian cells followed by death of the cells (De Rycke et al., 2001). Although, cdt was initially identified in EPEC it known now that cdt is widely present in other E. coli pathotypes mainly in ExPECs (Toth et al., 2003).

Lastly, the DNA gyrase sequence from 41 IUPEC genetically distinct bacteria were aligned with 1 Escherichia Fergusonii strain, 5 Salmonella enteric subsp. enteric strains, 1 Shigella flexneri, 1 Shigella dysenteriae, 2 Shiguella boydii, and 33 Escherichia coli reference strains. Phylogenetic tree reviewed that IUPECs grouped in two major clades, the first being the clade of all ExPECs and the second was mainly composed by IUPECs and adjacent to the ExPEC clade. It has been suggested that the use of gyrB gene for phylogenetic analysis of closely related bacterial strains is preferred over the use of 16S rRNA region, because the gyrB gene evolves at a higher rate providing more heterogeneity for the analysis. Fukushima et al., (2002), suggested that the gyrB region could have high reliability for the identification of pathogenic bacteria.

In summary, it was described here that intrauterine E. coli (IUPEC) appear to play a crucial role in the pathogenesis of postpartum metritis and endometritis. Additionally, several similarities between other extraintestinal E. coli (ExPEC) and IUPEC were identified. There were 6 important virulence factors associated with metritis and endometritis; fimH, astA, cdt, kpsMII, ibeA, and hlyA. The VF gene fimH was the most prevalent VF gene and perhaps the most significant. The VFs astA, cdt, kpsMII, ibeA, and hlyA were highly pathogenic when detected in conjunction with fimH. IUPECs, not surprisingly share similar characteristics from other ExPEC.

TABLE 4

Logistic regression analyzes assessing the effect of several risk factors on the odds of intrauterine contamination by Escherichia coli.

| Risk factors | n | E. coli contamination Adjusted % (95% C.I.) | Adjusted Odds ratio | P-value |
|---|---|---|---|---|
| Twin | 18 | 60 (35-80) | 4.4 | |
| Stillborn | 17 | 55 (32-77) | 3.7 | <0.01 |
| Male alive | 135 | 35 (27-32) | 1.6 | |
| Female alive | 195 | 25 (19-31) | Ref. | |
| BCS < 3 | 142 | 36 (26-47) | 2.3 | |
| BCS = 3 | 97 | 42 (32-52) | 2.8 | <0.01 |
| BCS > 3 | 133 | 20 (13-29) | Ref. | |

TABLE 5

The association of known Escherichia coli virulence factors with the risk of postpartum metritis. The confounding variables farm and parity number were added to all models.

| Virulence Factor | n | Metritis Adj. % (95% C.I.) | Adj. Odds ratio | P-Value |
|---|---|---|---|---|
| Culture negative | 249 | 8 (5-13) | Ref | <0.001 |
| fimH absent | 16 | 17 (5-43) | 2.2 | |
| fimH present | 109 | 37 (28-48) | 6.0 | |

TABLE 5-continued

The association of known Escherichia coli virulence factors with the risk of postpartum metritis. The confounding variables farm and parity number were added to all models.

| Virulence Factor | n | Metritis Adj. % (95% C.I.) | Adj. Odds ratio | P-Value |
|---|---|---|---|---|
| Culture negative | 249 | 8 (5-13) | Ref | <0.001 |
| astA absent | 102 | 28 (20-39) | 4.2 | |
| astA present | 23 | 63 (41-81) | 12 | |
| Culture negative | 249 | 8 (5-13) | Ref | <0.001 |
| ibeA absent | 101 | 31 (22-42) | 5.1 | |
| ibeA present | 24 | 48 (28-69) | 6.1 | |
| Culture negative | 249 | 8 (5-13) | Ref | <0.001 |
| cdt absent | 93 | 30 (21-42) | 4.8 | |
| cdt present | 32 | 46 (29-65) | 6.7 | |
| Culture negative | 249 | 8 (5-13) | Ref | <0.001 |
| hlyA absent | 109 | 31 (22-41) | 4.7 | |
| hlyA present | 16 | 58 (32-80) | 10.5 | |
| Culture negative | 249 | 8 (5-13) | Ref | <0.001 |
| kpsMII absent | 109 | 32 (23-43) | 5.1 | |
| kpsMII present | 16 | 51 (26-75) | 7.1 | |
| Culture negative | 249 | 8 (5-13) | Ref | <0.001 |
| fyfA absent | 90 | 37 (27-49) | 5.1 | |
| fyfA present | 35 | 28 (15-46) | 5.9 | |
| Culture negative | 249 | 8 (5-13) | Ref | <0.001 |
| traT absent | 69 | 32 (23-48) | 4.3 | |
| traT present | 56 | 33 (22-49) | 7.2 | |
| Culture negative | 249 | 8 (5-13) | Ref | <0.001 |
| papG allele 1 absent | 91 | 33 (24-45) | 5.1 | |
| papG allele 1 present | 34 | 37 (22-55) | 5.8 | |
| Culture negative | 249 | 8 (5-13) | Ref | <0.001 |
| papG allele 3 absent | 58 | 31 (20-45) | 5.6 | |
| papG allele 3 present | 67 | 37 (26-51) | 5.1 | |
| Culture negative | 249 | 8 (5-13) | Ref | <0.001 |
| papaH absent | 108 | 35 (26-46) | 5.1 | |
| papaH present | 17 | 28 (11-54) | 7.0 | |

TABLE 6

The association of known Escherichia coli virulence factors with the risk of postpartum endometritis. The confounding variables farm and parity number were added to all models.

| Virulence Factor | n | Endometritis Adj. % (95% C.I.) | Adj. Odds ratio | P-Value |
|---|---|---|---|---|
| Culture negative | 80 | 41 (31-52) | Ref | 0.04 |
| fimH absent | 6 | 33 (8-73) | 0.71 | |
| fimH present | 31 | 64 (52-74) | 2.6 | |
| Culture negative | 80 | 41 (31-52) | Ref | 0.05 |
| astA absent | 24 | 48 (28-69) | 1.3 | |
| astA present | 13 | 76 (47-92) | 4.6 | |
| Culture negative | 80 | 41 (31-52) | Ref | 0.06 |
| ibeA absent | 28 | 53 (34-71) | 1.6 | |
| ibeA present | 9 | 77 (41-94) | 4.8 | |
| Culture negative | 80 | 41 (31-52) | Ref | 0.05 |
| cdt absent | 26 | 52 (32-71) | 1.6 | |
| cdt present | 11 | 72 (41-91) | 3.7 | |
| Culture negative | 80 | 41 (31-52) | Ref | 0.06 |
| hlyA absent | 32 | 55 (37-72) | 1.8 | |
| hlyA present | 5 | 79 (30-97) | 5.5 | |
| Culture negative | 80 | 41 (31-52) | Ref | 0.07 |
| kpsMII absent | 30 | 56 (38-73) | 1.8 | |
| kpsMII present | 7 | 71 (31-93) | 3.4 | |
| Culture negative | 80 | 41 (31-52) | Ref | 0.14 |
| fyfA absent | 28 | 60 (38-77) | 2.1 | |
| fyfA present | 9 | 55 (25-82) | 1.8 | |
| Culture negative | 80 | 41 (31-52) | Ref | 0.22 |
| traT absent | 23 | 65 (42-81) | 2.6 | |
| traT present | 14 | 45 (25-74) | 1.4 | |
| Culture negative | 80 | 41 (31-52) | Ref | 0.07 |
| papG allele 1 absent | 25 | 55 (35-74) | 1.7 | |
| papG allele 1 present | 12 | 66 (37-87) | 2.8 | |
| Culture negative | 80 | 41 (31-52) | Ref | 0.05 |
| papG allele 3 absent | 19 | 46 (25-67) | 1.2 | |
| papG allele 3 present | 18 | 71 (47-88) | 3.6 | |

TABLE 6-continued

The association of known *Escherichia coli* virulence factors with the risk of postpartum endometritis. The confounding variables farm and parity number were added to all models.

| Virulence Factor | n | Endometritis Adj. % (95% C.I.) | Adj. Odds ratio | P-Value |
|---|---|---|---|---|
| Culture negative | 80 | 41 (31-52) | Ref | 0.07 |
| papaH absent | 33 | 56 (38-52) | 1.9 | |
| papaH present | 4 | 74 (24-97) | 4.2 | |

TABLE 7

Cox proportional hazards analyzes of calving to conception interval

| Variable | n | Hazard ratio | 95% CI | P-value |
|---|---|---|---|---|
| Culture negative | 249 | Reference | | 0.007 |
| cdt absence | 93 | 1.6 | 1.1-2.4 | |
| cdt present | 32 | 2.3 | 1.1-4.7 | |
| Culture negative | 249 | Reference | | 0.007 |
| astA absence | 102 | 1.7 | 1.1-2.5 | |
| astA present | 23 | 2.2 | 1.0-5.0 | |
| Culture negative | 249 | Reference | | 0.006 |
| hlyA absence | 109 | 1.7 | 1.1-2.4 | |
| hlyA present | 16 | 3.1 | 1.0-9.8 | |
| Culture negative | 249 | Reference | | 0.007 |
| ibeA absence | 101 | 1.9 | 1.3-2.8 | |
| ibeA present | 24 | 1.4 | 0.7-2.7 | |
| Culture negative | 249 | Reference | | <0.001 |
| kpsMII absence | 109 | 1.6 | 1.1-2.3 | |
| kpsMII present | 16 | 9.2 | 1.3-66 | |
| Culture negative | 249 | Reference | | 0.006 |
| fimH absence | 16 | 1.7 | 0.7-3.9 | |
| fimH present | 109 | 1.8 | 1.2-2.6 | |

REFERENCES

Abe, C. M., F. A. Salvador, I. N. Falsetti, M. A. Vieira, J. Blanco, J. E. Blanco, M. Blanco, A. M. Machado, W. P. Elias, R. T. Hernandes, and T. A. Gomes. 2008. Uropathogenic *Escherichia coli* (UPEC) strains may carry virulence properties of diarrhoeagenic *E. coli*. FEMS Immunol. Med. Microbiol. 52:397-406.

Angulo, F. J., V. N. Nargund and T. C. Chiller. 2004. Evidence of an association between use of anti-microbial agents in food animals and anti-microbial resistance among bacteria isolated from humans and the human health consequences of such resistance. J. Vet. Med. B Infect. Dis. Vet. Public Health. 51:374-379.

Antikainen, J., E. Tarkka, K. Haukka, A. Siitonen, M. Vaara, and J. Kirveskari. 2009. New 16-plex PCR method for rapid detection of diarrheagenic *Escherichia coli* directly from stool samples. Eur. J. Clin. Microbiol. Infect. Dis. 28:899-908.

Arcangioli, M. A., S. Leroy-Setrin, J. L. Martel and E. Chaslus-Dancla. 2000. Evolution of chloramphenicol resistance, with emergence of cross-resistance to florfenicol, in bovine *salmonella typhimurium* strains implicates definitive phage type (DT) 104. J. Med. Microbiol. 49:103-110.

Azawi, O. I. 2008. Postpartum uterine infection in cattle. Anim. Reprod. Sci. 105:187-208.

Barrow, P., M. Lovell and A. Berchieri Jr. 1998. Use of lytic bacteriophage for control of experimental *escherichia coli* septicemia and meningitis in chickens and calves. Clin. Diagn. Lab. Immunol. 5:294-298.

Barrow, P. A. and J. S. Soothill. 1997. Bacteriophage therapy and prophylaxis: Rediscovery and renewed assessment of potential. Trends Microbiol. 5:268-271.

Bennett, P. M. 2008. Plasmid encoded antibiotic resistance: Acquisition and transfer of antibiotic resistance genes in bacteria. Br. J. Pharmacol. 153 Suppl 1:S347-57.

Bicalho, R. C., S. H. Cheong, K. N. Galvao, L. D. Warnick, and C. L. Guard. 2007. Effect of twin birth calvings on milk production, reproductive performance, and survival of lactating cows. J. Am. Vet. Med. Assoc. 231:1390-1397.

Bicalho, R. C., K. N. Galvao, S. H. Cheong, R. O. Gilbert, L. D. Warnick, and C. L. Guard. 2007. Effect of stillbirths on dam survival and reproduction performance in Holstein dairy cows. J. Dairy Sci. 90:2797-2803.

Biswas, B., S. Adhya, P. Washart, B. Paul, A. N. Trostel, B. Powell, R. Carlton and C. R. Merril. 2002. Bacteriophage therapy rescues mice bacteremic from a clinical isolate of vancomycin-resistant *enterococcus faecium*. Infect. Immun. 70:204-210.

Bondurant, R. H. 1999. Inflammation in the bovine female reproductive tract. J. Anim. Sci. 77 Suppl 2:101-110.

Borsberry, S. and H. Dobson. 1989. Periparturient diseases and their effect on reproductive performance in five dairy herds. Vet. Rec. 124:217-219.

Bradford, P. A., P. J. Petersen, I. M. Fingerman and D. G. White. 1999. Characterization of expanded-spectrum cephalosporin resistance in *E. coli* isolates associated with bovine calf diarrhoeal disease. J. Antimicrob. Chemother. 44:607-610.

Brussow, H. 2005. Phage therapy: The *escherichia coli* experience. Microbiology. 151:2133-2140.

Callaway, T. R., T. S. Edrington, A. D. Brabban, R. C. Anderson, M. L. Rossman, M. J. Engler, M. A. Can, K. J. Genovese, J. E. Keen, M. L. Looper, E. M. Kutter and D. J. Nisbet. 2008. Bacteriophage isolated from feedlot cattle can reduce *escherichia coli* O157:H7 populations in ruminant gastrointestinal tracts. Foodborne Pathog. Dis. 5:183-191.

Chen J and Novick R P. 2009. Phage-Mediated Intergeneric Transfer of Toxin Genes.

Clermont, O., S. Bonacorsi and E. Bingen. 2000. Rapid and simple determination of the *escherichia coli* phylogenetic group. Appl. Environ. Microbiol. 66:4555-4558.

Clermont, O., H. Dhanji, M. Upton, T. Gibreel, A. Fox, D. Boyd, M. R. Mulvey, P. Nordmann, E. Ruppe, J. L. Sarthou, T. Frank, S. Vimont, G. Arlet, C. Branger, N. Woodford, and E. Denamur. 2009. Rapid detection of the O25b-ST131 clone of *Escherichia coli* encompassing the CTX-M-15-producing strains. J. Antimicrob. Chemother. 64:274-277.

Clinical and Laboratory Standards Institute (CLSI), 2008. Performance Standards for Antimicrobial Disk and Dilution Susceptibility Test for Bacteria Isolated from Animals Approved Standard, 3rd edition. CLSI document M31-A3. Clinical and Laboratory Standards Institute, Wayne, Pa.

Clokie, M. R. J. and A. M. Kropinski. 2009. Bacteriophages: Methods and Protocols. Humana Press; Springer distributor, Totowa, N.J.; London.

de Brito, B. G., L. C. Gaziri, and M. C. Vidotto. 2003. Virulence factors and clonal relationships among *Escherichia coli* strains isolated from broiler chickens with cellulitis. Infect. Immun. 71:4175-4177.

De Rycke, J., and E. Oswald. 2001. Cytolethal distending toxin (CDT): a bacterial weapon to control host cell proliferation? FEMS Microbiol. Lett. 203:141-148.

Dohmen, M. J., K. Joop, A. Sturk, P. E. Bols and J. A. Lohuis. 2000. Relationship between intra-uterine bacterial contamination, endotoxin levels and the development of endometritis in postpartum cows with dystocia or retained placenta. Theriogenology. 54:1019-1032.

Fey, P. D., T. J. Safranek, M. E. Rupp, E. F. Dunne, E. Ribot, P. C. Iwen, P. A. Bradford, F. J. Angulo and S. H. Hinrichs. 2000. Ceftriaxone-resistant *salmonella* infection acquired by a child from cattle. N. Engl. J. Med. 342:1242-1249.

Foldi, J., M. Kulcsar, A. Pecsi, B. Huyghe, C. de Sa, J. A. Lohuis, P. Cox and G. Huszenicza. 2006. Bacterial complications of postpartum uterine involution in cattle. Anim. Reprod. Sci. 96:265-281.

Fukushima, M., K. Kakinuma, and R. Kawaguchi. 2002. Phylogenetic analysis of *Salmonella, Shigella*, and *Escherichia coli* strains on the basis of the gyrB gene sequence. J. Clin. Microbiol. 40:2779-2785.

Fulwider, W. K., T. Grandin, B. E. Rollin, T. E. Engle, N. L. Dalsted and W. D. Lamm. 2008. Survey of dairy management practices on one hundred thirteen north central and northeastern United States dairies. J. Dairy Sci. 91:1686-1692.

Germon, P., Y. H. Chen, L. He, J. E. Blanco, A. Bree, C. Schouler, S. H. Huang, and M. Moulin-Schouleur. 2005. ibeA, a virulence factor of avian pathogenic *Escherichia coli*. Microbiology. 151:1179-1186.

Gilbert, R. O., S. T. Shin, C. L. Guard, H. N. Erb and M. Frajblat. 2005. Prevalence of endometritis and its effects on reproductive performance of dairy cows. Theriogenology. 64:1879-1888.

Gilmore, A. 1986. Chloramphenicol and the politics of health. CMAJ. 134:423, 426-8, 433-5.

Herzer, P. J., S. Inouye, M. Inouye and T. S. Whittam. 1990. Phylogenetic distribution of branched RNA-linked multicopy single-stranded DNA among natural isolates of *escherichia coli*. J. Bacteriol. 172:6175-6181.

Higgins, J., C. Hohn, S. Hornor, M. Frana, M. Denver, and R. Joerger. 2007. Genotyping of *Escherichia coli* from environmental and animal samples. J. Microbiol. Methods. 70:227-235.

Huang, S. H., Z. S. Wan, Y. H. Chen, A. Y. Jong, and K. S. Kim. 2001. Further characterization of *Escherichia coli* brain microvascular endothelial cell invasion gene ibeA by deletion, complementation, and protein expression. J. Infect. Dis. 183:1071-1078.

Johnson, J. R., P. Delavari, M. Kuskowski, and A. L. Stell. 2001. Phylogenetic distribution of extraintestinal virulence-associated traits in *Escherichia coli*. J. Infect. Dis. 183:78-88.

Johnson, J. R., M. A. Kuskowski, T. T. O'Bryan, and J. N. Maslow. 2002. Epidemiological correlates of virulence genotype and phylogenetic background among *Escherichia coli* blood isolates from adults with diverse-source bacteremia. J. Infect. Dis. 185:1439-1447.

Johnson, T. J., Y. Wannemuehler, S. J. Johnson, A. L. Stell, C. Doetkott, J. R. Johnson, K. S. Kim, L. Spanjaard, and L. K. Nolan. 2008. Comparison of extraintestinal pathogenic *Escherichia coli* strains from human and avian sources reveals a mixed subset representing potential zoonotic pathogens. Appl. Environ. Microbiol. 74:7043-7050.

Kaper, J. B., J. P. Nataro, and H. L. Mobley. 2004. Pathogenic *Escherichia coli*. Nat. Rev. Microbiol. 2:123-140.

Lally, E. T., R. B. Hill, I. R. Kieba, and J. Korostoff. 1999. The interaction between RTX toxins and target cells. Trends Microbiol. 7:356-361.

Lang, L. H. 2006. FDA approves use of bacteriophages to be added to meat and poultry products. Gastroenterology. 131:1370-1370.

Langermann, S., S. Palaszynski, M. Barnhart, G. Auguste, J. S. Pinkner, J. Burlein, P. Barren, S. Koenig, S. Leath, C. H. Jones, and S. J. Hultgren. 1997. Prevention of mucosal *Escherichia coli* infection by FimH-adhesin-based systemic vaccination. Science. 276:607-611.

Linden, T. C., R. C. Bicalho, and D. V. Nydam. 2009. Calf birth weight and its association with calf and cow survivability, disease incidence, reproductive performance, and milk production. J. Dairy Sci. 92:2580-2588.

Livermore, D. M. 1995. Beta-lactamases in laboratory and clinical resistance. Clin. Microbiol. Rev. 8:557-584.

Lockett, T. J. 1990. A bacteriophage lambda DNA purification procedure suitable for the analysis of DNA from either large or multiple small lysates. Anal. Biochem. 185:230-234.

Lusiak-Szelachowska, M., B. Weber-Dabrowska and A. Gorski. 2006. The presence of bacteriophages in human feces and their potential importance. Pol. Merkur Lekarski. 21:381-383.

Maidhof, H., B. Guerra, S. Abbas, H. M. Elsheikha, T. S. Whittam and L. Beutin. 2002. A multiresistant clone of shiga toxin-producing *escherichia coli* O118:[H16] is spread in cattle and humans over different European countries. Appl. Environ. Microbiol. 68:5834-5842.

Malinen, E., A. Kassinen, T. Rinttila, and A. Palva. 2003. Comparison of real-time PCR with SYBR Green 1 or 5'-nuclease assays and dot-blot hybridization with rDNA-targeted oligonucleotide probes in quantification of selected faecal bacteria. Microbiology. 149:269-277.

Matsuzaki, S., M. Yasuda, H. Nishikawa, M. Kuroda, T. Ujihara, T. Shuin, Y. Shen, Z. Jin, S. Fujimoto, M. D. Nasimuzzaman, H. Wakiguchi, S. Sugihara, T. Sugiura, S. Koda, A. Muraoka and S. Imai. 2003. Experimental protection of mice against lethal *staphylococcus aureus* infection by novel bacteriophage phi MR11. J. Infect. Dis. 187:613-624.

McDougall, S., R. Macaulay, and C. Compton. 2007. Association between endometritis diagnosis using a novel intravaginal device and reproductive performance in dairy cattle. Anim. Reprod. Sci. 99:9-23.

Melendez, P., J. McHale, J. Bartolome, L. F. Archbald and G. A. Donovan. 2004. Uterine involution and fertility of holstein cows subsequent to early postpartum PGF2alpha treatment for acute puerperal metritis. J. Dairy Sci. 87:3238-3246.

Merril, C. R., D. Scholl and S. L. Adhya. 2003. The prospect for bacteriophage therapy in western medicine. Nat. Rev. Drug Discov. 2:489-497.

Moreira, M. A., J. A. Oliveira, L. M. Teixeira and C. A. Moraes. 2005. Detection of a chloramphenicol efflux system in *escherichia coli* isolated from poultry carcass. Vet. Microbiol. 109:75-81.

Moreno, E., J. R. Johnson, T. Perez, G. Prats, M. A. Kuskowski, and A. Andreu. 2009. Structure and urovirulence characteristics of the fecal *Escherichia coli* population among healthy women. Microbes Infect. 11:274-280.

Moreno, E., I. Planells, G. Prats, A. M. Planes, G. Moreno, and A. Andreu. 2005. Comparative study of *Escherichia coli* virulence determinants in strains causing urinary tract bacteremia versus strains causing pyelonephritis and other sources of bacteremia. Diagn. Microbiol. Infect. Dis. 53:93-99.

Nataro, J. P., T. Steiner, and R. L. Guerrant. 1998. Enteroaggregative *Escherichia coli*. Emerg. Infect. Dis. 4:251-261.

Obata-Yasuoka, M., W. Ba-Thein, T. Tsukamoto, H. Yoshikawa, and H. Hayashi. 2002. Vaginal *Escherichia coli* share common virulence factor profiles, serotypes and phylogeny with other extraintestinal *E. coli*. Microbiology. 148:2745-2752.

Paiva de Sousa, C., and J. D. Dubreuil. 2001. Distribution and expression of the astA gene (EAST1 toxin) in *Escherichia coli* and *Salmonella*. Int. J. Med. Microbiol. 291:15-20.

Picard, B., J. S. Garcia, S. Gouriou, P. Duriez, N. Brahimi, E. Bingen, J. Elion and E. Denamur. 1999. The link between phylogeny and virulence in *escherichia coli* extraintestinal infection. Infect. Immun. 67:546-553.

Picard, B. and P. Goullet. 1988. Correlation between electrophoretic types B1 and B2 of carboxylesterase B and host-dependent factors in *escherichia coli* septicaemia. Epidemiol. Infect. 100:51-61.

Revel, H. R. 1967. Restriction of nonglucosylated T-even bacteriophage: Properties of permissive mutants of *escherichia coli* B and K12. Virology. 31:688-701.

Rushen, J. and A. M. de Passille. 2006. Effects of roughness and compressibility of flooring on cow locomotion. J. Dairy Sci. 89:2965-2972.

Sambrook, J. and D. W. Russell. 2001. Molecular Cloning: A Laboratory Manual. 3rd ed. Cold Spring Harbor Laboratory Press, Cold Spring Harbor, N.Y.

Sawant, A. A., N. V. Hegde, B. A. Straley, S. C. Donaldson, B. C. Love, S. J. Knabel and B. M. Jayarao. 2007. Antimicrobial-resistant *enteric* bacteria from dairy cattle. Appl. Environ. Microbiol. 73:156-163.

Schierack, P., H. Steinruck, S. Kleta and W. Vahjen. 2006. Virulence factor gene profiles of *escherichia coli* isolates from clinically healthy pigs. Appl. Environ. Microbiol. 72:6680-6686. Sheldon, I. M. 2004. The postpartum uterus. Vet. Clin. North Am. Food Anim. Pract. 20:569-591.

Schwarz, S., C. Kehrenberg, B. Doublet and A. Cloeckaert. 2004. Molecular basis of bacterial resistance to chloramphenicol and florfenicol. FEMS Microbiol. Rev. 28:519-542. Settepani, J. A. 1984. The hazard of using chloramphenicol in food animals. J. Am. Vet. Med. Assoc. 184: 930-931.

Sheldon, I. M. 2004a. The postpartum uterus. Vet. Clin. North Am. Food Anim. Pract. 20:569-591.

Sheldon, I. M., M. Bushnell, J. Montgomery and A. N. Rycroft. 2004. Minimum inhibitory concentrations of some antimicrobial drugs against bacteria causing uterine infections in cattle. Vet. Rec. 155:383-387.

Sheldon, I. M., G. S. Lewis, S. LeBlanc and R. O. Gilbert. 2006. Defining postpartum uterine disease in cattle. Theriogenology. 65:1516-1530.

Sheldon, I. M. and H. Dobson. 2004. Postpartum uterine health in cattle. Anim. Reprod. Sci. 82-83:295-306.

Sheldon, I. M., D. E. Noakes, A. N. Rycroft, D. U. Pfeiffer and H. Dobson. 2002. Influence of uterine bacterial contamination after parturition on ovarian dominant follicle selection and follicle growth and function in cattle. Reproduction. 123:837-845.

Sheldon, I. M., A. N. Rycroft and C. Zhou. 2004. Association between postpartum pyrexia and uterine bacterial infection in dairy cattle. Vet. Rec. 154:289-293.

Sheldon, I. M., A. N. Rycroft, B. Dogan, M. Craven, J. J. Bromfield, A. Chandler, M. H. Roberts, S. B. Price, R. O. Gilbert, and K. W. Simpson. 2010. Specific strains of *Escherichia coli* are pathogenic for the endometrium of cattle and cause pelvic inflammatory disease in cattle and mice. PLoS One. 5:e9192.

Silva, E., M. Gaivao, S. Leitao, B. H. Jost, C. Carneiro, C. L. Vilela, L. Lopes da Costa and L. Mateus. 2008. Genomic characterization of *arcanobacterium pyogenes* isolates recovered from the uterus of dairy cows with normal puerperium or clinical metritis. Vet. Microbiol. 132:111-118.

Silva, E., S. Leitao, T. Tenreiro, C. Pomba, T. Nunes, L. Lopes da Costa, and L. Mateus. 2009. Genomic and phenotypic characterization of *Escherichia coli* isolates recovered from the uterus of puerperal dairy cows. J. Dairy Sci. 92:6000-6010.

Simpson, K. W., B. Dogan, M. Rishniw, R. E. Goldstein, S. Klaessig, P. L. McDonough, A. J. German, R. M. Yates, D. G. Russell, S. E. Johnson, D. E. Berg, J. Harel, G. Bruant, S. P. McDonough and Y. H. Schukken. 2006. Adherent and invasive *escherichia coli* is associated with granulomatous colitis in boxer dogs. Infect. Immun. 74:4778-4792.

Smith, J. L., P. M. Fratamico and N. W. Gunther. 2007. Extraintestinal pathogenic *escherichia coli*. Foodborne Pathog. Dis. 4:134-163.

Smith, Y. C., S. B. Rasmussen, K. K. Grande, R. M. Conran, and A. D. O'Brien. 2008. Hemolysin of uropathogenic *Escherichia coli* evokes extensive shedding of the uroepithelium and hemorrhage in bladder tissue within the first 24 hours after intraurethral inoculation of mice. Infect. Immun. 76:2978-2990.

Snyder, L., L. Gold and E. Kutter. 1976. A gene of bacteriophage T4 whose product prevents true late transcription on cytosine-containing T4 DNA. Proc. Natl. Acad. Sci. U.S.A. 73:3098-3102.

Soothill, J. S. 1992. Treatment of experimental infections of mice with bacteriophages. J. Med. Microbiol. 37:258-261.

Struelens, M. J., O. Denis, and H. Rodriguez-Villalobos. 2004. Microbiology of nosocomial infections: progress and challenges. Microbes Infect. 6:1043-1048.

Summers, W. C. 2001. BACTERIOPHAGE THERAPY. Annu Rev. Microbiol. 55:437-451.

Tamura, K., and M. Nei. 1993. Estimation of the number of nucleotide substitutions in the control region of mitochondrial DNA in humans and chimpanzees. Mol. Biol. Evol. 10:512-526.

Tollefson, L., P. J. Fedorka-Cray and F. J. Angulo. 1999. Public health aspects of antibiotic resistance monitoring in the USA. Acta Vet. Scand. Suppl. 92:67-75.

Tollefson, L. and M. A. Miller. 2000. Antibiotic use in food animals: Controlling the human health impact. J. AOAC Int. 83:245-254.

Toth, I., F. Herault, L. Beutin, and E. Oswald. 2003. Production of cytolethal distending toxins by pathogenic *Escherichia coli* strains isolated from human and animal sources: establishment of the existence of a new cdt variant (Type IV). J. Clin. Microbiol. 41:4285-4291.

Tucker, C. B., D. M. Weary, A. M. de Passille, B. Campbell and J. Rushen. 2006. Flooring in front of the feed bunk affects feeding behavior and use of freestalls by dairy cows. J. Dairy Sci. 89:2065-2071.

United States Department of Agriculture. National Antimicrobial Resistance Monitoring System, *Escherichia coli* —2005. Bacterial Epidemiology and Antimicrobial Resistance. [homepage on the Internet]. Last Updated Jan. 14, 2005. Available from on the world web at ars.usda.gov/Business/docs.htm?docid=6770. Last accessed Mar. 16, 2009.

Viscardi, M., A. G. Perugini, C. Auriemma, F. Capuano, S. Morabito, K. P. Kim, M. J. Loessner and G. Iovane. 2008. Isolation and characterisation of two novel coliphages with high potential to control antibiotic-resistant pathogenic *escherichia coli* (EHEC and EPEC). Int. J. Antimicrob. Agents. 31:152-157.

Veilleux, S., and J. D. Dubreuil. 2006. Presence of *Escherichia coli* carrying the EAST1 toxin gene in farm animals. Vet. Res. 37:3-13.

Walsh, C. 2003. Where will new antibiotics come from? Nat. Rev. Microbiol. 1:65-70.

Wang, G., T. S. Whittam, C. M. Berg, and D. E. Berg. 1993. RAPD (arbitrary primer) PCR is more sensitive than multilocus enzyme electrophoresis for distinguishing related bacterial strains. Nucleic Acids Res. 21:5930-5933.

White, D. G., C. Hudson, J. J. Maurer, S. Ayers, S. Zhao, M. D. Lee, L. Bolton, T. Foley and J. Sherwood. 2000. Characterization of chloramphenicol and florfenicol resistance in *escherichia coli* associated with bovine diarrhea. J. Clin. Microbiol. 38:4593-4598.

Winokur, P. L., D. L. Vonstein, L. J. Hoffman, E. K. Uhlenhopp and G. V. Doern. 2001. Evidence for transfer of CMY-2 AmpC beta-lactamase plasmids between *escherichia coli* and *salmonella* isolates from food animals and humans. Antimicrob. Agents Chemother. 45:2716-2722.

Zerbe, H., C. Ossadnik, W. Leibold and H. J. Schuberth. 2001. Influence of *escherichia coli* and *arcanobacterium pyogenes* isolated from bovine puerperal uteri on phenotypic and functional properties of neutrophils. Vet. Microbiol. 79:351-365.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

The invention claimed is:

1. A composition comprising inactivated or attenuated cells or cell lysates of said inactivated or attenuated cells of at least one isolated bovine intrauterine strain of pathogenic *Escherichia coli* expressing virulence factors FimH, cytolethal distending toxin (cdt) and hlyA and at least one of kpsII and ibeA, and a first pharmaceutically acceptable carrier, wherein said first pharmaceutically acceptable carrier is an effective amount of adjuvant.

2. The composition of claim 1, wherein said composition comprises an amount of said inactivated or attenuated cells or cell lysates sufficient to elicit an immune response to said isolated strain of pathogenic *Escherichia coli*.

3. The composition of claim 1, further comprising at least two isolated intrauterine strains of pathogenic *Escherichia coli* that express cytolethal distending toxin (cdt) and hlyA and at least one of kpsII and ibeA.

4. A method comprising administering the composition of claim 1 to treat a subject, wherein said subject is at risk of developing uterine disease or suffer from uterine disease.

5. The method of claim 4, wherein said subject is a bovine.

6. The composition of claim 1, wherein said isolated strain of pathogenic *Escherichia coli* of claim 1 comprises a gyrB gene sequence at least 97% identical to one of SEQ ID NOs: 3 and 4.

7. The composition of claim 1, wherein said at least one isolated intrauterine strain of pathogenic *Escherichia coli* is selected from the group consisting of strain ATCC PTA-10831, strain ATCC PTA-10832, and combinations thereof.

8. A composition comprising inactivated or attenuated cells or cell lysates of said inactivated or attenuated cells of at least one isolated intrauterine strain of pathogenic *Escherichia coli* selected from the group consisting of strain ATCC PTA-10831, strain ATCC PTA-10832, and combinations thereof, and a first pharmaceutically acceptable carrier, wherein said first pharmaceutically acceptable carrier is an effective amount of adjuvant.

9. The composition of claim 8, wherein said composition comprises an amount of said inactivated or attenuated cells or cell lysates sufficient to elicit an immune response to said isolated strain of pathogenic *Escherichia coli*.

* * * * *